(12) United States Patent
Kinch et al.

(10) Patent No.: US 8,207,209 B2
(45) Date of Patent: Jun. 26, 2012

(54) METHODS OF INHIBITING VIRAL INFECTION

(75) Inventors: Michael Kinch, Laytonsville, MD (US); Michael Goldblatt, McLean, VA (US)

(73) Assignee: Functional Genetics, Inc., Gaithersburg, MD (US)

( * ) Notice: Subject to any disclaimer, the term of this patent is extended or adjusted under 35 U.S.C. 154(b) by 434 days.

(21) Appl. No.: 12/256,571

(22) Filed: Oct. 23, 2008

(65) Prior Publication Data

US 2009/0170890 A1    Jul. 2, 2009

Related U.S. Application Data

(60) Provisional application No. 60/982,227, filed on Oct. 24, 2007.

(51) Int. Cl.
*A61K 31/4184*    (2006.01)

(52) U.S. Cl. ...................................... 514/394

(58) Field of Classification Search ........................ None
See application file for complete search history.

(56) References Cited

U.S. PATENT DOCUMENTS

| | | | |
|---|---|---|---|
| 6,248,523 B1 | 6/2001 | Cohen et al. | |
| 6,835,816 B2 | 12/2004 | Cohen et al. | |
| 2004/0223972 A1 | 11/2004 | Li | |
| 2005/0271647 A1 | 12/2005 | Baltimore et al. | |
| 2006/0111312 A1 | 5/2006 | Eshleman et al. | |
| 2007/0112048 A1 | 5/2007 | Bavari et al. | |
| 2007/0112049 A1 | 5/2007 | Bavari et al. | |
| 2009/0012107 A1 * | 1/2009 | Aman et al. | 514/275 |

FOREIGN PATENT DOCUMENTS

WO    WO 2008/089125    7/2008

OTHER PUBLICATIONS

Meissner et al., Pediatrics (Jun. 2004), 113(6), pp. 1814-1916.*
Allende et al., Journal of Virology, (2000), 74(22), pp. 10834-10837.*
E. De Clercq, et al., "Diaryl Amidine Derivatives as Oncornaviral DNA Polymerase Inhibitors", *J. Med. Chem.*, 23: pp. 787-795 (1980).
Monica Garcia, et al., "Design, synthesis and biological activity of a targeted library of potential tryptase inhibitors", *Org. Biomol. Chem.*, 2: pp. 1633-1642 (2004).
Cianci, et al., Orally Active Fusion Inhibitor of Respiratory Syncytial Virus, Antimicrobial Agents and Chemotherapy, Feb. 2004, p. 413-422.
International Ser. Report, Mar. 16, 2009, Functional Genetics, Inc.

* cited by examiner

*Primary Examiner* — Phyllis G. Spivack
(74) *Attorney, Agent, or Firm* — Steven B. Kelber; Berenato & White, LLC

(57) ABSTRACT

A method of inhibiting viral respiratory infection in a mammal in need of same, includes administering an effective amount of 2-[2-(5-carbamimidoyl-benzofuran-2-yl)-vinyl]-H-benzoimidazole-5-carboxamidine or the Bis-N-hydroxyamidine prodrug thereof, prior to viral infection, or therapeutically following viral infection, to inhibit that viral infection. The compound selectively inhibits Caspase 2 and/or 8 as to prevent infective viral particle release. It is optionally administered IV, IP, orally or via other conventional administration routes in a dosage range of 1 ng/kg-200 mg/kg of body weight.

9 Claims, 73 Drawing Sheets

| Compound | Parent Structure |
|---|---|
| 294202 | 294202 |
| 306365 | |
| 369723 | 369723 |
| 240890 | 240890 |

FIG.6A

| | | | |
|---|---|---|---|
| 240891 | 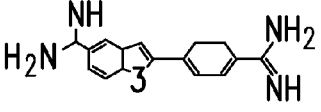 | 240900 | 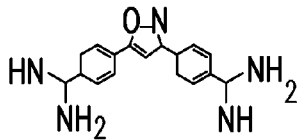 |
| 240893 | 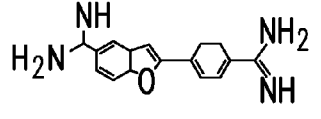 | 266472 | 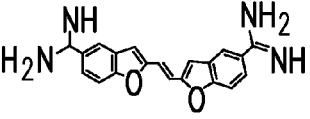 |
| 300510 | 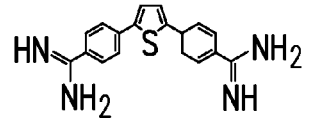 | 278995 | 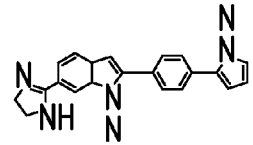 |
| 294206 | 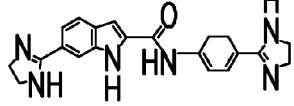 | 278999 | 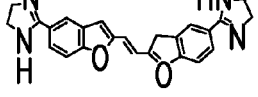 |
| 240894 | 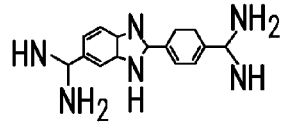 | 290108 | 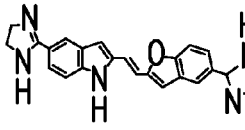 |
| 240895 | 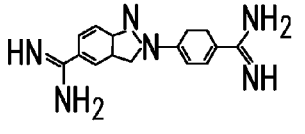 | 249199 | 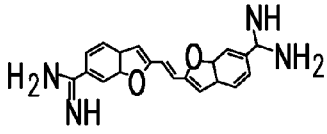 |
| 240898 | 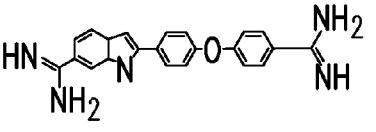 | | |
| 240899 | 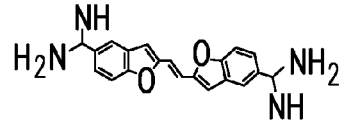 | | |
FIG.6B

| | |
|---|---|
| 300509 | (structure: indole with guanidine/amidine groups and phenyl-amidine substituent) |
| 300511 | (structure: bis-benzofuran diamidine linked by diene) |
| 308569 | (structure: benzothiophene-amidine linked to phenyl-amidine) |
| 308571 | (structure: bis-benzofuran bis-imidazoline linked by diene) |
| 308573 | (structure: benzofuran-imidazoline linked via diene to phenyl-imidazoline) |
| 330688 | (structure: bis-indole bis-imidazoline) |
| 330689 | (structure: indole with amidine and diaminomethyl groups) |
| 341909 | (structure: benzothiophene with guanidinyl-methyl linker and phenyl-guanidine) |
| 607617 | (structure: bis-benzofuran diamidine linked by ethylene) |

Broad Spectrum Potential – DNA viruses

Cowpox Virus

FIG. 12

PRRS Virus

| Compound | $EC_{100}$ (μM) | $EC_{90}$ (μM) | $IC50^3$ (μM) |
| --- | --- | --- | --- |
| 365 | 3 | 1 | >50 |
| 723 | >25 | >25 | 50 |

- Note: PRRS virus shares activity and homology with other animal viruses and human coronaviruses

FIG. 13

*Beyond Human Diseases...*

Bovine Corona Virus

| Compound | EC$_{100}$ (μM) |
|---|---|
| 365 | 12.5 |
| 723 | >25 |

● Note: Bovine corona virus shares homology with SARS

Protection from Ebola

Endpoint: Survival Following EBOV Challenge

Dose: 10 mg/kg: 200 μg/mouse/injection

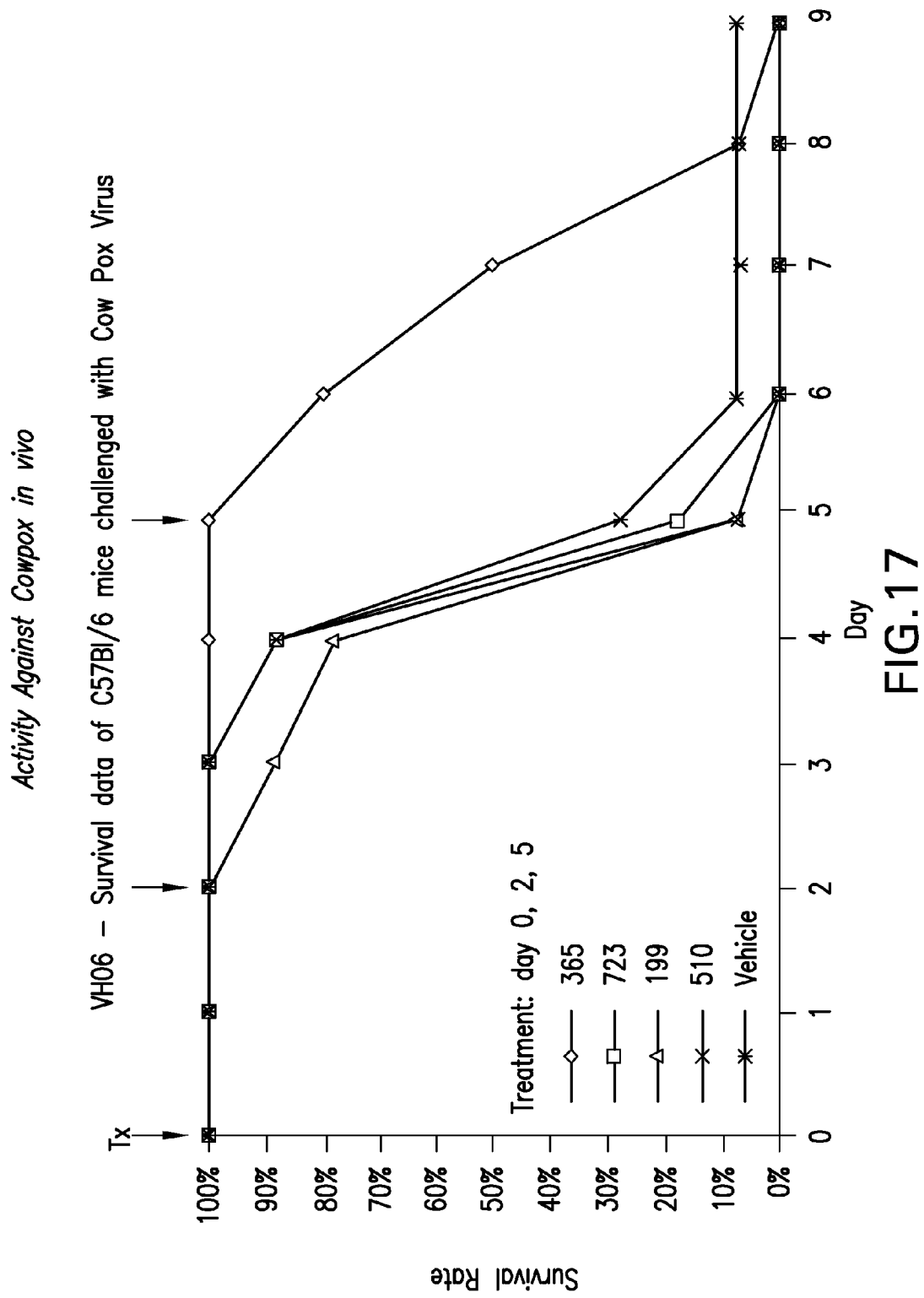

Summary of Leading Compounds

| Compound | EBOV | MARV | Flu | Lassa | RVF | Pox | PRRS | Dengue | HIV |
|---|---|---|---|---|---|---|---|---|---|
| 365 | +++ I,P,T | +I | +I | +++I | +++I | +++I | +++I | +++I | ++ |
| 202 | +++ I,P,T | NT | +++T | NT | +++I | +++I | NT | NT | NT |
| 199 | +++T | +++T | NT | NT | NT | NT | NT | NT | NT |
| 206 | +++I | NT | NT | NT | NT | +++I | NT | NT | NT |
| 723 | +++ I,P,T | NT | −I | NT | −I | −I | −I | ++ | NT |
| 510 | +++I | NT | NT | NT | NT | +++I | −I | NT | NT |

Notes:
1) I= *in vitro*, P= *in vivo* (prophylaxis), T= *in vivo* (therapeutic)
2) +++ = >3 log reduction or 100% protection
3) Only 365 tested in a therapeutic setting (so far)
4) NT = Not (yet) Tested

FIG. 18

Viral Titers and Cell-Based Safety

| Virus | $EC_{50}$ (μM) | Titer Reduction | $SI_{50}$ |
|---|---|---|---|
| RSV | 0.015 | >7 log | >9000 |
| PIV | 0.015 | >3 log | >5000 |
| Ebola | 0.034 | 4 log | 2433 |
| Marburg | 0.050 | 4 log | >2000 |
| HBV | 0.12 | Not tested | >400 |
| Dengue | 6.7–12.3 | Not tested | ~44 |
| Lassa | 1.200 | 3 log | >60 |
| Influenza | 15.0 | Not tested | 22 |
| HIV | 100 | Not tested | 2 |

Hemorrhagic Fever Viruses

In Depth Analysis

|  | CC$_{50}$ | EC$_{50}$ | "SI" |
|---|---|---|---|
| EBOV | >80 μM | 0.034 μM | >2433 |
| MARV | >80 μM | 0.050 μM | >2000 |

Incidence and Related Mononegavirales

| Virus | Distribution | Incidence |
|---|---|---|
| Rabies | Worldwide | >60,000/yr |
| Measles | Worldwide | Rare; sporadic outbreaks |
| Paramyxo and Pneumoviruses (RSV, PIV, HMPV) | Worldwide | Endemic |

Initial Assay
Host Cell Survival

Ebola

Marburg

Host infection (%) vs Compound (μM)

Mouse Model of Ebola
Single Dose, 24 hr post infection

Treatment: d1
□ 10 mg/kg
□ 5 mg/kg
● Vehicle

Mouse Model of Ebola
Single Dose, 96 hr post infection

Treatment: 10 mg/kg
- ■ d4
- ● Vehicle

FIG. 27

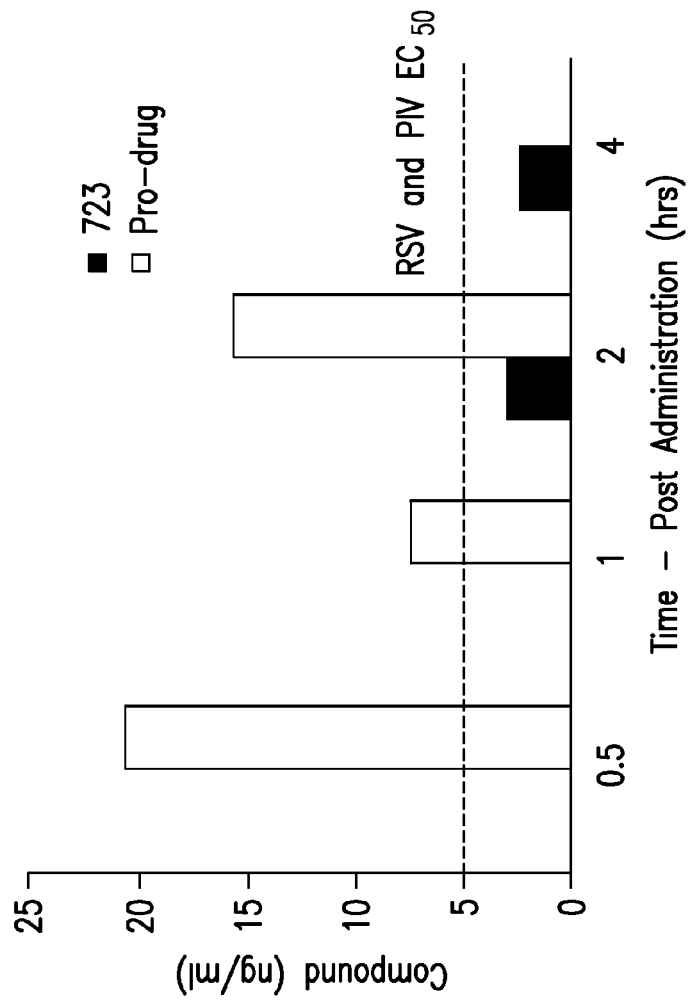
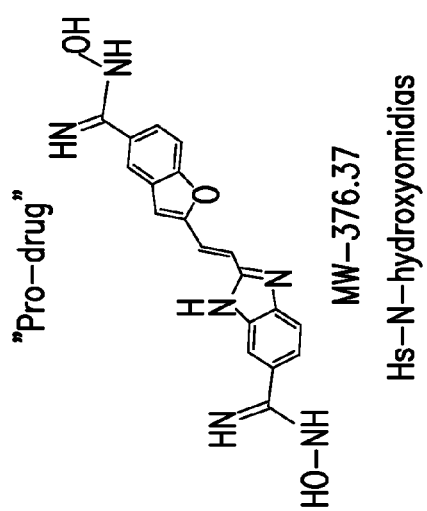
FIG.33

Cell-Based Safety Observations

723

| Cell Model | Cell Type | $CC_{50}$ |
|---|---|---|
| MDCK | Ca Epith | >320 μM |
| HEK-293T | Hu Epith | >200 μM |
| Vero E6* | AGM Epith | >50 μM |
| Marc-145** | AGM Epith | 50 μM |
| MT-4 | Hu T cell | 195 μM |
| A549 | Hu Lung | 180 μM |
| Vero | AGM Epith | >50 μM |
| Hμ PBMC | Hu PBMC | >100 μM |
| PK-15** | Porc Epith | >50 μM |

Chemistry
MW:604
Chemical Formula:$C_{28}H_{38}N_6$
Synthesis: 4 steps

Mechanism of Action
Host-Based Mechanism
Blocks late stage of viral lifecycle
Inhibits TSG-101 interaction with viral late domain proteins *in situ*

Pharmacokinetics
$T_{1/2}$ ~10hr(est)-mouse

Quino[8,7-h]quinoline-1,7-diamine, N,N'-bis[3-(dimethylamino)propyl]-3,9-dimethyl-, tetrahydrochloride

Animal-Based Studies

Efficacy
100% Protection-EBOV-Prophylaxis
100% Protection-EBOV-Therapeutic
100% Increase in time of survival-Poxvirus

Safety
$LD_{50}$:>50mg/kg

Cell-Based Studies

Efficacy
HIV-1: $EC_{50}$=0.11;SI=58
HCV: $EC_{50}$=0.24 μM;SI=13
Lassa: $EC_{50}$=<0.2μM;SI=>500
SARS: $EC_{50}$=0.3μM;SI=>3
Rift Valley Fever: $EC_{50}$=0.37;SI=27
PRRS: $EC_{50}$=0.3μM;SI=>150
Dengue:$EC_{50}$=<10μM;SI=>20
Bov Coronav: $EC_{50}$=1μM;SI=50
EBOV: $EC_{50}$=2μM;SI=5
MARV: $EC_{50}$=10μM;SI=2

Cell-Based Safety ($CC_{50}$)
Huh-7: 3.3 μM
VeroE6: 10μM
MT-4:6 μM
Marc-145:>50 μM
PK-15:25 μM
DC-Sign:20 μM Non-GLP Safety
Not

FIG.37

Summary of Leading Compounds in Cell-Based Assays

| Virus | Type | $EC_{50}$ | $CC_{50}$ | $SI_{50}$ |
|---|---|---|---|---|
| HIV-1 | Retrovirus | 0.11 | 6 | 58 |
| HCV | Flavivirus | 0.24 μM | 3.3 μM | 13 |
| Lassa Fever | Arenavirus | <0.2 | 10 | >500 |
| SARS | Coronavirus | 0.3 | >1 | >3 |
| Rift Valley Fever | Bunyavirus | 0.37 | 10 | 27 |
| PRRS-N.Americam | Arterivirus | 0.3 (est) | >50 | >150 |
| PRRS-European | Arterivirus | 0.3 (est) | >50 | >150 |
| Dengue | Flavivirus | 0.8 | 20 | 25 |
| Bovine Coronavirus | Coronavirus | 1 (est) | 50 | 50 |
| Ebola Zarie | Filovirus | 2 | 10 | 5 |
| Marburg | Filovirus | 10 | 20 | 2 |

PRRSv Inhibition

| Target Cell | $EC_{100}$ | $EC_{90}$ | $CC_{90}$ | "SI" |
|---|---|---|---|---|
| Marc-145 | 3.2 | 1.6 | >50 | >200(est) |
| Primary Porc. MΦ | 3.2 | 1.6 | >50 | >200(est) |

| Virus Isolate | $EC_{100}$ | $EC_{90}$ | $CC_{50}$ | "SI" |
|---|---|---|---|---|
| N. American | 3.2 | 1.6 | >50 | >200(est) |
| European | 3.2 | 1.6 | >50 | >200(est) |

Incidence and Related Nidovirales

| Virus | Distribution | Incidence |
|---|---|---|
| Coronaviruses (refer to Bovine Coronavirus) | Worldwide | Endemic |

FIG. 43

Results of Rift Valley Fever Testing

In Depth Analysis

| | $CC_{50}$ | $EC_{50}$ | "SI" |
|---|---|---|---|
| RVFV | 10 μM | 0.37 μM | 30 |

Incidence and Related Bunyaviruses

| Virus | Distribution | Incidence |
|---|---|---|
| Rift Valley Fever | Subsaharan Africa | Low, periodic Outbreaks of 1M+ |
| Hantavirus | Worldwide | Low, periodic outbreaks |

Initial Assay RVFV

FIG. 44

Results of Marburg Virus Testing

In Depth Analysis

| | CC$_{50}$ | EC$_{50}$ | "SI" |
|---|---|---|---|
| MARV | 20 μM | 10 μM | 2 |

Incidence and related Mononegavirales

| Virus | Distribution | Incidence |
|---|---|---|
| Rabies | Worldwide | >60,000/yr |
| Measles | Worldwide | Rare; sporadic outbreaks |
| Paramyxo and Pneumoviruses (RSV, PIV, HMPV) | Worldwide | Endemic |

Initial Assay Marburg

FIG. 45

Coronavirus Inhibition

| Virus | Target Cell | $EC_{90}$ | $CC_{90}$ | "$SI_{90}$" |
|---|---|---|---|---|
| SARS-Urbani | Vero-76 | 0.30 μM | >1 | >3 |

| Virus | Target Cell | $EC_{100}$ | $EC_{90}$ | $CC_{50}$ | "$SI_{50}$" |
|---|---|---|---|---|---|
| Bovine Coronavirus | Marc-145 | 1.25 | 6.2 | >50 | >100(est) |

Incidence and Related Coronaviruses

| Virus | Distribution | Incidence |
|---|---|---|
| Human Coronavirus 229E (HVoV) | Worldwide | 43% of neonates in PNICU |
| SARS | Asia | Rare |

FIG. 48

510: Cell-Based Efficacy and Safety

| Virus | $EC_{50}$ (μM) | $CC_{50}$ (μM) | "$SI_{50}$" |
|---|---|---|---|
| RSV | 0.029 | 11 | 378 |
| PIV | 0.036 | 11 | 305 |
| Ebola | 0.012 | >8 | >600 |
| West-Nile | 0.12 | >50 | >400 |
| Lassa | 1.3 | >8 | >6 |
| HCV | 10 | >30 | >3 |

FIG.55

Hemorrhagic Fever Viruses

In Depth Analysis

| | CC$_{50}$ | EC$_{50}$ | "SI" |
|---|---|---|---|
| EBOV | >8 μM | 0.012 μM | >650 |

Incidence and Related Mononegavirales

| Virus | Distribution | Incidence |
|---|---|---|
| Rabies | Worldwide | >60,000/yr |
| Measles | Worldwide | Rare; sporadic outbreaks |
| Paramyxo and Pneumoviruses (RSV, PIV, HMPV) | Worldwide | Endemic |

Initial Assay
Inhibition of Infection

FIG.56

510 Activity Against Ebola in vivo

FIG. 63

Caspase Inhibition by 510 – IC$_{50}$ Determination

| Target | IC$_{50}$ ($\mu$M) |
|---|---|
| Casp-2 | 3.38 |
| Casp-3 | 2.77 |
| Casp-7 | 2.67 |
| Casp-8 | 2.67 |
| Casp-9 | 60.35 |
| B-Luc | >100 |

Yellow denotes the key hydrogen bonds formed by the amidines to the side chain carboxylate of Asp158 and the backbone carbonyl oxygen of Tyr273

METHODS OF INHIBITING VIRAL INFECTION

PRIORITY DATA AND INCORPORATION BY REFERENCE

This application claims benefit of priority to U.S. Provisional Patent Application No. 60/982,227 filed Oct. 24, 2007, which is incorporated by reference in its entirety. This application also incorporates by reference the entire disclosure of U.S. Patent Application Publication WO 2008/089125 A2 and the corresponding U.S. patent application Ser. No. 12/013,640.

GOVERNMENT SUPPORT

Work resulting in the invention disclosed and claimed herein was funded in part by U.S. Government Contract HDTRA1-07-C-0080, and the government may enjoy limited rights therein to certain applications pertaining to hemorrhagic fever virus treatment.

BACKGROUND OF THE PRIOR ART

Those of skill in the art have recognized that it would be desirable to identify agents that inhibit more than one specific viral agent, so that different viral infections could be inhibited with a single agent or family of agents. By the same token, it would be desirable to identify such as "pan viral" agent that did not put survival pressure on the virus itself, so as to avoid being be defeated by the frequent mutations exhibited by the viral population. Until now, given the extreme variety of viral infectious modes and characteristics across the various viral families, it has been difficult to establish a common therapy. One pathway, apparently mediated by TSG101, is the subject of ongoing studies. Inhibition via this pathway, however, is primarily based on the generation of selective antibodies, and no specific agent or composition has been identified to interfere with these pathways on a commercial basis. These efforts are discussed, inter alia, in U.S. Pat. Nos. 6,835,816 and 6,248,523.

Recently, a family of compounds were identified as having implications for anti-bacterial activity, and in particular, anti-botulism activity. These compounds are identified in U.S. patent application Ser. Nos. 11/464,001 and 11/464,007, both of which are incorporated by reference herein in their entireties. The compounds, per se, were originally identified in a screen for compounds having anti-tumor activity. It would be truly unusual if such compounds exhibited anti-viral activity as well as anti-bacterial activity. Recently, as described in 60/884,928, also incorporated by reference herein, two related compounds were indicated to have some ability to protect mice from challenge from Ebola virus. In the United States of America, and much of the rest of the world Ebola is a viral threat only in terms of a weapon deliverable, as in "germ warfare." The treatment of other virus infections by a limited class of therapeutic agents is yet to be established.

BACKGROUND OF THE INVENTION

1. Field of the Invention

The present invention relates to a set of compositions comprising a family of small molecules that are further effective at preventing, treating, and/or managing viral infection caused by a variety of virus types. The present invention further relates to methods of administration of compositions of the present invention to a patient, human or animal experiencing or at risk of viral infection as well as methods for screening additional compounds to identify related inhibitors that are further effective at inhibiting viral infection. This invention also offers a possible fundamental biological activity pathway for the inhibition of viral infection, by identifying a possible mode of action (MOA) of the studied compounds, and others, as selective Caspase inhibitors.

2. Related Art

Viruses have long been known to be the causative agent in a wide variety of human and animal infectious diseases associated with human and animal morbidity and mortality. Many different viral pathogens have consistently caused debilitating or fatal diseases in humans and animals (e.g., influenza, etc.) while others are emerging or re-emerging (e.g., HIV, West Nile virus, SARS, etc.).

Efforts to treat or prevent viral infection in both animals and humans may be generally classified into two broad categories: vaccines and antiviral drugs. Vaccines generally work by priming the immune system of an individual through administration of an immunogen. The immunogen is typically a killed virus, an attenuated virus, or a viral subunit that is incapable of causing infection but is sufficient to trigger an immune response. Since the immunogen resembles the live virus targeted by the vaccination, the immune system is able to readily identify and eliminate the virus during early stages of actual infection. When available, vaccines are very effective at immunizing individuals against particular viruses that cause disease.

However, vaccines are often limited in that they are generally only effective in immunizing individuals prior to infection (i.e., they are ineffective as a means for treating infected individuals that may or may not yet be experiencing symptoms of disease). Furthermore, vaccines are often ineffective in vaccinating individuals against viruses that are highly mutable since these viruses are able to evade any immunity generated by vaccination.

Research has also focused on developing antiviral medications as a means for treating individuals who are already infected as well as treating or preventing viral disease where vaccination methods are seen as unavailable or unlikely. Such approaches toward developing antiviral medications have generally sought to identify molecules or drugs that interfere with the basic mechanisms or steps of viral infection, through what is called "rational drug design." Alternatively, antiviral drugs, such as interferons or antibodies, may instead be designed to broadly stimulate the immune system against a range of pathogens.

In general, viruses proceed through a series of steps akin to the following during their normal infection cycle: (1) attachment (i.e., specific binding between viral capsid or coat proteins and receptors on the host cell surface), (2) penetration (i.e., entry into the host cell generally through endocytosis or membrane fusion), (3) uncoating (i.e., digesting or degrading the viral coat to allow the contents and viral genome to be released into the cell), (4) replication and assembly (i.e., the synthesis of new viral proteins and DNA/RNA, including intermediates, necessary to form new virus particles), (5) maturation (i.e., post-translational modification and processing to form mature virus particles), and (6) release or budding (i.e., freeing the virus particles to infect new host cells). However, not all viruses proceed through all of these steps in the manner summarized. For example, HIV undergoes maturation after being released from the host cell.

Despite noted success in the design and development of novel antiviral drugs in recent years, including the development of protease inhibitors, existing therapies are limited in terms of the number and breadth of viruses that they may be used to treat. In addition, many strains of viruses have become resistant to antiviral drugs as a result of mutation of their viral genomes. Accordingly, there continues to be a need in the art for the development of new classes of antiviral drugs to treat or prevent viral disease, especially those that show promise against a variety of virus types. There also continues to be a need in the art for the development of novel antiviral drugs that are effective against highly mutable viruses that are generally capable of evading treatment via existing vaccines and drugs.

Subsequent to the effective filing date of this application, a broadened description of the effectiveness of the family of compounds addressed in provisional U.S. Patent Application 60/884,928 was presented in U.S. patent application Ser. No. 12/013,640. Applicants have further expanded the range of activities, mechanisms and family of compounds that offer activity against one or more viruses and viral families. At the time of filing this Application, the assignee of this application, Functional Genetics, Inc. is the exclusive licensee of U.S. patent application Ser. No. 12/013,640.

SUMMARY OF THE INVENTION

The compounds identified as effective against viral infection in mammals are drawn from the broad class of compounds previously identified in U.S. Ser. No. 60/884,928 and Ser. No. 12/013,640. As set forth in the detailed description of this invention, additional information has been developed that allows identification of a more limited family based not only on structural similarity, but on activity. Activity of compounds is demonstrated herein by both in vitro methods, largely reflected as cell based assays, and in vivo experimentation, largely involving challenge based methodologies. Tolerance for these molecules, as well as general levels of effectiveness are also given.

Specifically, the compounds of the present invention are drawn from the family of compounds described by the following structural formula:

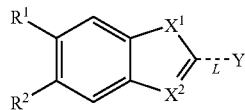

where Y is

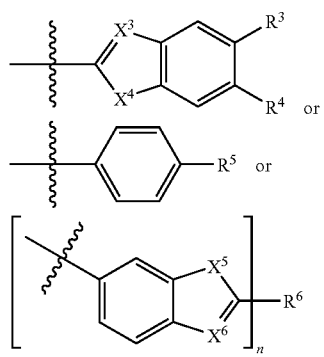

Wherein
n is 1 or 2;
$X^1$, $X^2$, $X^3$, $X^4$, $X^5$ and $X^6$ are each independently N, S, O, $SO_2$, $CR^7$ or $NR^8$ and at least one of $X^1$, $X^2$ is N, S, O, $SO_2$ or $NR^8$;

L is a linker which may be a direct bond or

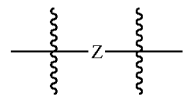

where Z is an optionally substituted alkyl, alkenyl, dialkenyl, trialkenyl, or aryl, or C(O)NH; and $R^1$, $R^2$, $R^3$, $R^4$, $R^5$, $R^6$ and $R^7$ are each independently hydrogen, amino, amine with stabilized carbocations, carboxyl, optionally substituted alkyl, alkenyl, alkynyl, cycloalkyl, heterocycloalkyl, aryl, heteroaryl, alkoxy, aryoxy, cycloakloxy, heteroaryloxy, aloxycarbonyl, alkylamino, carbornoyl, alkylaminocarbonyl, alkysulfhydryl, alkylhydroxymate;

$R^8$ is hydrogen, OH, a halogen, or an optionally substituted alkyl;

In some embodiments, at least one of $R^1$, $R^2$, $R^3$, or $R^4$ is hydrogen, amidine, 2-imidazoline, amino, guanidine, methyl, aminomethyl-hydroxamine, or methylamine-guanidine. In some embodiments, $R^5$ is hydrogen, amidine, 2-imidazoline, amino, guanidine, methyl, aminomethyl-hydroxamine, methylamine-guanidine, 4-oxy-benzamidine, 1H-indole-6-caboxamidine, or 1H-indole-5-carboxamidine. In some embodiments, $R^6$ is hydrogen, amidine, benzamidine, benzimidazoline, imidazoline, guanidine, imidazole, oxazole, benzofuran-2-yl-imidazoline, benzofuran-2-yl-amidine, benzofuran-2-yl-guanidine, benzothiophene-2-yl-imidazoline, benzothiophene-2-yl-amidine, benzene-2-yl-amidine, benzofuran-2-yl-imidazole, or benzofuran-2-yl-oxazole. In some embodiments, at least one of $X^1$ or $X^2$ is N, NH, S, O, $SO_2$, CH, C—$CH_3$, C-phenyl, N-ethanol, N-chloroethyl, C-amino, C-(2-indole-6-imidazoline), C-(2-indole-6-amidine), C-(2-indole-5-imidazoline), or C-(2-indole-5-amidine). In some embodiments, at least one of $X^3$, $X^4$, $X^5$, or $X^6$ is N, NH, S, O, $SO_2$ or CH. In some embodiments, least one of $R^1$, $R^2$, $R^3$, $R^4$, $R^5$, $R^6$, or $R^7$ is —H, —$CH_3$, —$NH_2$,

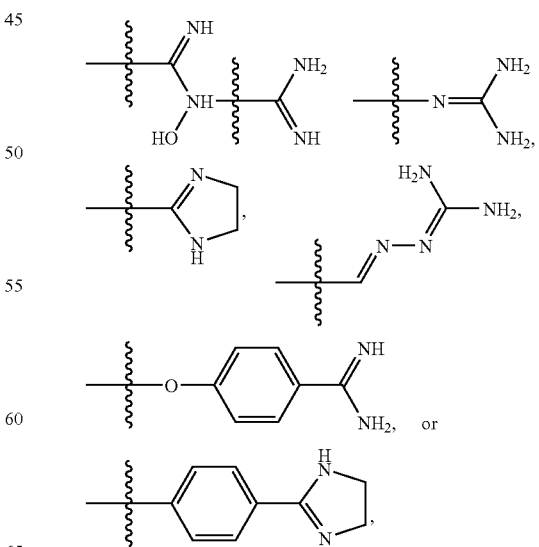

In some embodiments, $R^5$ is

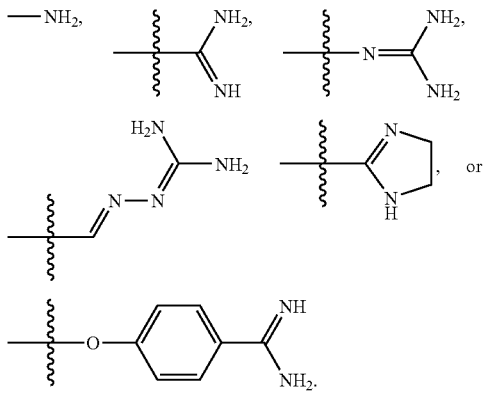

In some embodiments, $R^6$ is

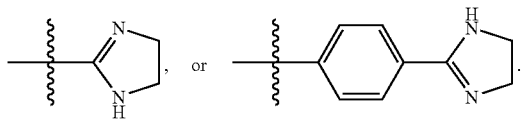

In some embodiments, $R^7$ is —H, —CH$_3$, —NH$_2$,

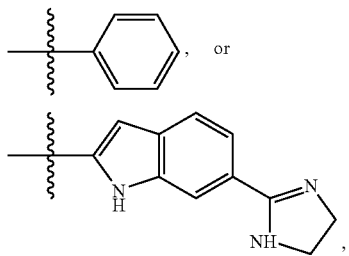

In some embodiments, $R^8$ is —H, —(CH$_2$)$_2$OH, or —(CH$_2$)$_2$Cl. In some embodiments, L is a direct bond,

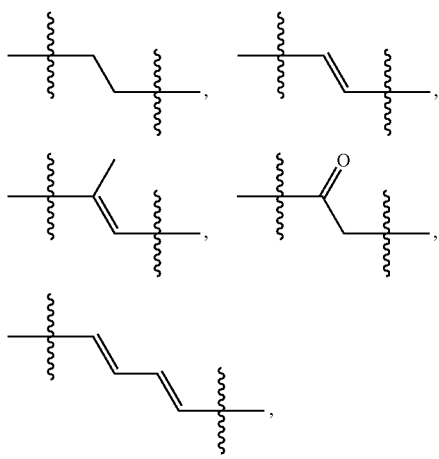

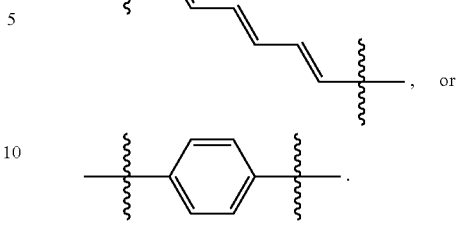

In some embodiments, the compound has the following structural formula:

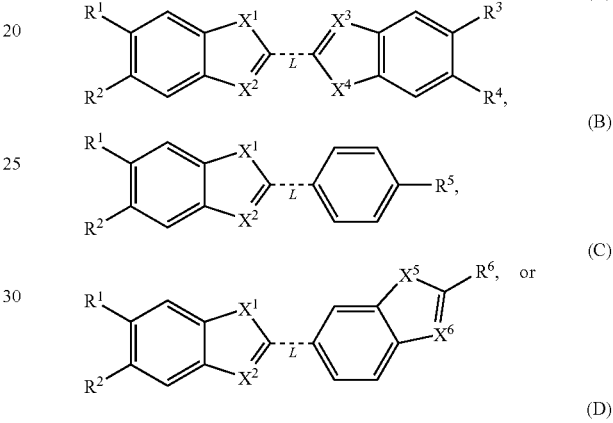

Compounds of particular interest include NSC compounds 369723, 294199, 306365, 300510, 294206 and 294202, as well as Compounds 50410 and 50413. Collectively, these, and the compounds set forth in FIGS. 6A-6C, and the related family of compounds, are referred to herein as FGI-103 compounds. The chemical formulae of these compounds are given in FIGS. 1-4 and ˆA-6C, with an assessment of common structural units presented in FIG. 5. Activity is not confined to these compounds, however, and a list of active compounds of similar structure is provided. This list allows the identification of tentative structural formulae that provide enhanced guidance on selection.

This application involves extensive data, as is appropriate for a patent application directed to a family of compounds that exhibit activity against multiple families of viruses. The application bears a distinct organization. Below are described a number of Figures that provide certain structural information, followed by activity information for each of the three most tested compounds. The detailed description of this application parallels these Figures, devoting attention to the class collectively, and then the studied performance of each of three different active compounds. Following that, common activity of the compounds in terms of fundamental biological pathways, as well as routes of administration and effectiveness, are presented. Thereafter the claims are presented.

BRIEF DESCRIPTION OF THE DRAWINGS

This invention is described by reference to drawings and figures set forth in the application as originally filed, discussed hereinbelow. The drawings are briefly described below:

FIGS. 6A-6C list some of the 27 compounds of the methods of this invention that have been demonstrated in cell based assays to exhibit viral inhibition activity against at least Ebola virus and/or monkey pox.

FIG. 7 gives some evidence for the mode of action of the FGI-103 family of compounds collectively, schematically and graphically, suggesting that the compounds of this family block viral particle assembly.

FIG. 12 displays a graph of 4 of the compounds of the FGI-103 family and their activity in a cell based assay against cowpox virus. The fundamental parameters for this and for all assays are given in the lower left corners of the Figures.

FIG. 13 shows activity for two of the FGI-103 compounds most studied, 723 and 365, against porcine reproductive and respiratory syndrome disease (PRRS) a commercially critical virus that devastates pig stocks worldwide.

FIG. 14, like FIG. 13, presents by table the effectiveness of the FGI-0103 compounds in the treatment of not only human viruses, but animal viruses as well. IN particular, mammals are subject to bovine corona virus, addressed in FIG. 14.

FIG. 15 reflects in vivo activity for two compounds of the FGI-103 family addressed by this invention, showing protection in mouse from Ebola challenge.

FIG. 17 again demonstrates the relative activity of a family of FGI-103 compounds against cowpox, in a mouse challenge. Importantly, FIGS. 15-17 reflects not only therapeutic activity, but prophylaxis for the tested compounds, administration having been given at or before the time of challenge, as well as after.

FIG. 18 is a table intended to provide in a single glance an index of the wide range of activity and applicability of these compounds, having been tested against Ebola, Marburg, Influenza, Lassa Fever, Rift Valley Fever, Cowpox, PRRS, Dengue Fever and HIV. These of course, as shown by the preceding figures and the figures to follow are not the only viruses against which these molecules are effective, but represent a common table.

FIGS. 19-36 reflect testing of one of the most active of the FGI compounds, compound 723. Thus, FIG. 19 is a tabular presentation of some of the most important datapoints for this compound. The presentation also includes suggested mechanism of action.

FIG. 20 provides data comparing viral titer reductions achieved at specific values, and related safety information, based on cell based assays. Throughout this application, the term $SI_{50}$ is used to denote Safety Index, and is obtained by dividing the $EC_{50}$ value by $CC_{50}$.

FIG. 21 presents in graphs and tables the results for cell based assays using 723 as the active agent against Paramyxoviruses including Parainfluenza and Respiratory Syncitial Virus.

FIG. 22 presents in graph and table more information on a cell based assay involving 723 against Hepatitis B virus (HBV).

Figure 23:
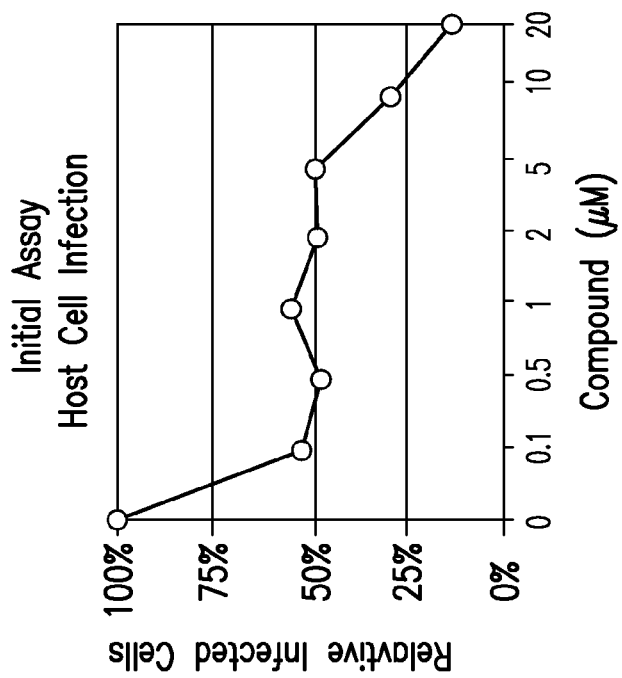

The same type of information is given in FIG. 23, which presents the results of protection provided by 723 in a cell based assay against Dengue fever, another recognized "bioterrorism threat" virus as well as an international scourge.

FIG. 24 presents information on cell survival against challenge from Ebola virus and Marburg virus, using 723 as the active protective compound. As shown, at low values of the active compound, 100% inhibition is achieved.

Figure 25:
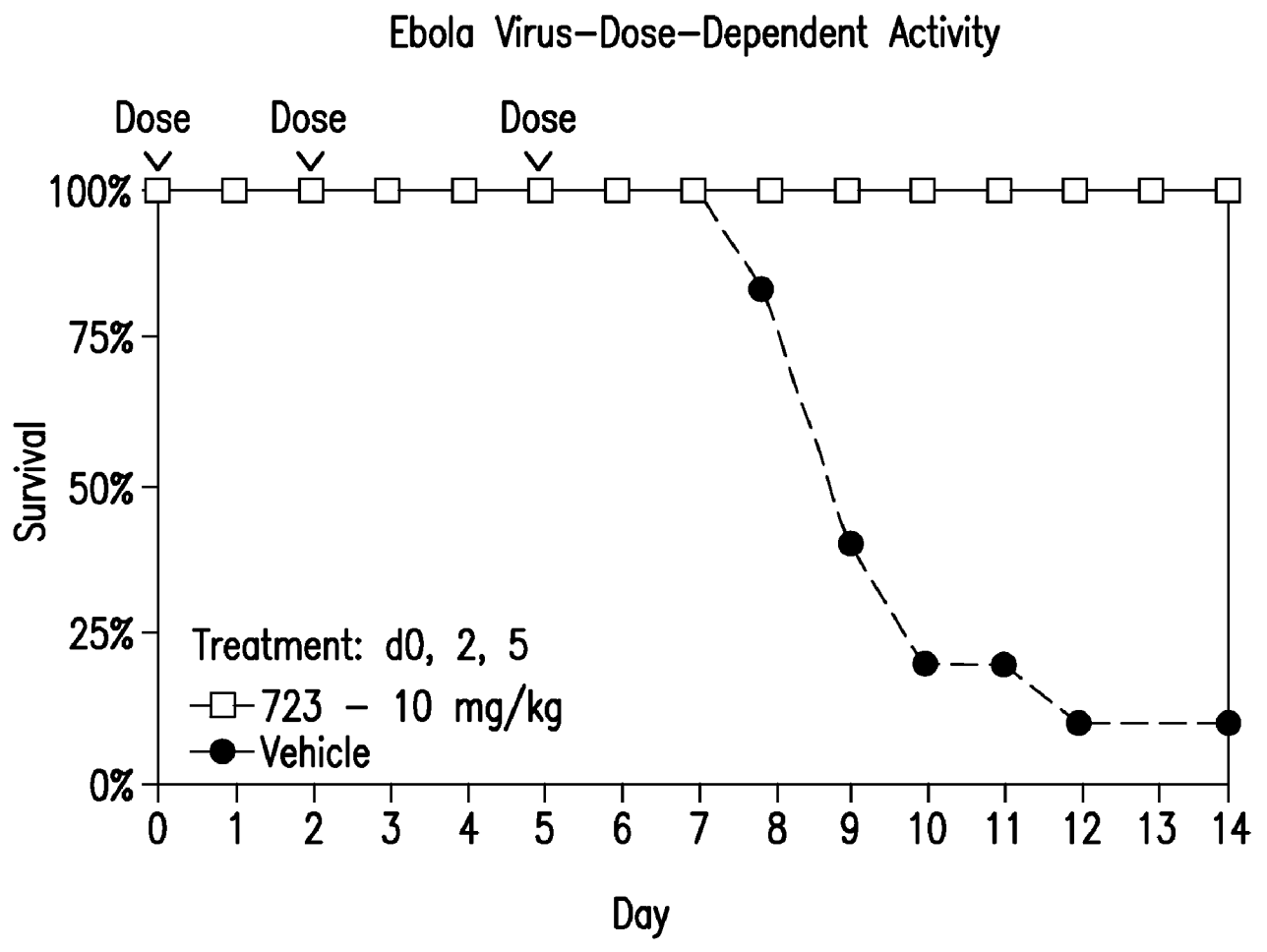

FIG. 25 reflects, in graph form, in vivo protection against Ebola virus. In this assay, 100% protection against Ebola challenge was provided in mice by 723.

FIG. 26 also portrays the results of in vivo testing of 723 against Ebola virus, this time in therapeutic measure only, the dose being administered after infection.

FIG. 27 provides graphic information on the result of administering 723 to mice 4 days after Ebola infection.

Figure 28:
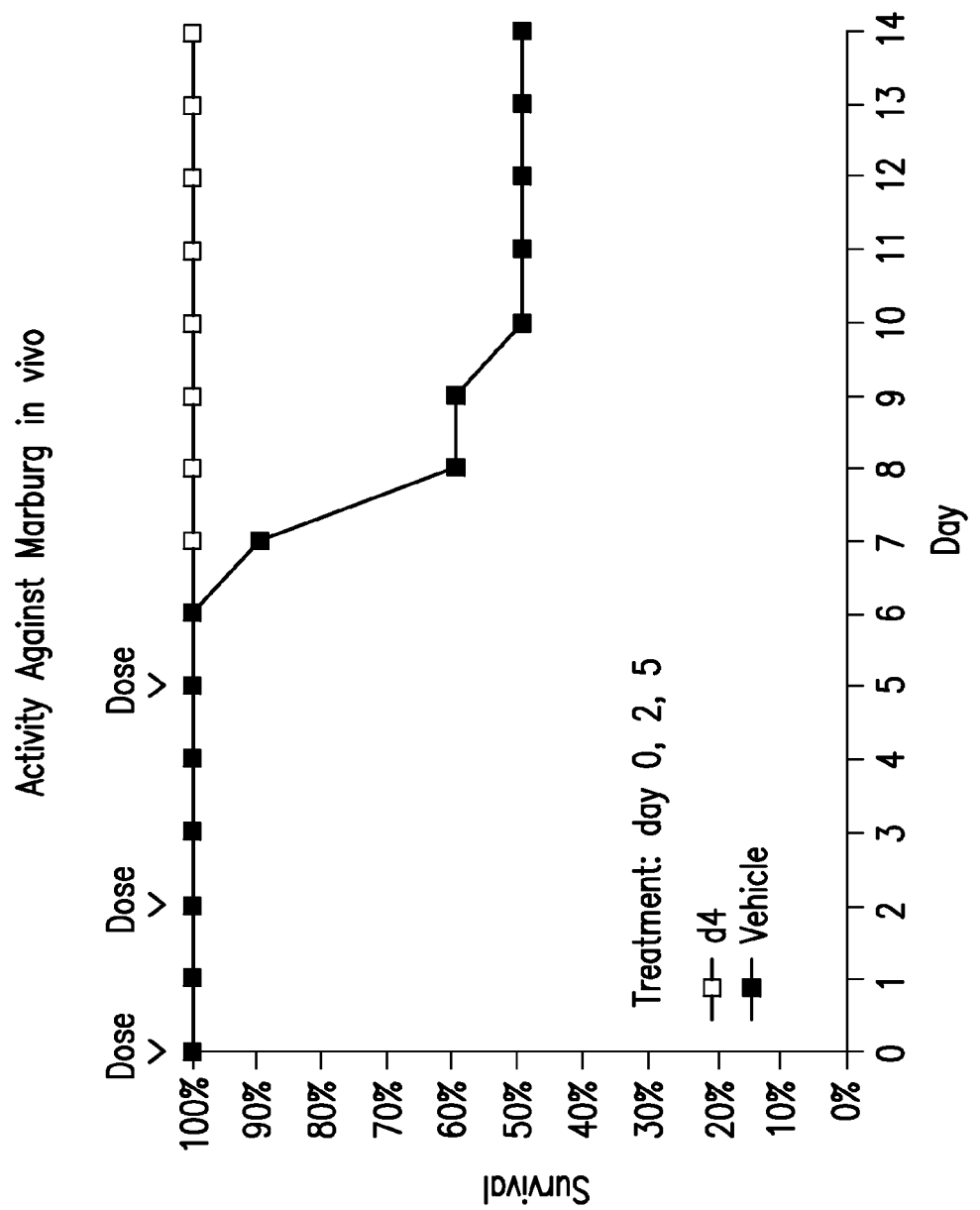

Protection against Marburg virus challenge, in vivo, is set forth in FIG. 28.

Figure 29:
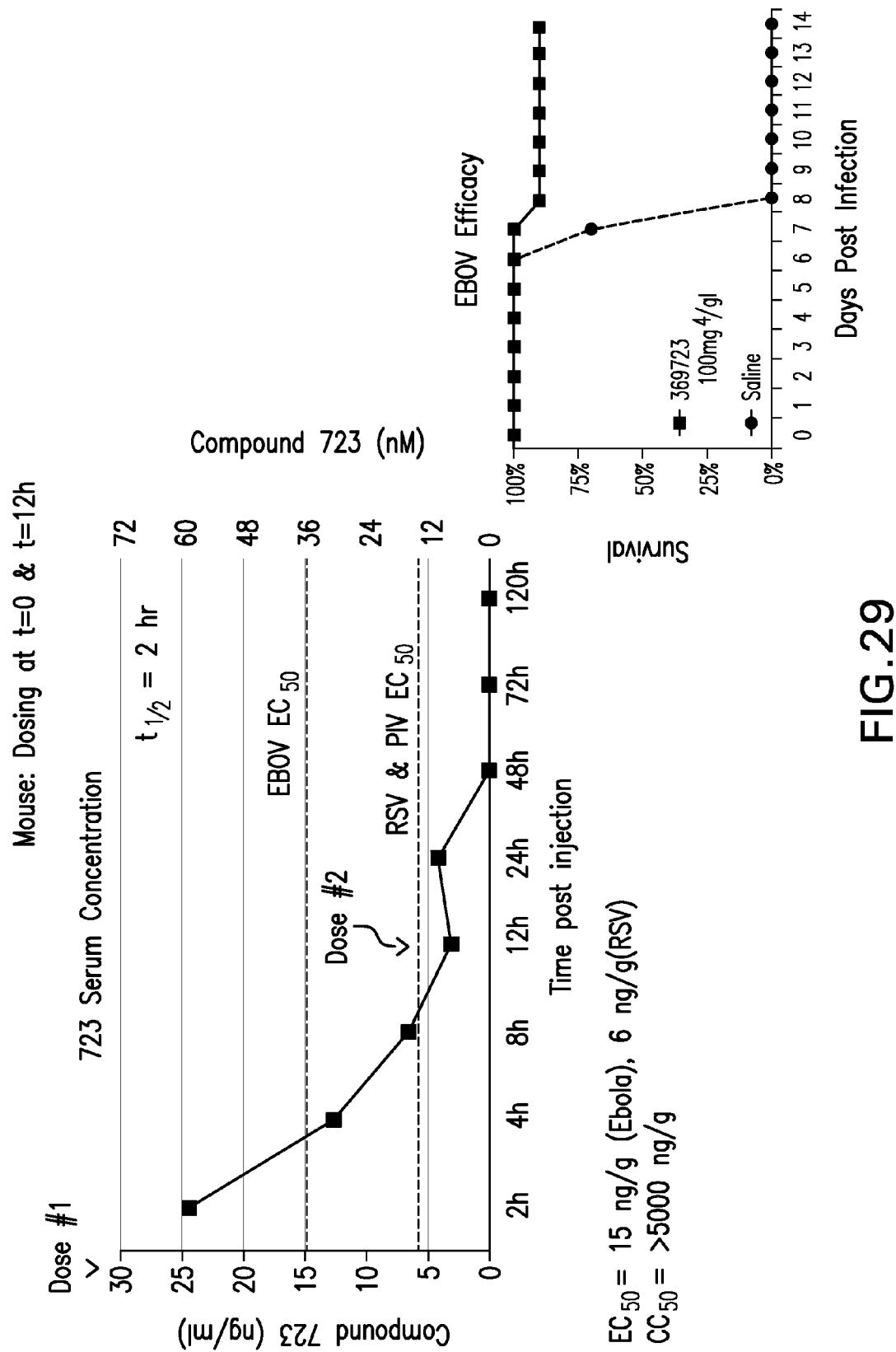

FIG. 29 reflects the serum levels of 723 following IP administration.

Figure 30:
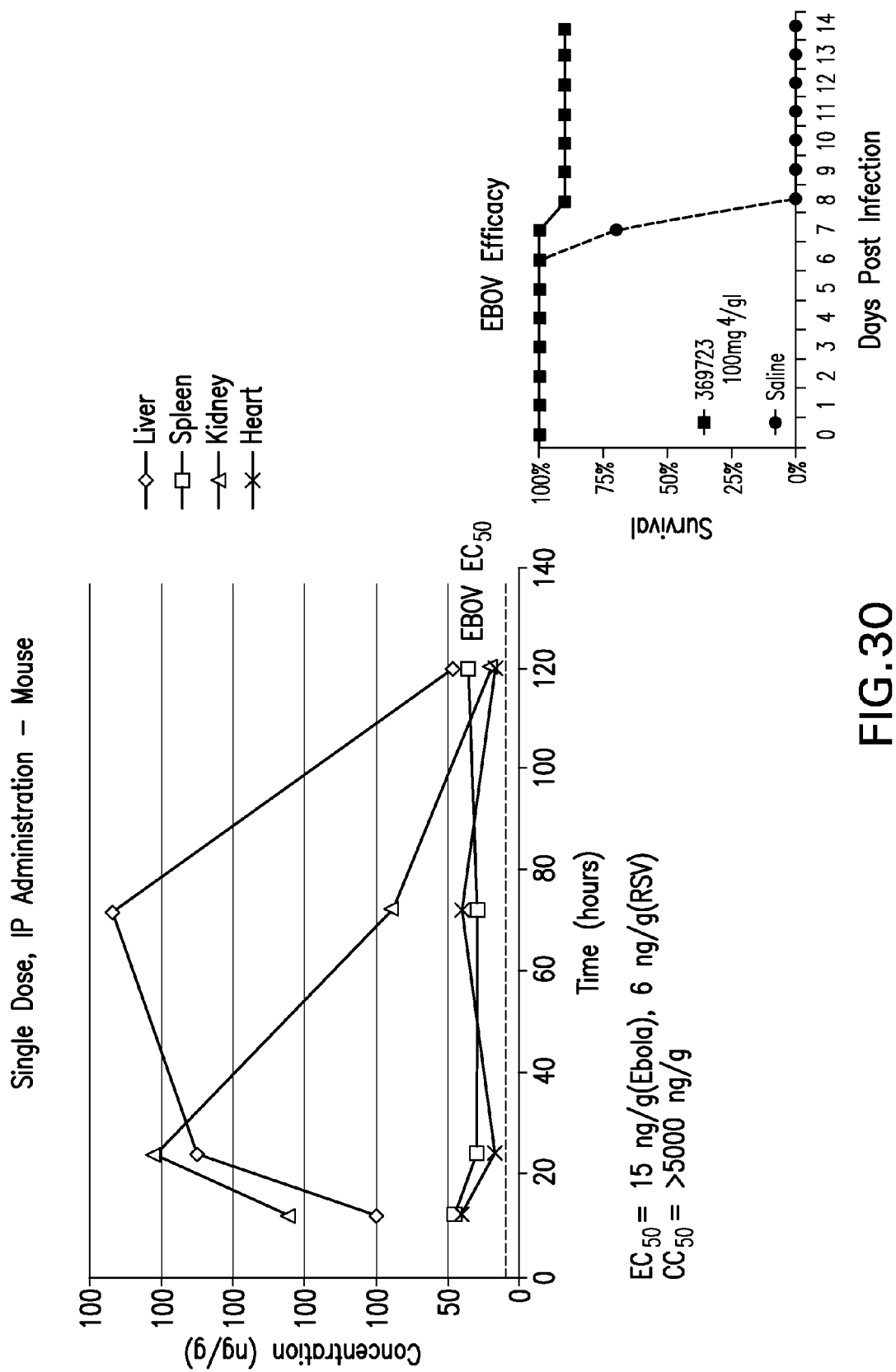

FIG. 30 presents information in graph form on the concentration of 723 in various body tissues at times following IP administration.

Figure 31:
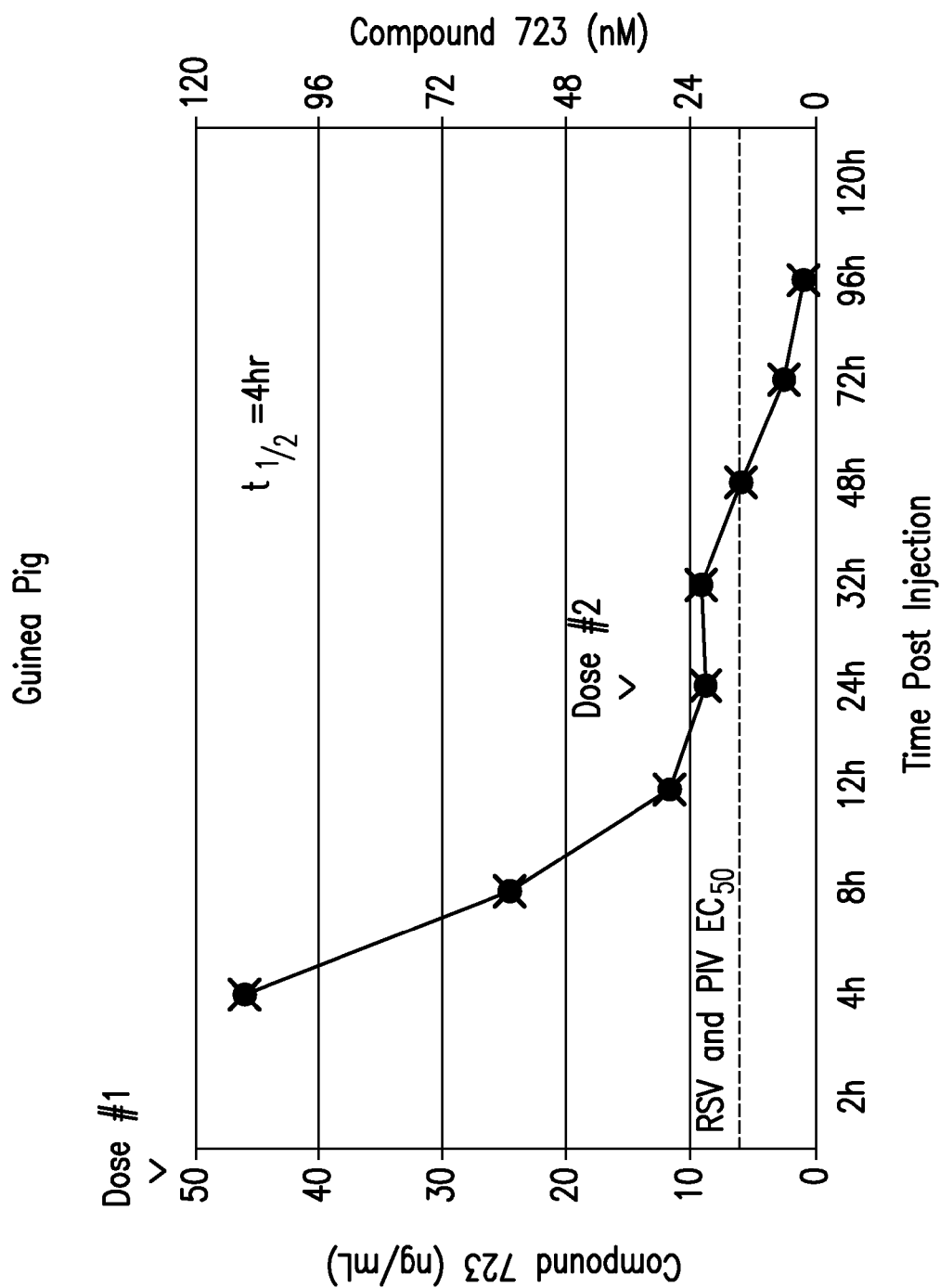

FIG. 31 gives similar information in graph form for serum concentrations of 723 in guinea pigs, post-administration, compared against the $EC_{50}$ value for these diseases, over time.

Figure 32:
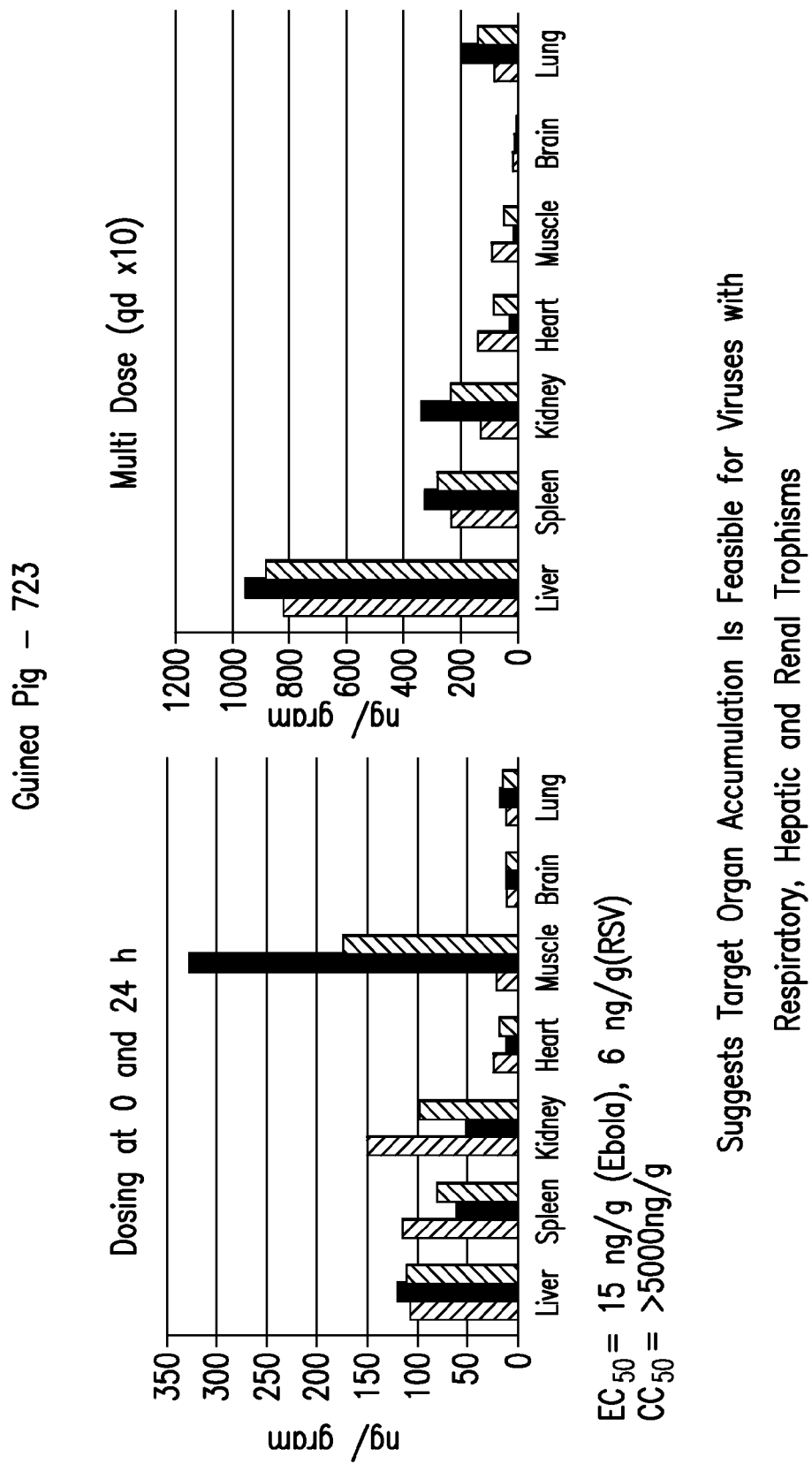

FIG. 32 provides, in bar graph form, information on the concentration of 723 in various tissues following single or multiple administration.

FIG. 33 provides bar graph information of drug availability following oral administration of a 723 "prodrug."

FIG. 34 provides, at a glance, in table form, safety information for a variety of cell types when treated with 723. As indicated, given the nature of some of the viruses involved, certain of these assays were conducted in the Biological Safety level four laboratories of USAMRIID in Frederick, Md. (Fort Detrick).

Figure 35:
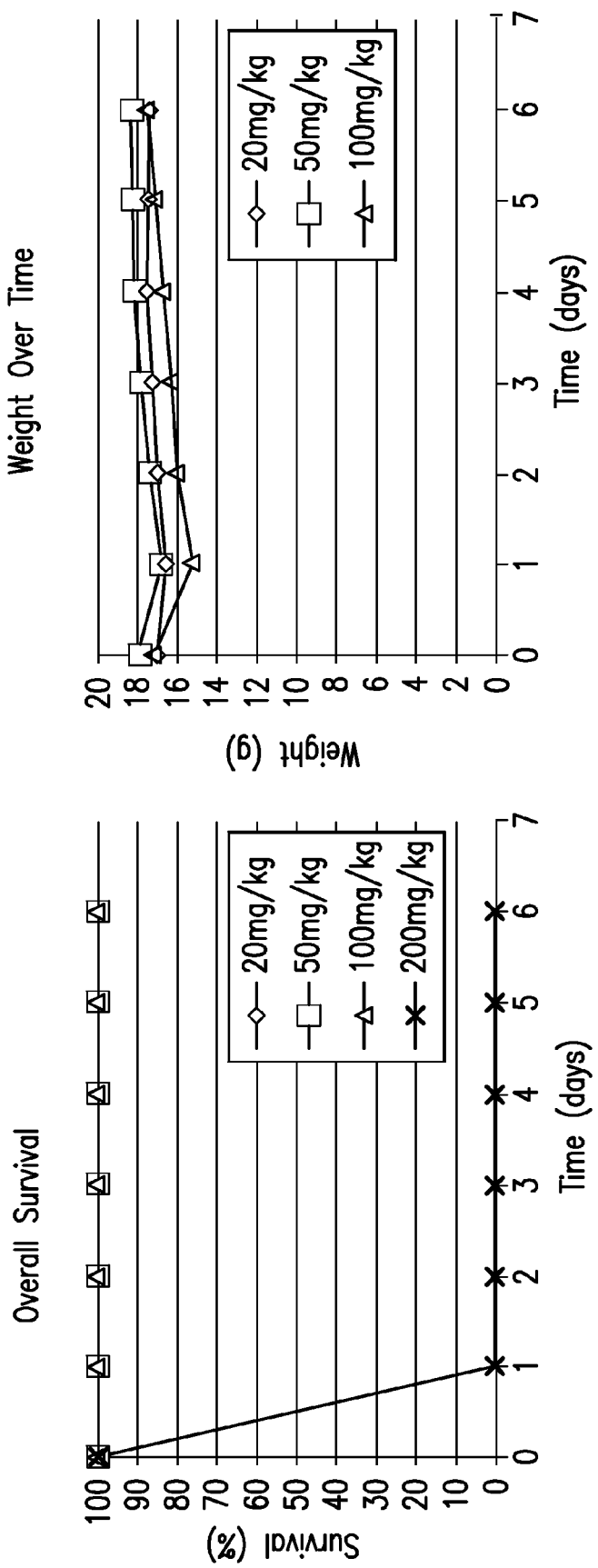

FIG. 35 provides safety/toxicity information on 723 as an agent or drug, in vivo.

Figure 36:
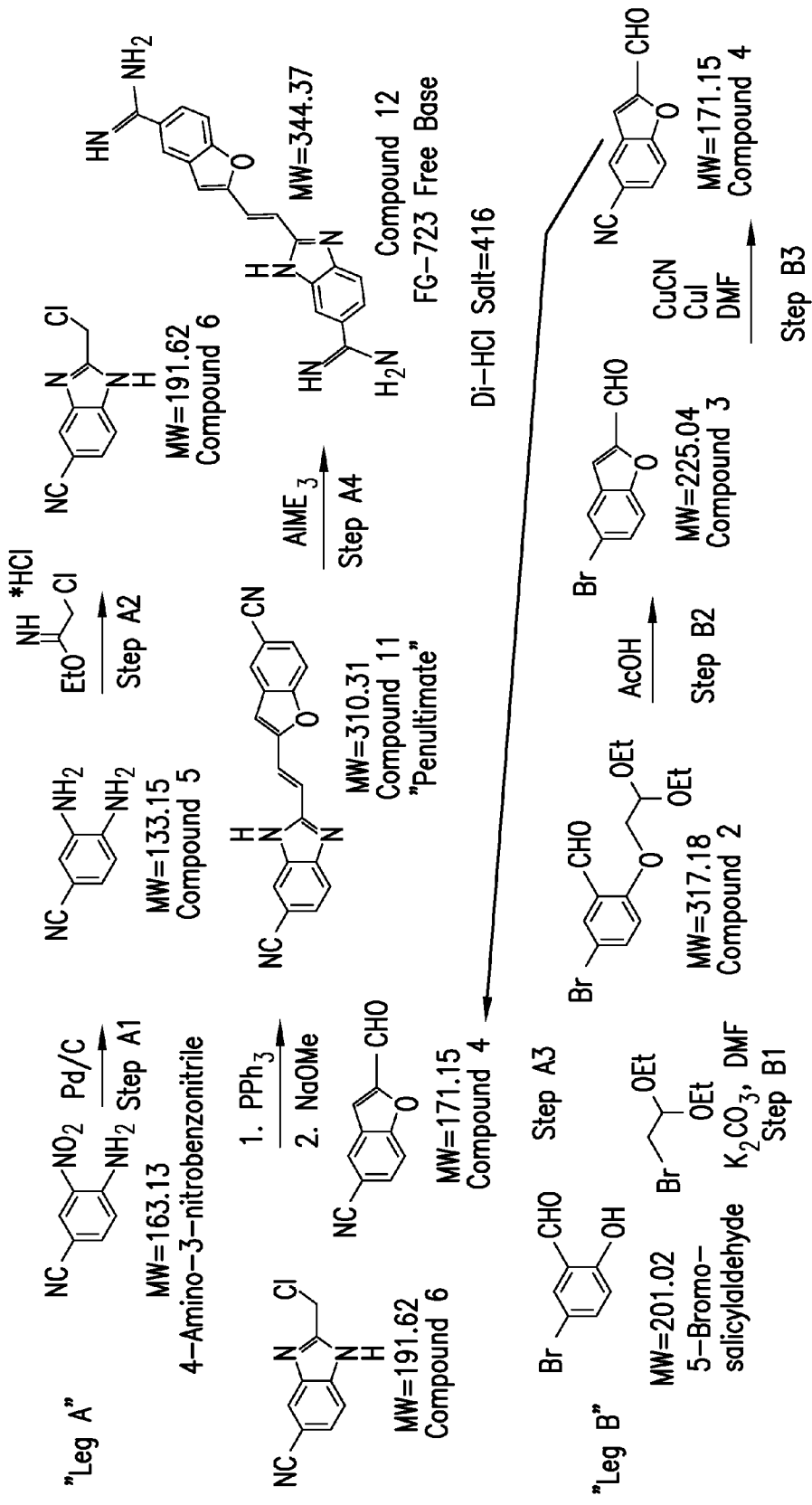

FIG. 36 provides a synthetic scheme for the manufacture of FGI-103 compound 723 according to good laboratory practice standards.

FIGS. 37-53 are directed to testing of another compound of the FGI 103 family—the compound referred to as 365. FIG. 37 is a tabular presentation of some of the most important datapoints for another of the FGI-103 compounds. The presentation also includes suggested mechanism of action.

FIG. 38 provides, in tabular form, a summary of the activity for compound 365 against a variety of viruses, those that afflict animals as well as humans.

Figure 39:
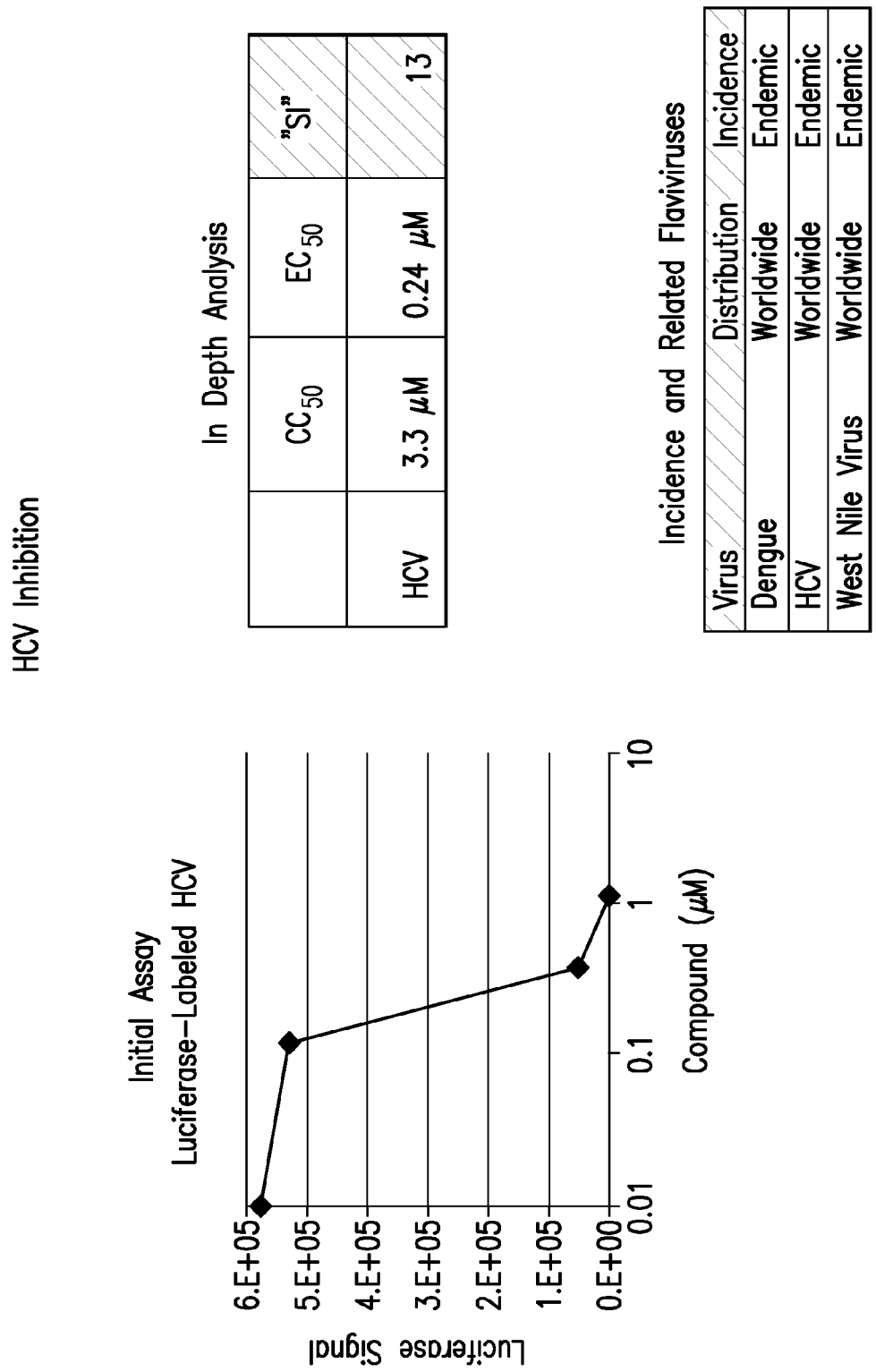

FIG. 39 reflects the effectiveness of Compound 365 in inhibiting Hepatitis C Virus, measured as the level of detected luciferase.

Figure 40:
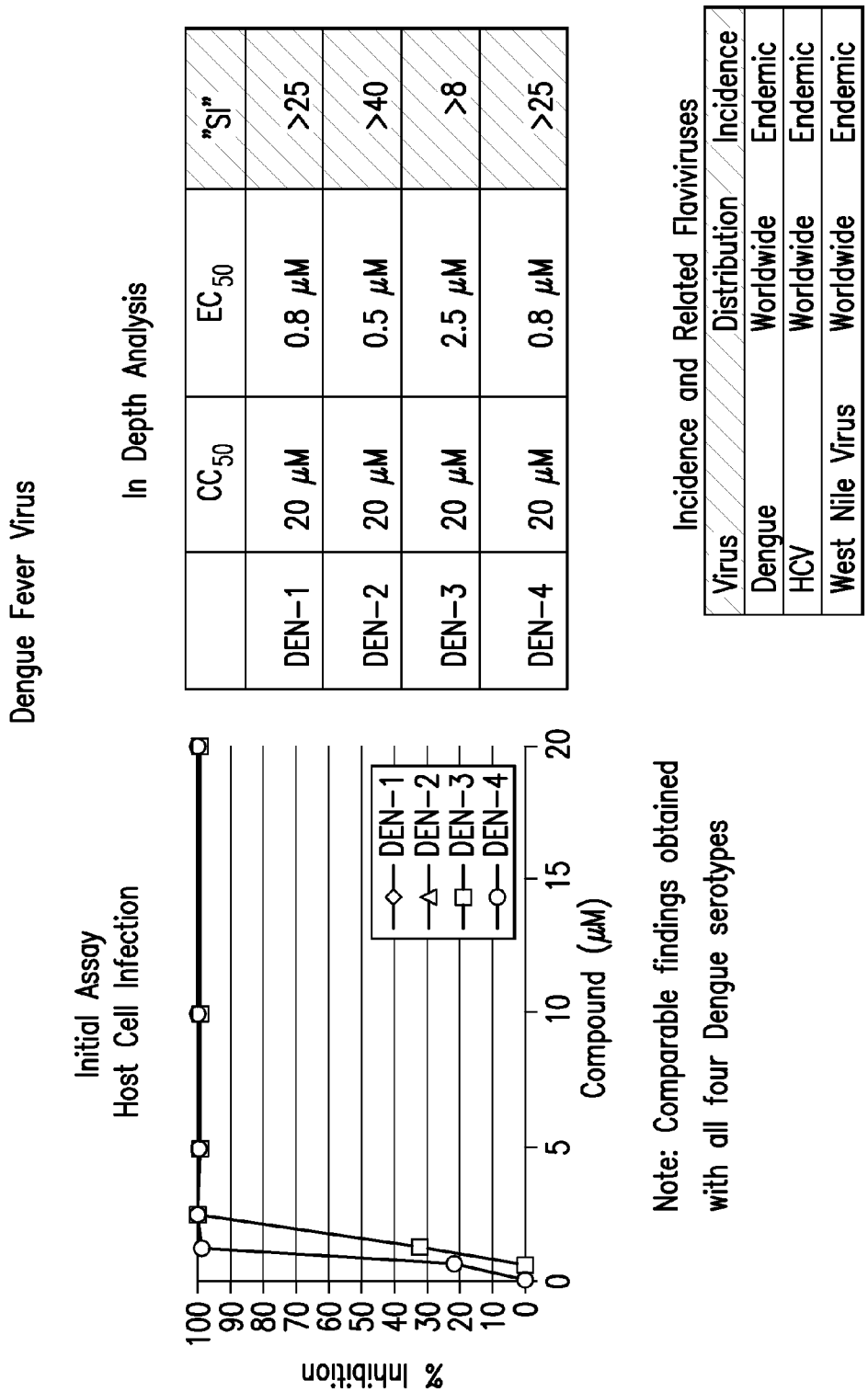

FIG. 40 presents in graph and table the results of a cellular assay showing the protection provided by Compound 365 against infection by all serotypes of Dengue Fever.

Figure 41:
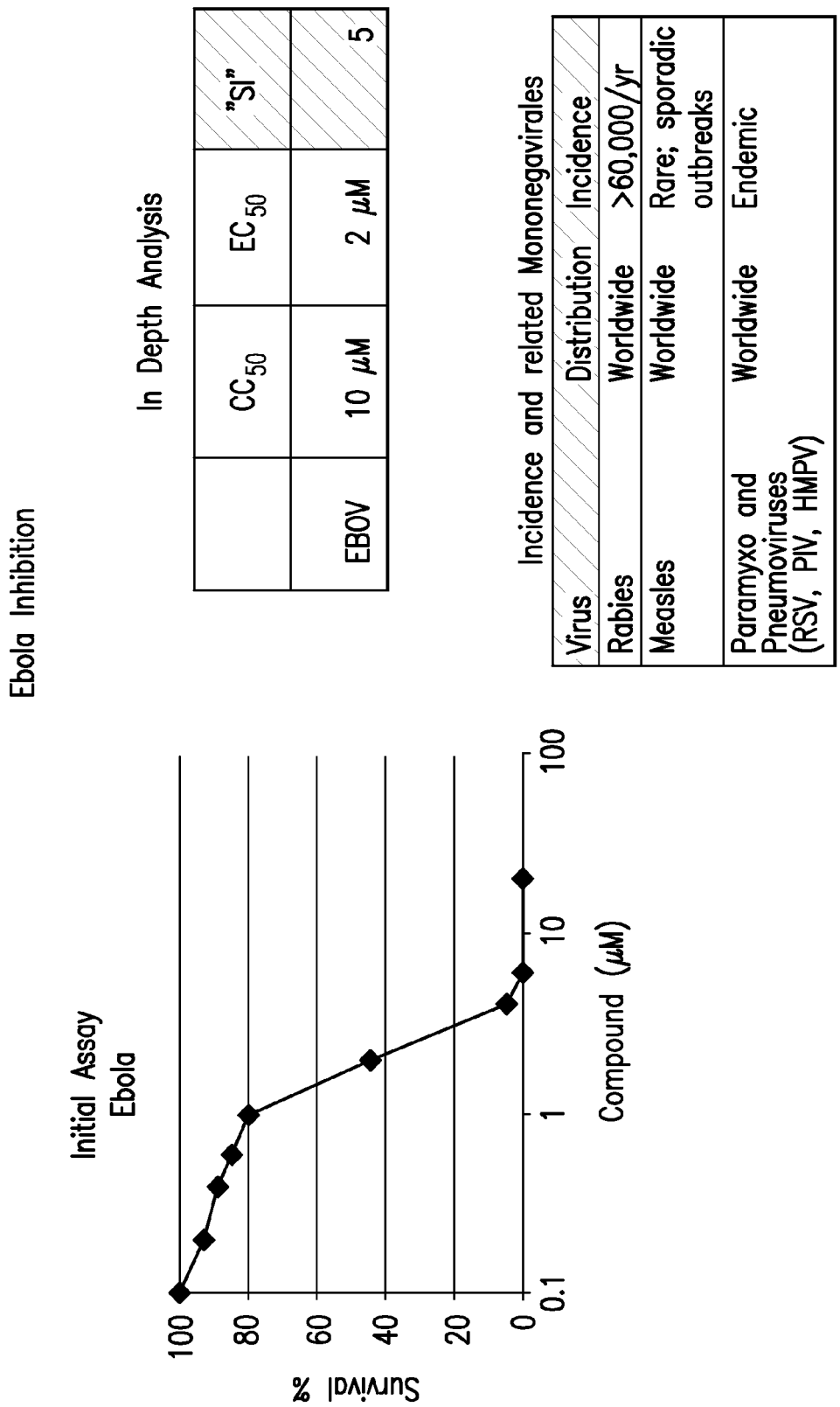

FIG. 41 displays by graph and table the data obtained by using 365 against an Ebola challenge in a Vero cell based assay.

Figure 42:
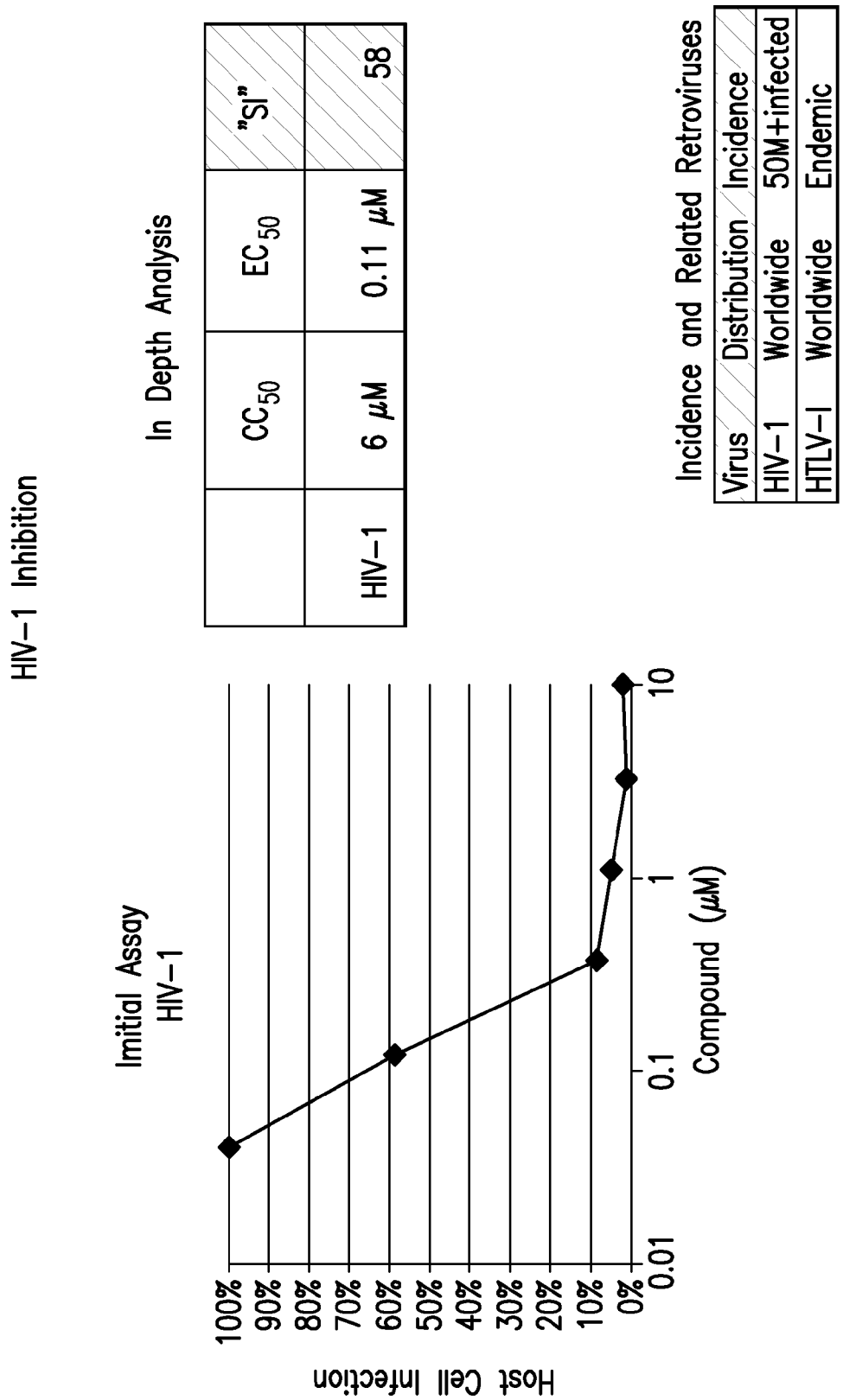

FIG. 42 displays by graph and table the inhibition of HIV infection in MT-4 cells.

As noted above, PRRS virus is commercially critical virus, plaguing pig populations around the world. FIG. 43 provides in tabular form information showing the inhibition of PRRS virus by Compound 365.

FIG. 44 presents in both graph and table form the results of testing 365 to inhibit Rift Valley Fever virus in a cellular (Vero cell) assay. In FIG. 44, as in many of the figures of this application, information regarding the distribution of the tested virus, and related viruses, is provided in the lower right corner.

FIG. 45 again looks at a cellular assay measuring the ability of 365 to inhibit Marburg Virus.

Figure 46:
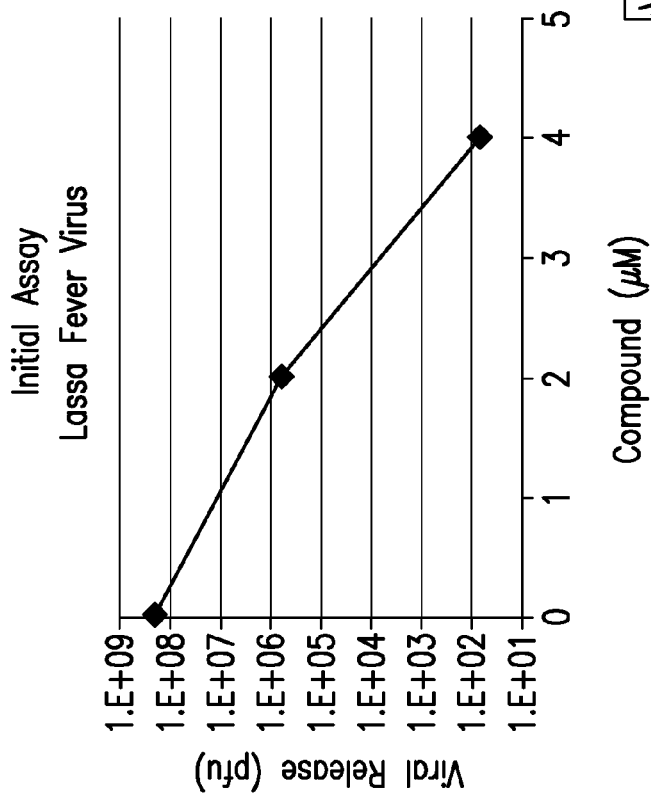

FIG. 46 shows, by graph and table, the effectiveness of Compound 365 in inhibiting infection by Lassa Fever Virus in a Vero cell assay.

FIG. 47 demonstrates, by table, that 365 is effective in inhibiting the activity of both SARS, a virus shown to be difficult to control, and Bovine Corona virus, another important livestock disease.

Figure 48:
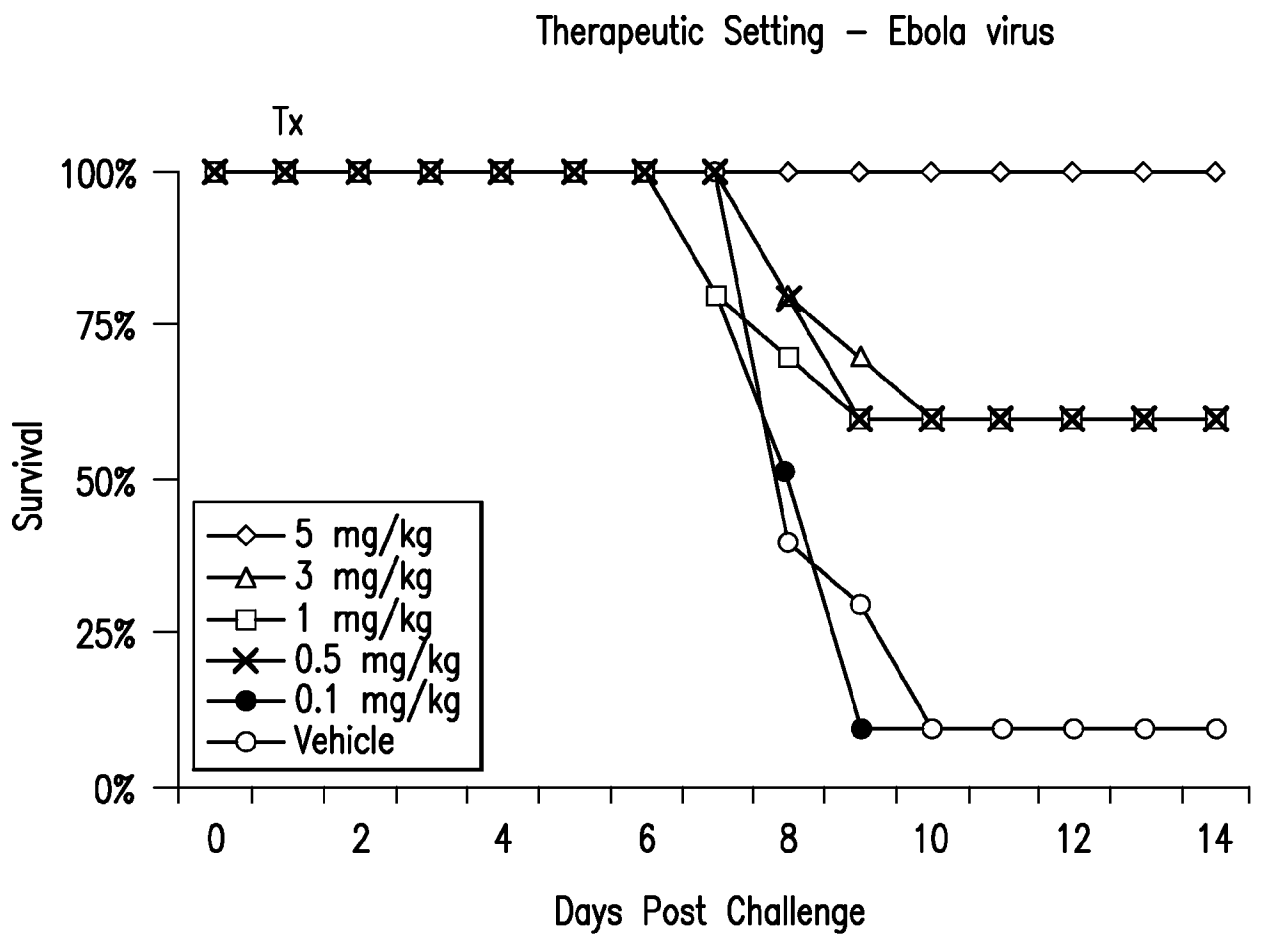

Like 723, Compound 365 has been tested in vivo as well as in vitro. FIG. 48 is a graph presentation of data obtained by using 365 in mice in a therapeutic mode against Ebola Virus. In a therapeutic mode, the administration occurs after challenge.

Figure 49:
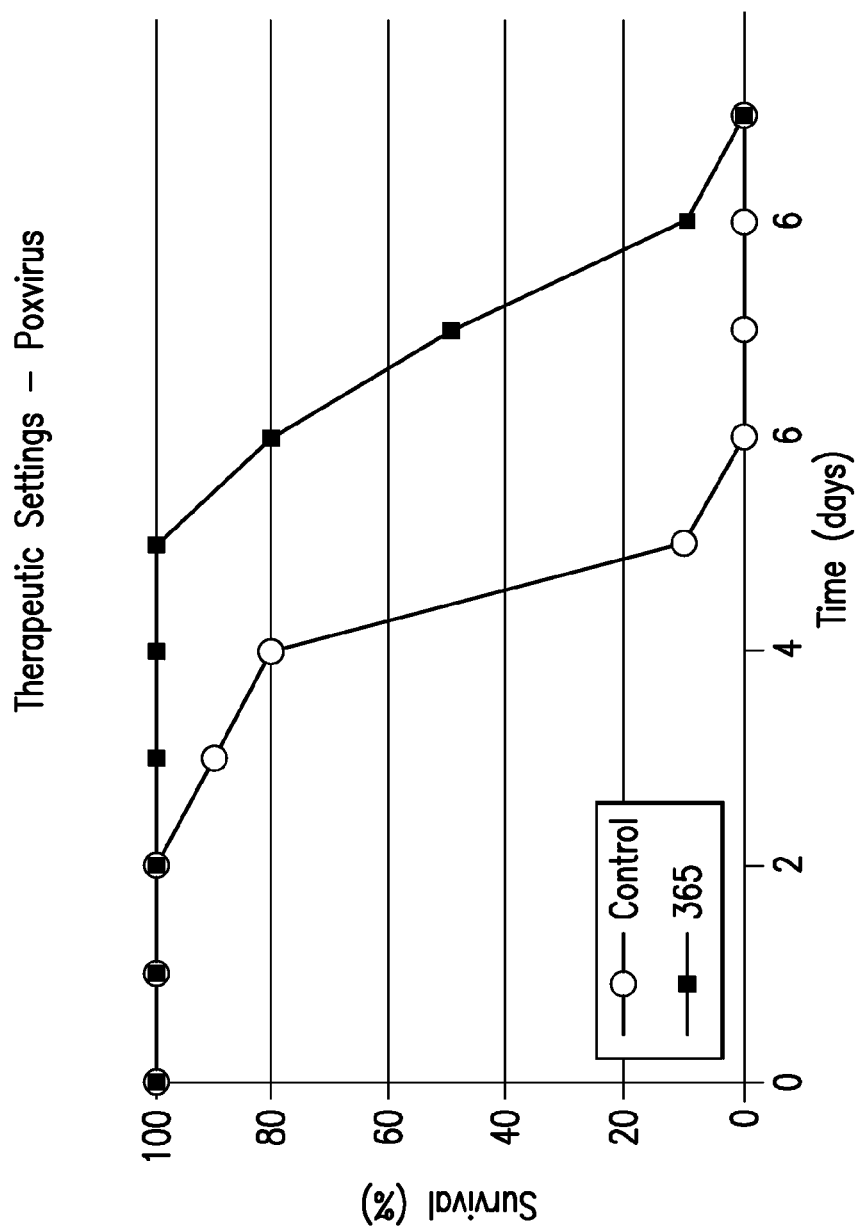

FIG. 49 shows the extension in survival conferred by administration of cowpox virus using 365, in vivo, as a therapeutic agent for mice.

Figure 50:
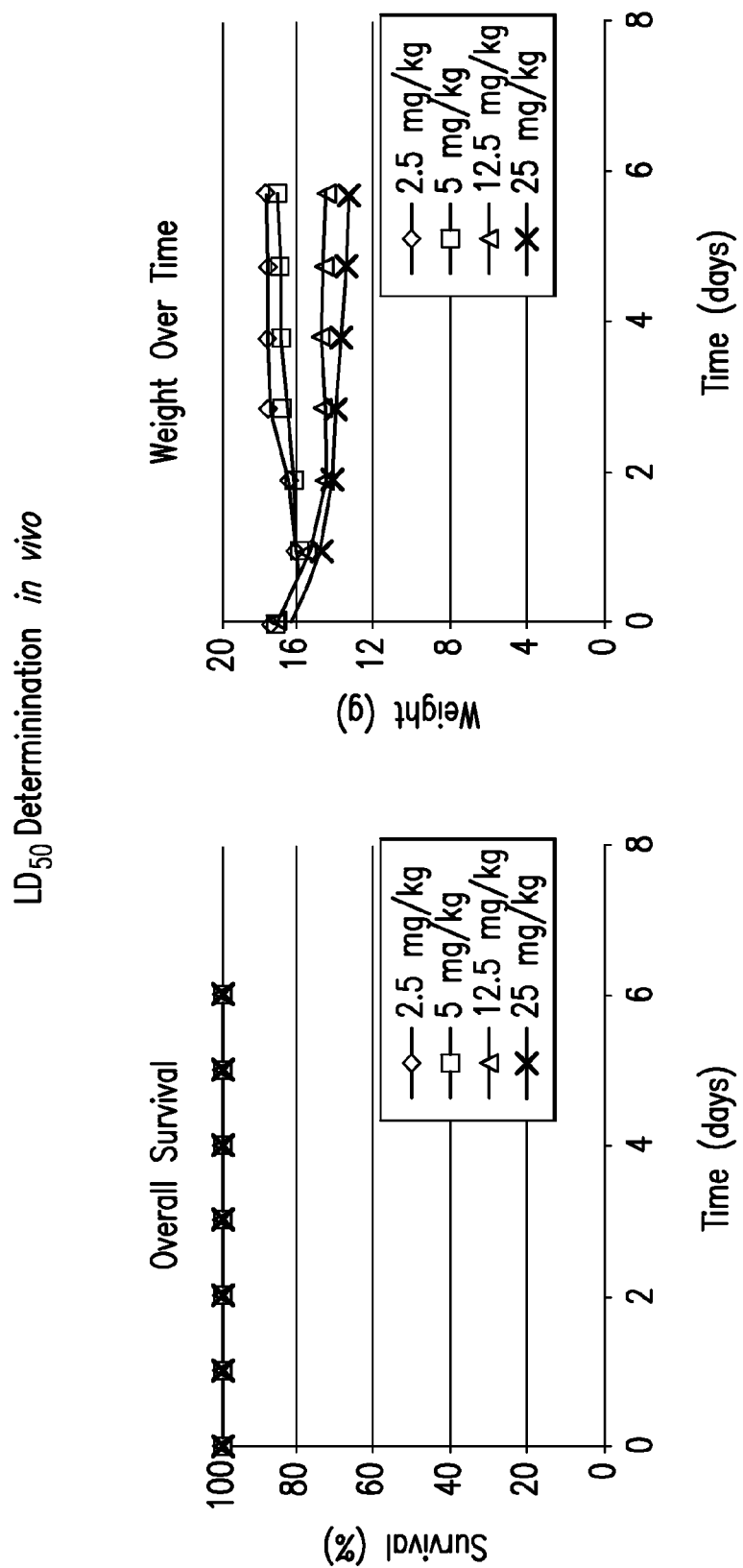

FIG. 50 shows in graph form the response of mice to doses of 365, in various strengths demonstrating safety.

Figure 51:
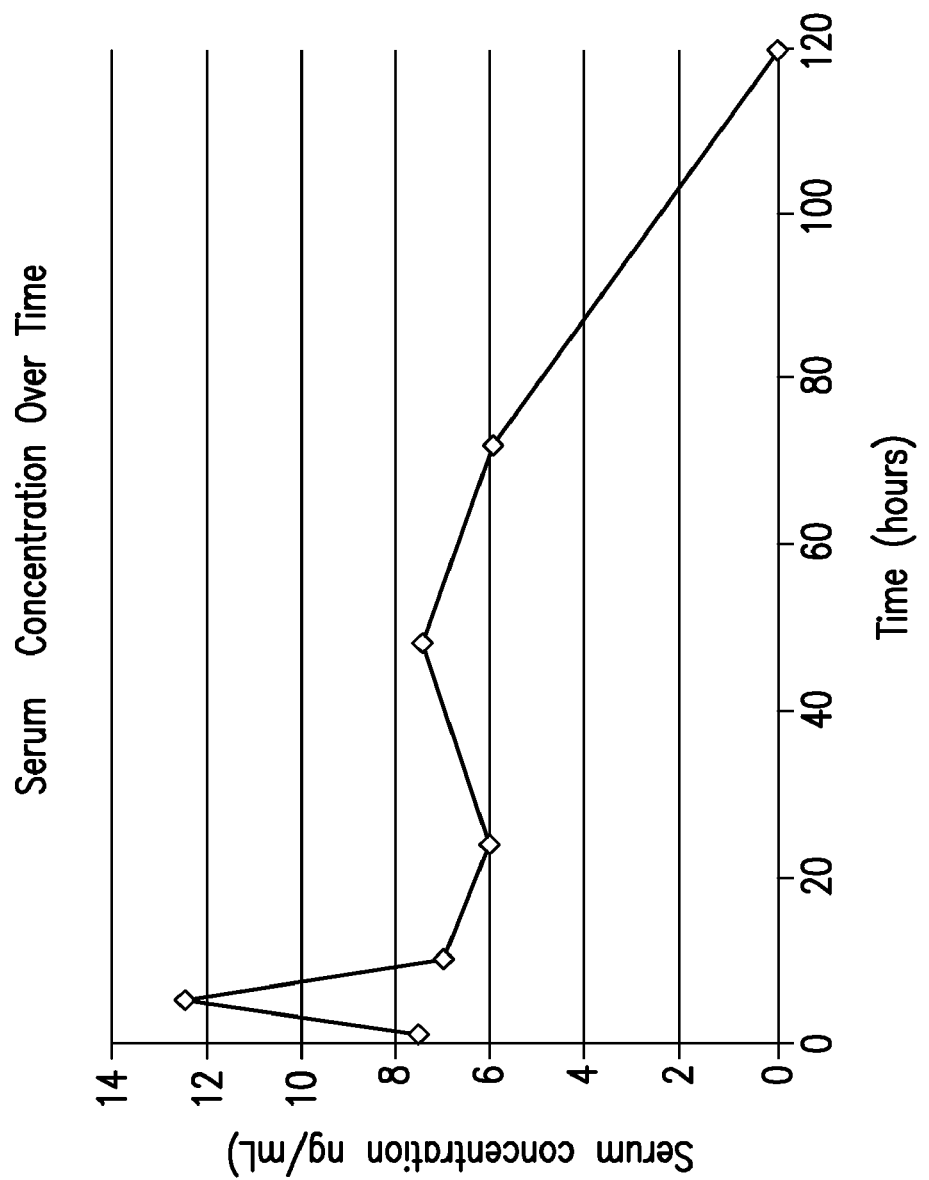
Figure 52:
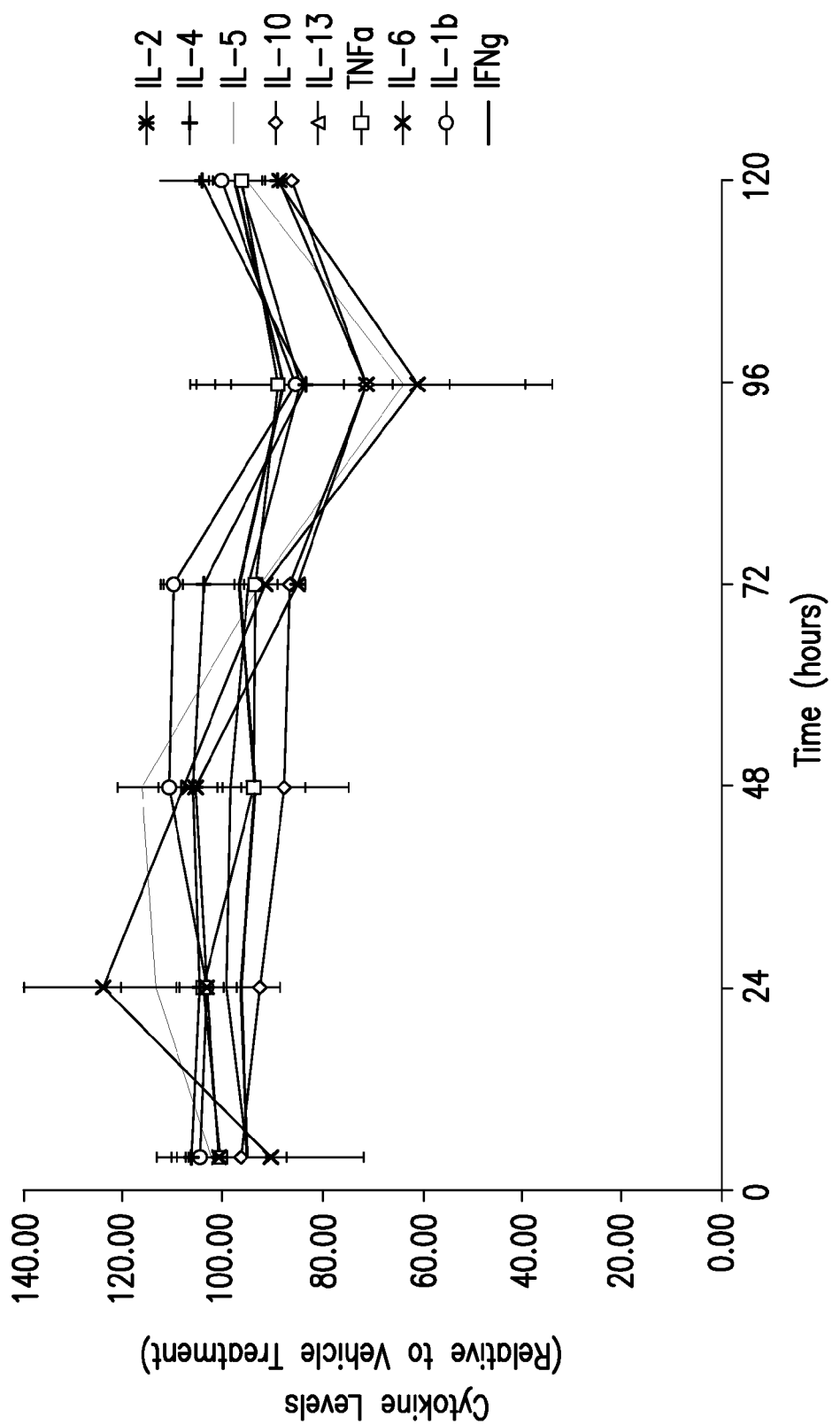

FIG. 51 is a graph presenting serum levels of 365 following a 5 mg/kg dosage. Using PBMC, FIG. 52 presents, in graph form, cytokine levels (relative to control) following administration of 365.

Figure 53:
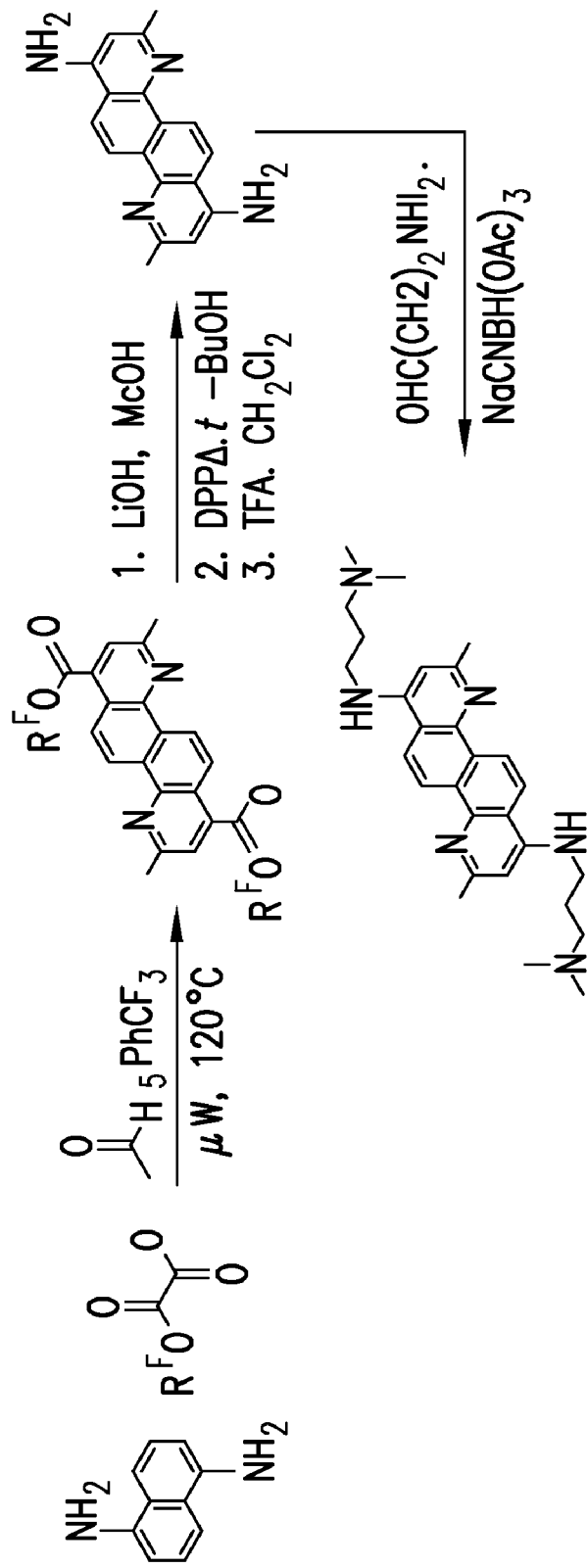

FIG. 53 provides a synthesis scheme for Compound 365 that can be followed by those of ordinary skill in the art in a fashion consistent with good laboratory practice to provide sustained and consistent purity and production levels.

Figure 54:
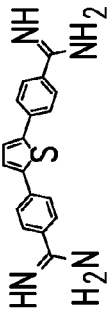

Compounds 723 and 365 are both balanced four ring structures. The effective FGI compounds also include active three ring compounds. FIG. 54 is a tabular presentation of some of the most important datapoints for compound 510, an active three ring structure. The presentation also includes suggested mechanism of action.

FIG. 55 presents, in tabular form, efficacy and safety data obtained for Compound 510 from a variety of cell based assays against six different viral threats.

FIG. 56 presents in graph and table the effectiveness of Compound 510 in preventing and treating Ebola Virus.

Compound 57 demonstrates the reduction in viral titer obtained against cowpox using Compound 510 in a cell based assay.

Compound 58 shows, by protein blot, graph and table, the results from using 5110 to treat Hepatitis C Virus, part of a family of Flavivruses that present both health and bioterrorism threats around the world.

Figure 59:
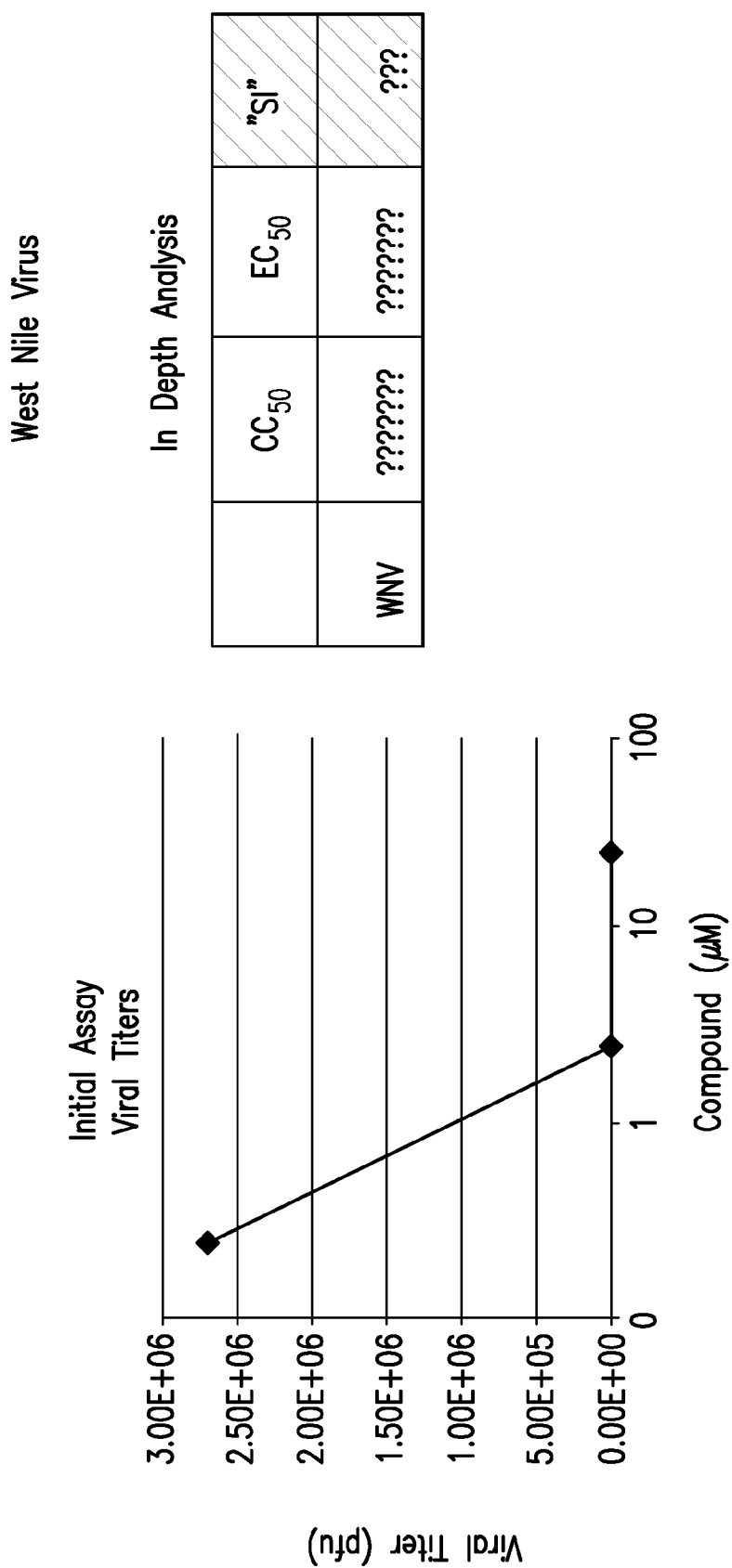

In a Vero Cell assay, compound 510 proved effective against West Nile Virus, as shown in FIG. 59.

Figure 60:
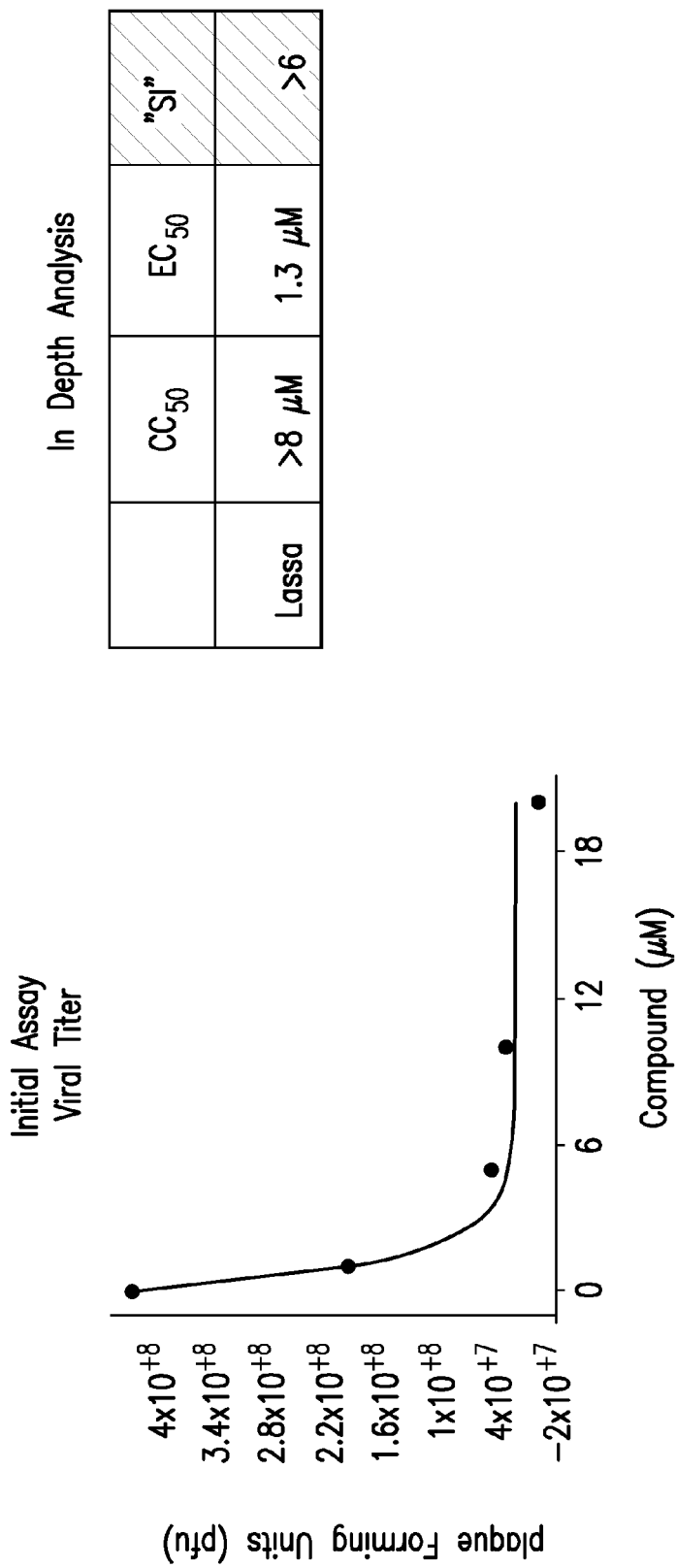
Figure 61:
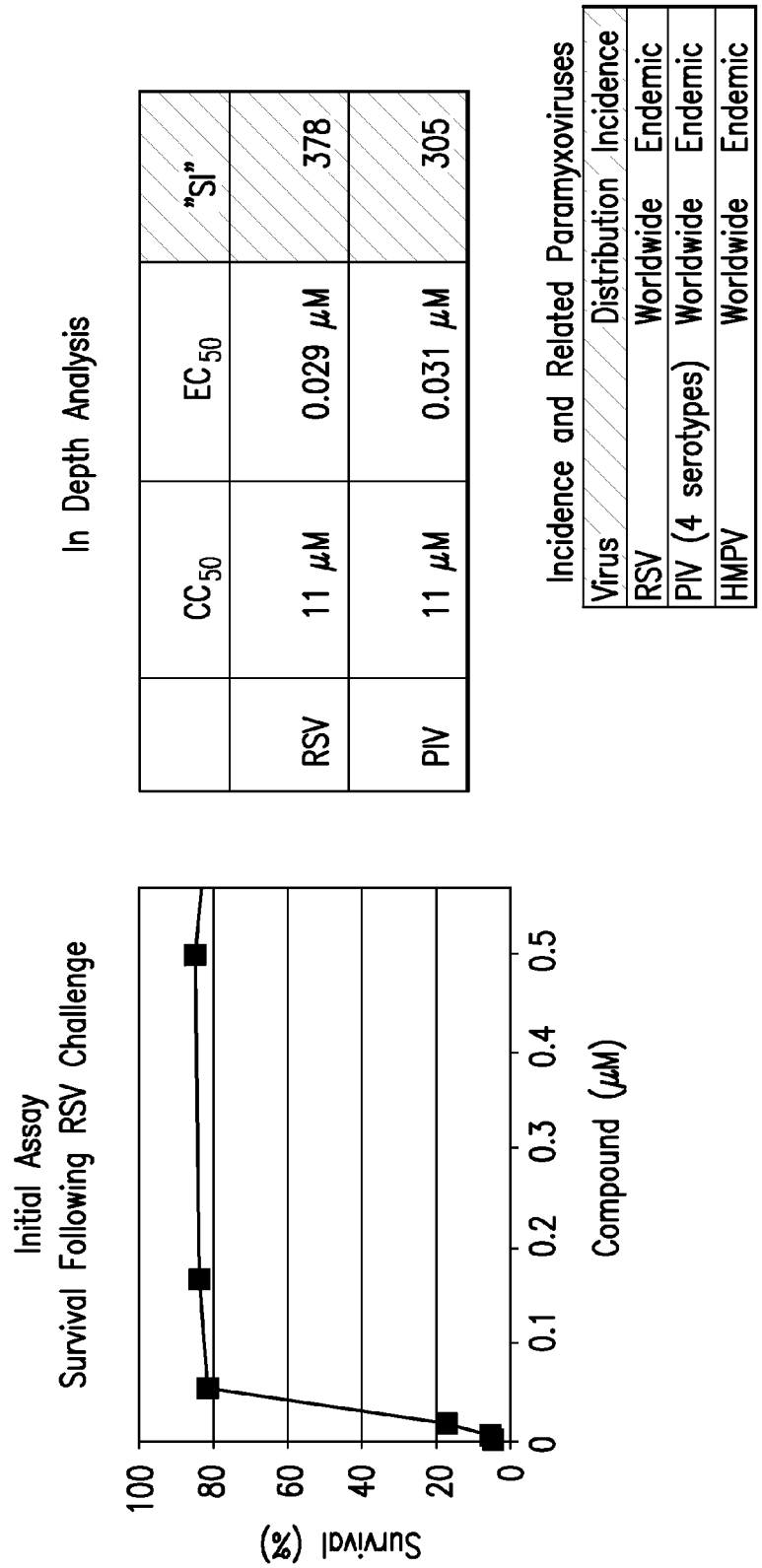

In FIG. 60, inhibition of Lassa Fever Virus, as shown by reduced viral titers In FIG. 61, a cell based assay showing cell survival following RSV infection, using 510 as an inhibition agent, is shown. Tabular data also is included for Parainfulenza.

Figure 62:
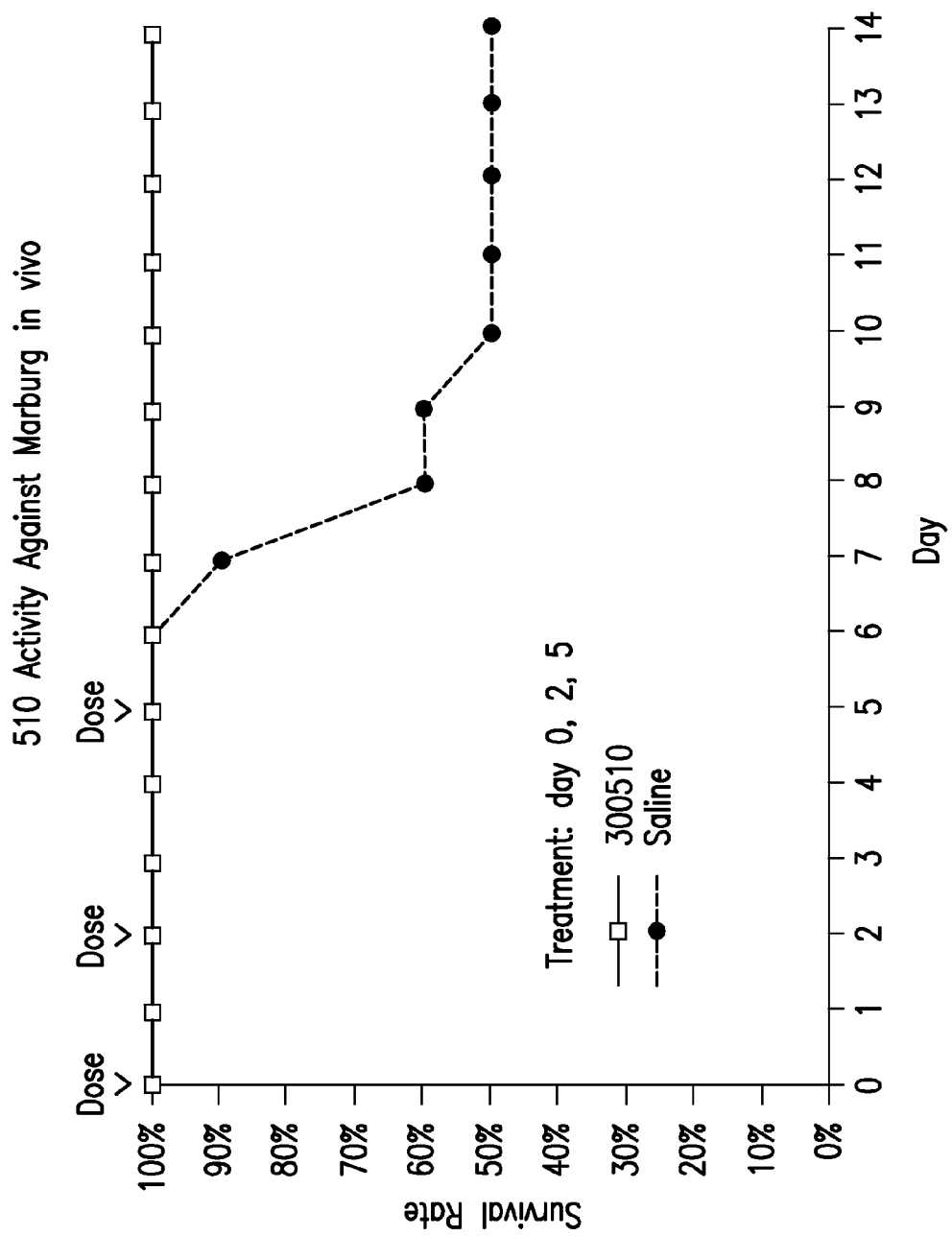

In FIG. 62, survival is the measure for an in vivo assay demonstrating protection of mice against challenge with Marburg Virus.

Figure 63:
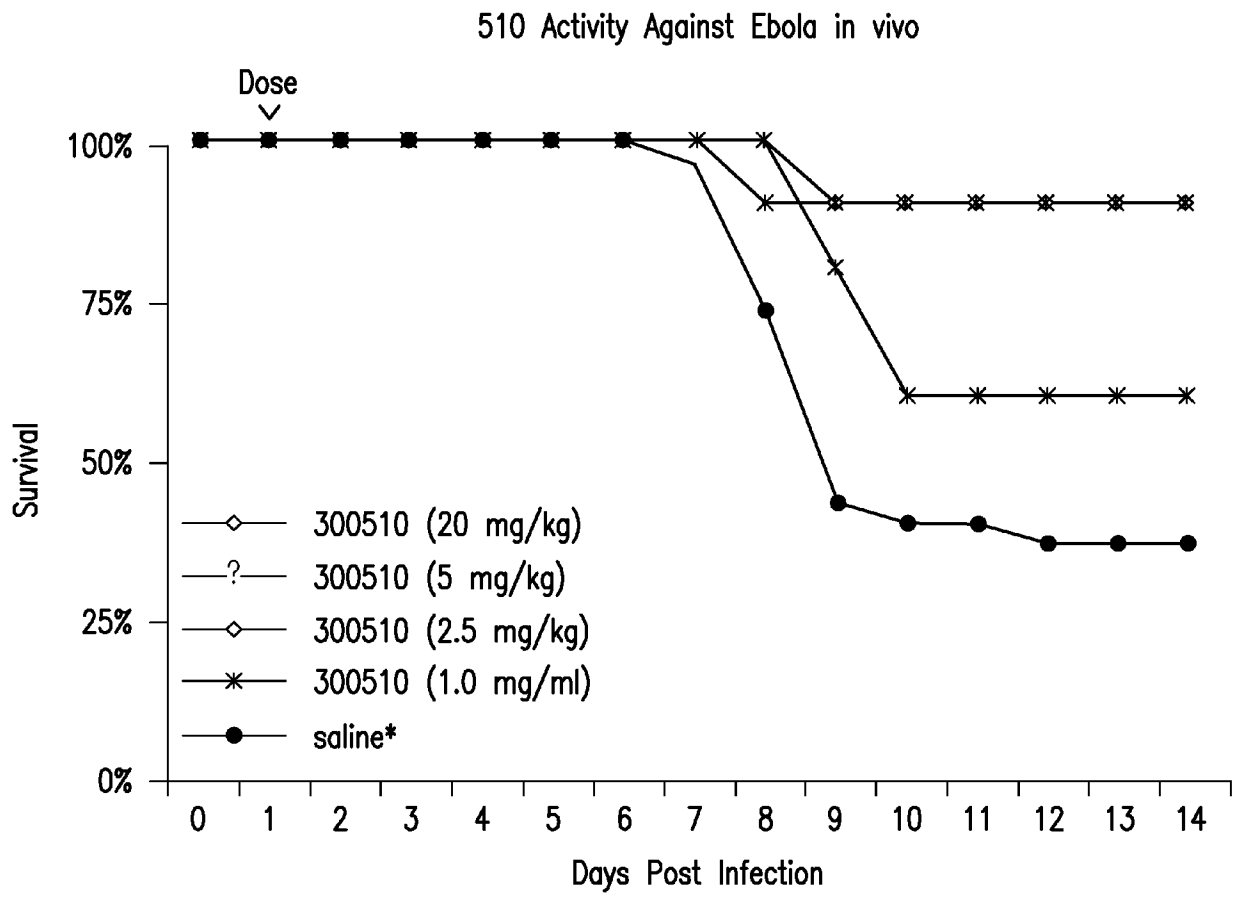

FIG. 63 presents, in graph form, the effectiveness of 510 in protecting mice as an in vivo challenge against Ebola virus. The effectiveness of 510 is shown over various dosage ranges.

Figure 64:
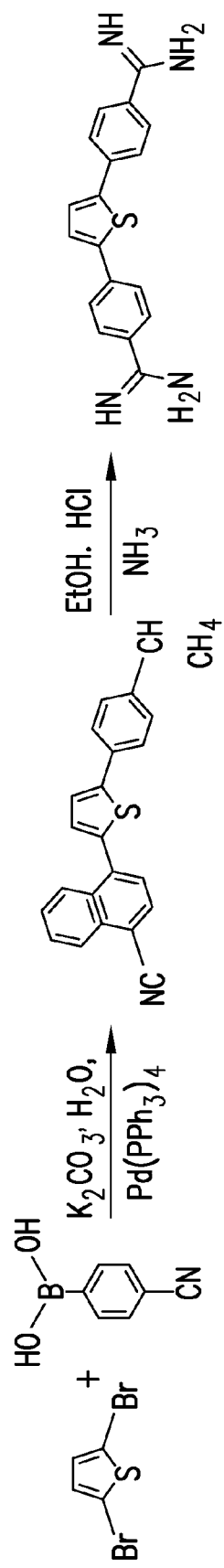

FIG. 64 presents a synthesis scheme for Compound 510 that permits its production consistent with good laboratory practices.

Figure 65:
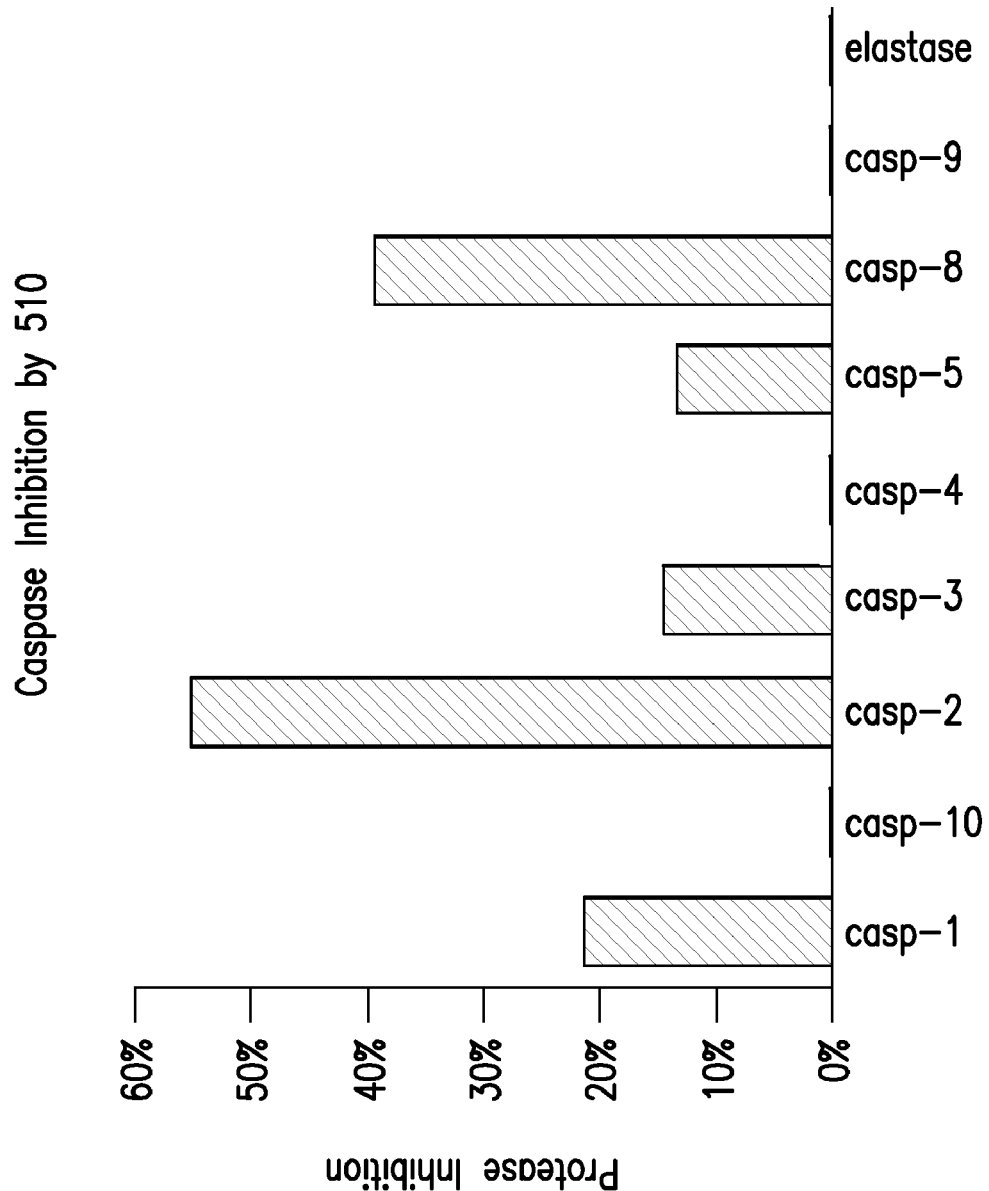

FIG. 65 presents in graph form data that Compound 510 inhibits Caspases selectively, providing elevated inhibition of Caspase 1, 2 and 8, but not of Caspase 4, 9 or 10.

FIG. 66 presents Caspase inhibition data for compound 510 in terms of $IC_{50}$ values.

Figure 67:
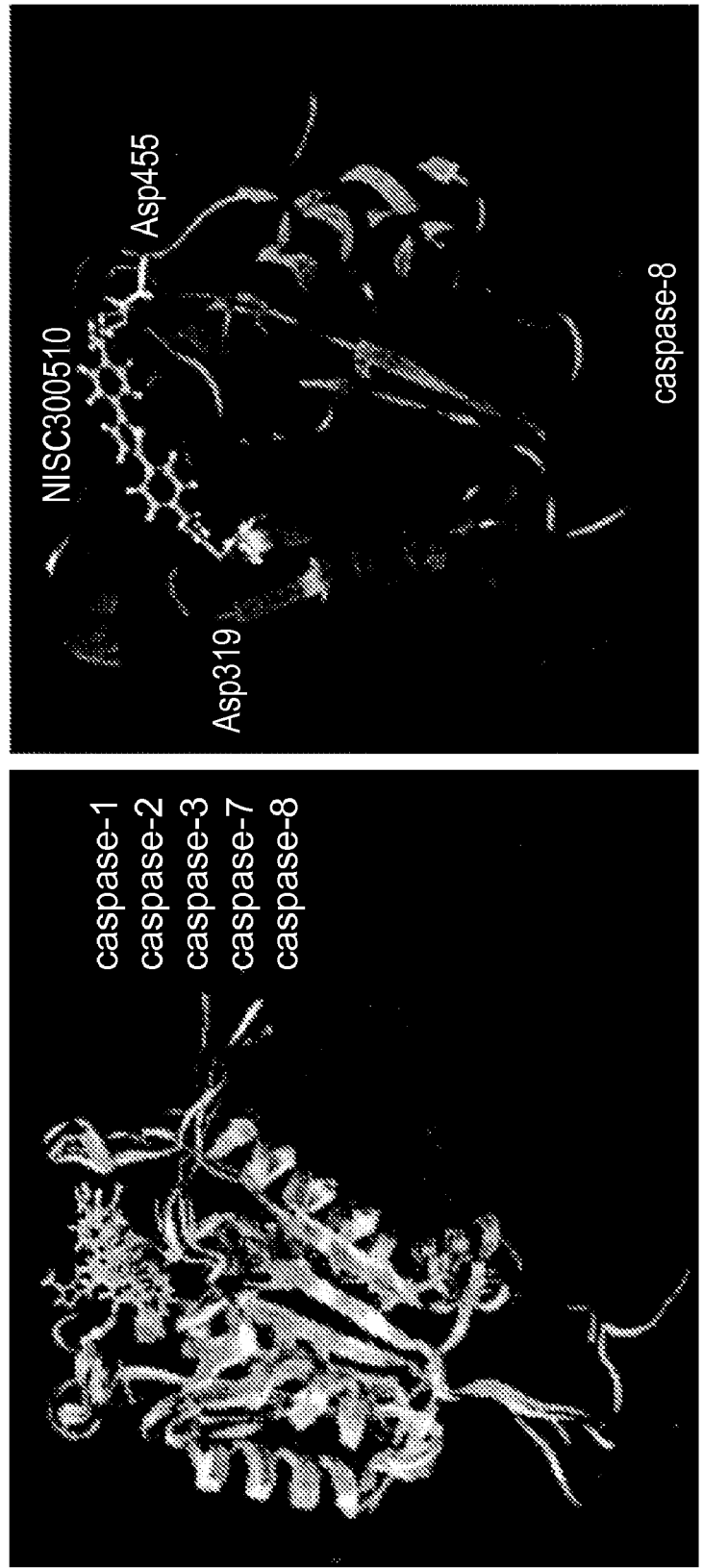

FIG. 67 presents possible molecular models to explain Caspase inhibition by Compound 510, showing how it may fit to bridge the active site.

Figure 68:
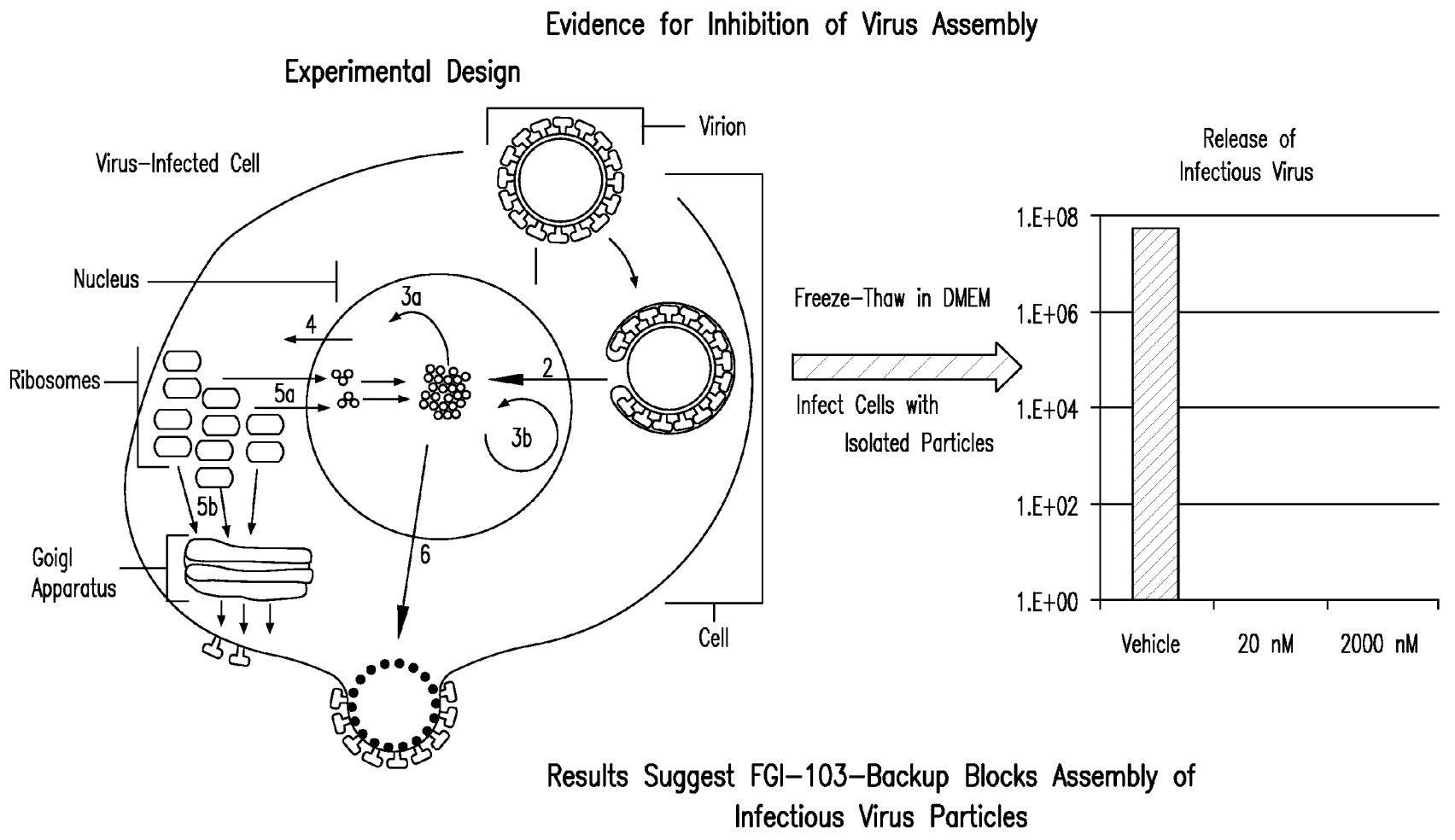

As with other FGI-103 compounds studied, as shown in FIG. 68, schematically and by graph, 510 appears to act by blocking or preventing assembly of infectious virus particles.

Figure 69:
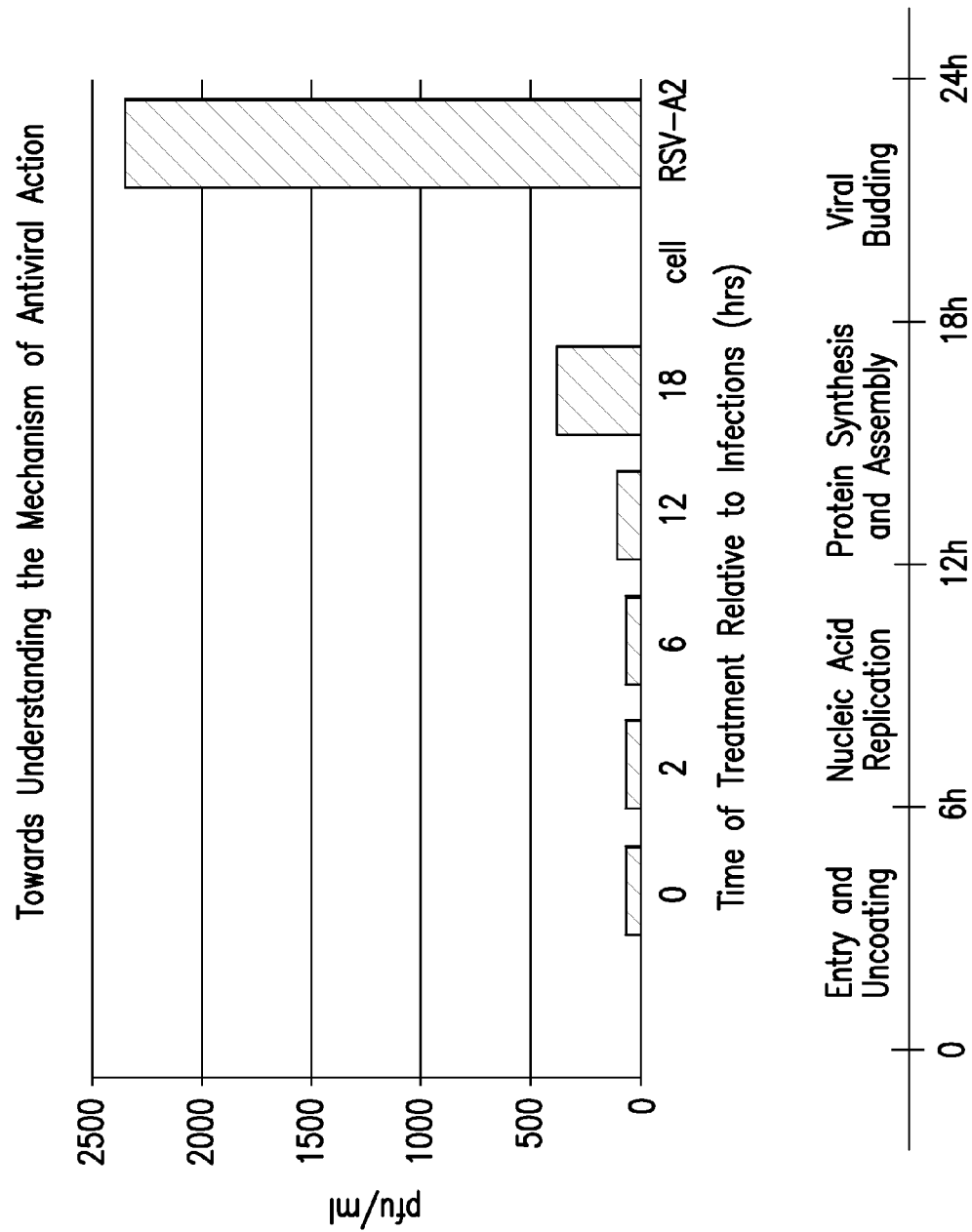

FIG. 69 presents data reflecting the impact on total viral particle generation had by time of treatment, using 723 as a treatment agent.

Figure 70:
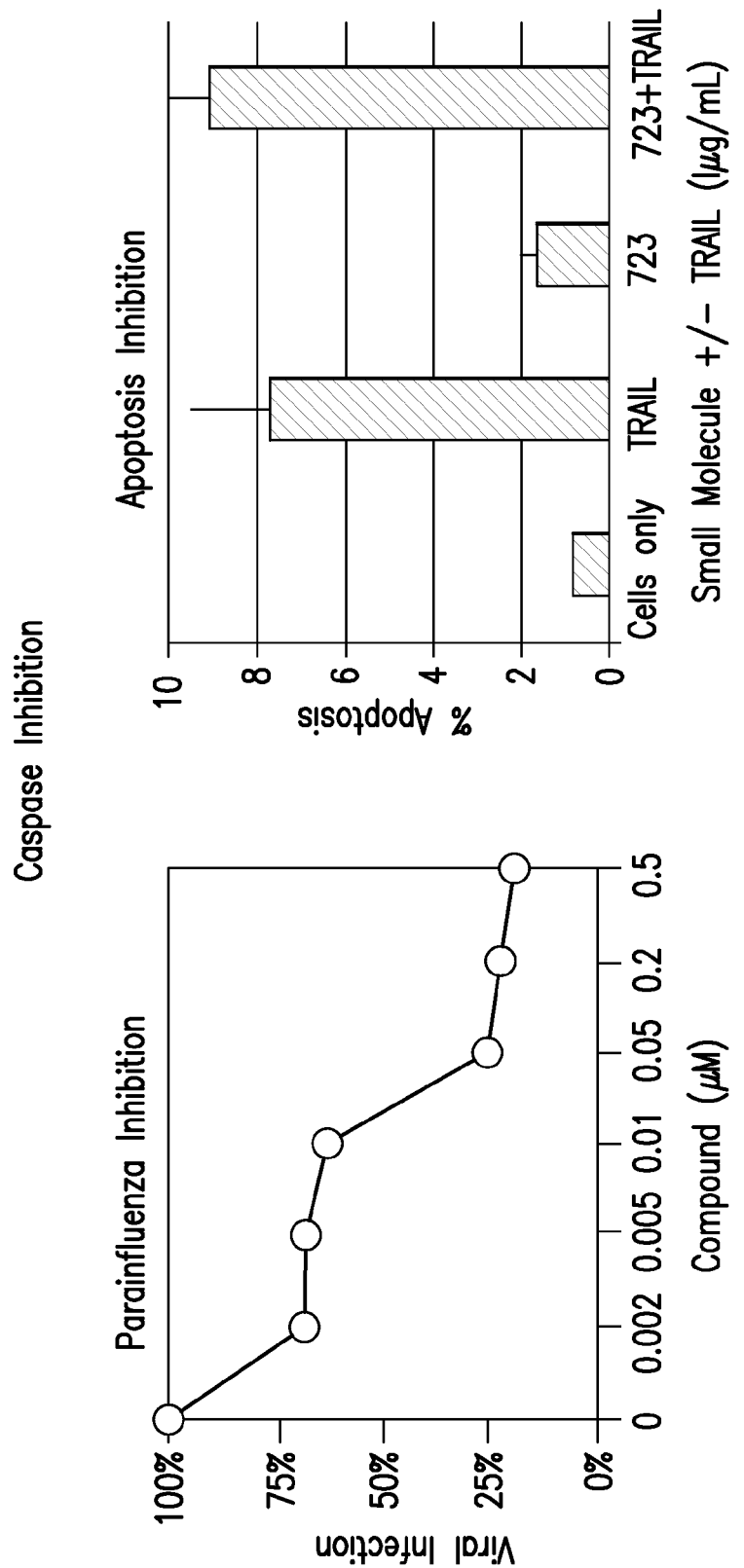
Figure 71:
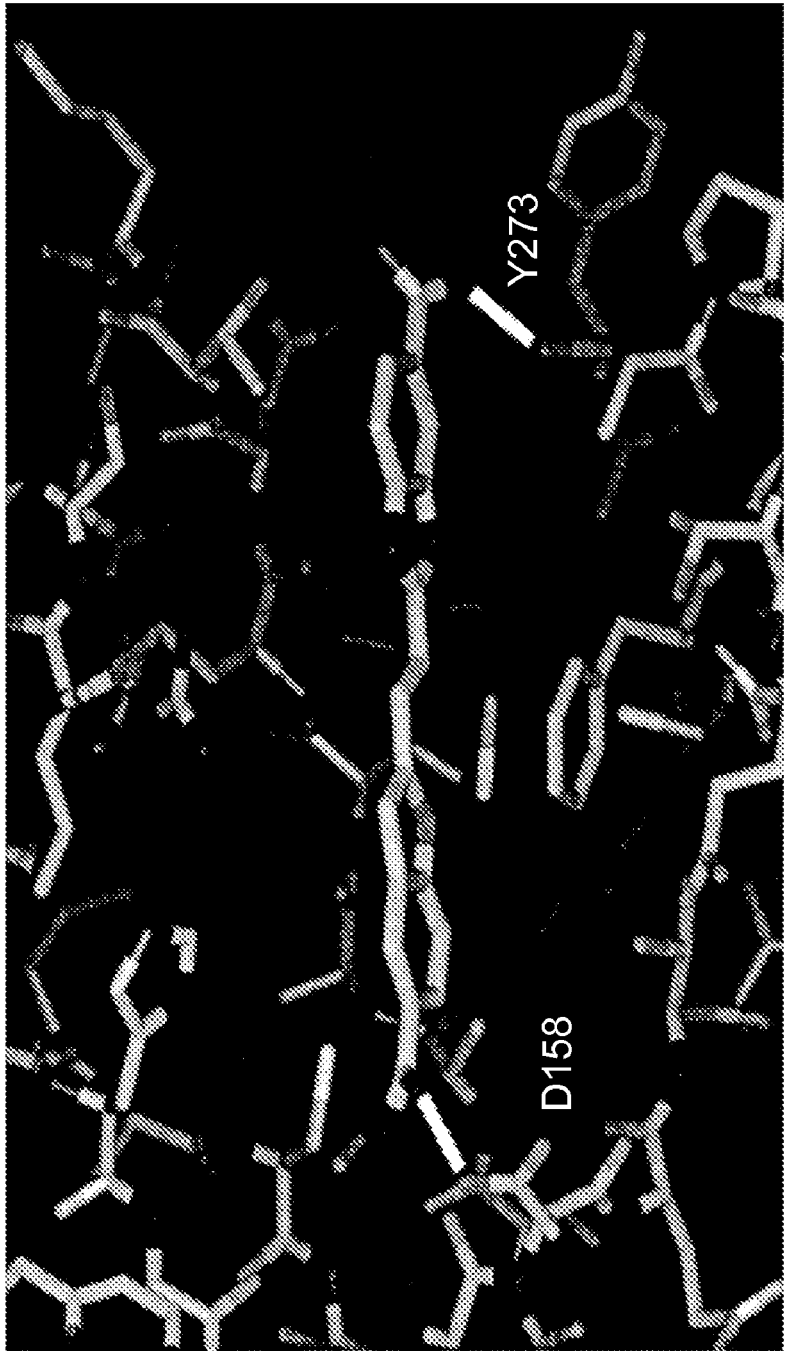

FIG. 70 presents a different sort of modeling imagery, showing how compound 723 structurally fits in the active cite of Caspase 2 as presented by atomic coordinate modeling FIG. 71 reflects an atomic crystal structure model for Caspase 8, demonstrating how FGI-103 compounds may fit to block the active site of the enzyme.

DETAILED DESCRIPTION OF THE INVENTION

The invention of this application finds applicability in the treatment of viral infection. While there is a vast collection of identified viral threats for both animals and humans that have yet to be catalogued and tested, the compounds of FGI-103 have shown themselves to be active in treating a wide range of viruses. These compounds have demonstrated 100% survival when used to treat, either therapeutically or prophylactically, mice challenged by Ebola virus. To the best of the inventors' knowledge, this has not been demonstrated by any agent to date. Ebola is just one of many "bioterrorism" viral threats that the United States government, and others, have identified as posing a potential weapon. The same compounds have simultaneously demonstrated effectiveness against viruses that may be difficult to vaccinate against, such as influenza. The Flu Vaccine works poorly in the elderly and other immune-compromised individuals who are at particular risk from the constantly mutating strains of influenza. To date, no strain has shown the ability to escape the protection conferred by the compounds of the FGI-103 family.

The effective compounds of the invention are not so limited, however. Having been demonstrated effective against viruses in both in vitro and in vivo tests, the compounds of this invention have also been demonstrated as effective in treating animal viruses, such as PRRS Virus and Bovine Corona virus, as well as other viruses, which pose both worldwide health problems and bioterrorism threats, such as SARS and Dengue viruses.

If one of skill in the art takes the compounds of FIGS. 6A-6C, each of which has been shown to exhibit activity in at least one cell based assay (against either Ebola or Monkeypox) and the properties of those compounds more closely studied and tested as discussed below, a family of compounds can be described which promise to exhibit activity against multiple viruses, either prophylactically or therapeutically, or both. That family can be described by the following formula:

$$Y-X-Y^1,$$

with the proviso that one of Y or $Y^1$ may not be present,

Wherein Y and $Y^1$ are each, independently, an alkyl group of 1-6 carbon atoms which may be straight, branched or cyclic, saturated, partially unsaturated or aryl and wherein each of Y and $Y^1$ present comprises two nitrogen atoms bearing one or two hydrogen atoms, with the proviso that up to one of said nitrogen atoms may constitute a ring atom in the event Y is cyclic and bear no hydrogen atoms, And wherein X is comprised of 3 or 4 ring moieties Z, wherein each Z is independently 5 or 6 atoms and may be saturated, unsaturated or aryl, any 2, 3 or 4 Z may be fused with an adjacent Z, wherein any unfused ring moieties Z are bound to at least one other ring moiety Z by a single bond, or an ethyl or propyl group which may bear an oxygen or nitrogen atom bound by a single or double bond, and wherein said X comprises 1-5 hetero atoms, each independently O, N or S, in place of a ring or ethyl or propyl carbon atom, and wherein said compound may further bear up to One or two derivatizing moieties selected from the group consisting of hydroxyl (—OH), amino (NH$_2$), amido, chloro, fluoro or other halogen, alkoxy (—OR), aryloxy (—OAr), trialkylammonium (—NR$_3$+), alkylamido (—NHCOR, —NRCOR'), arylamido (—NHCOAr, —NRCOAr, —NArCOAr), arylcarbamoyl (—NHCOOAr, —NRCOOAr), alkylcarbamoyl (—NHCOOR, —NRCOOR'), cyano (—CN), nitro (—NO$_2$), ester (—COOR, —COOAr), or alkyl halo, wherein, each case, said alkyl, R or AR group is from 1-6 carbon atoms.

Medical and scientific terms used herein are used in their standard and ordinary meaning whenever possible. The term "treating" as used herein means preventing, limiting or slowing infection by a virus. Thus, a host may be treated by administration of an FGI-103 compound where that host is given the FGI-103 compound before entering a danger area where the likelihood of infection by a virus is high. This type of treatment has particular application for servicemen and support personnel being deployed into areas where a virus against which there is little natural protection, such as Ebola, is known to be prevalent, or in the event of pandemic infection, such as that presented by influenza, where prophylactic protection is critical.

A host, such as a mammal (representative mammals include humans, commercial domestic animals such as horses, pigs, cows, sheep, goats and the like, animals of value in assays and discovery, including mice, rats, rabbits and their counterparts, as well as non-commercial animals like dogs, cats, monkeys and related domestic animals. It is also possible to treat viral infections in wild animal populations, such as elk, deer, wolves, bison and the like using the compounds of this invention) may be treated by having his virus "cured"—that is, no viral infection remaining in the host's body—or having the virus inhibited, that is, infectious particle generation reduced to a lower level such that the body's own natural resources can catch up with viral propagation and overwhelm the viral invader. In another form of treatment, the administered compound may slow the disease or extend survivorship in time to bring other treatments into play.

Administration may be through any of a variety of routes. Conventional routes of administration include IV, IM and IP. Data suggests that compounds properly derivatized may be administered orally, as shown in FIG. 33. Subcutaneous, cutaneous and inhalation routes may also be used to deliver the active agents of this invention. Importantly, the compounds of this invention are quite active. Minimum effective concentrations may range as low as one ng/kg. $EC_{50}$ values are given for a number of compounds, together with $ED_{50}$ values and $CC_{50}$ values, demonstrating safety for a broad range of effective dosages. For each of the compounds discussed extensively in this application a Safety Index calculated by dividing the $EC_{50}$ value by $CC_{50}$ is provided. Thus, while some of the FGI-103 compounds per se have been previously described, and are described in pending U.S. patent application Ser. No. 12/013,640 as suitable for use in dosage values of 0.002 mg-200 mg/kg of body weight, a focused range of about 10 ng/kg up to about 125 mg/kg may be preferable for the most active compounds. Accordingly, one can identify a preferred range for the pharmaceutical preparations of the invention to lie in the range of 1 ng/kilo/day-125 mg/kilo/day, IV, as target dosages. There is no minimum dosage protocol. To this end, as discussed below, the FGI103 compounds display robust activity in animal models against otherwise deadly viruses (Ebola, Marburg, Dengue, Influenza) such that doses in the range of 0.1-10 mg/kg, delivered once pre- or post-infection, are sufficient to prevent virus-mediated death. Those of skill in the art are well equipped by conventional protocols, given the identification of targets and compounds herein, to identify specific dosages for specific mammals, specific viruses and specific modes of administration.

The FGI 103 Compounds as a Class

Figure 10:
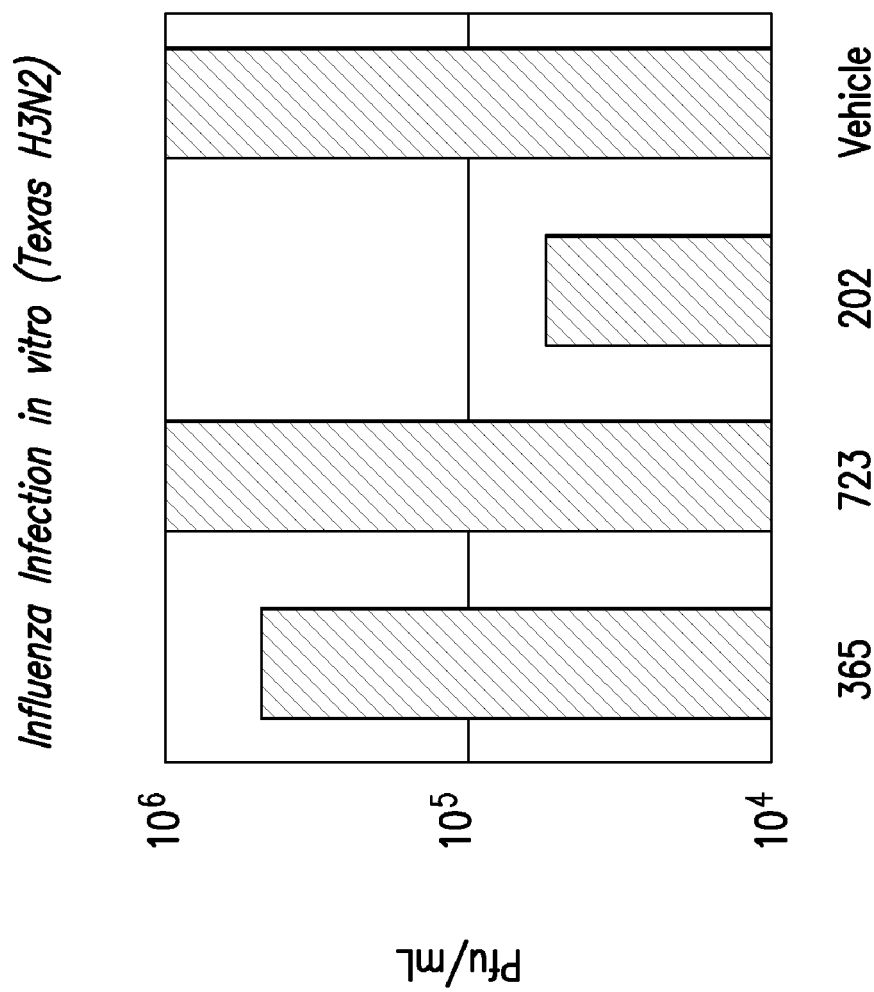
FIG. 10 is a graphical depiction of three active compounds, 365, 202 and 723, whose Formulae are set forth in FIG. 6A, showing influenza inhibition in an in vitro assay. FGI-103 compounds have been shown to be effective in providing protection against infection challenge.

Although presented below are three separate intensive case studies as Examples, it is worth looking at the FGI compounds as a whole. Comparative testing between FGI compounds against a selection of viral agents is set forth in FIGS. 10-17. What is remarkable about these studies is that although each of the FGI-103 compounds studied is more effective against some viruses than others, each is effective against multiple viruses. Thus, in FIG. 10, both 365 and 202 prove effective against Influenza infection, while 723—one of the most effective of the FGI-103 compounds tested, showed comparatively poorly. On retesting in other formats, it did better.

Figure 11:
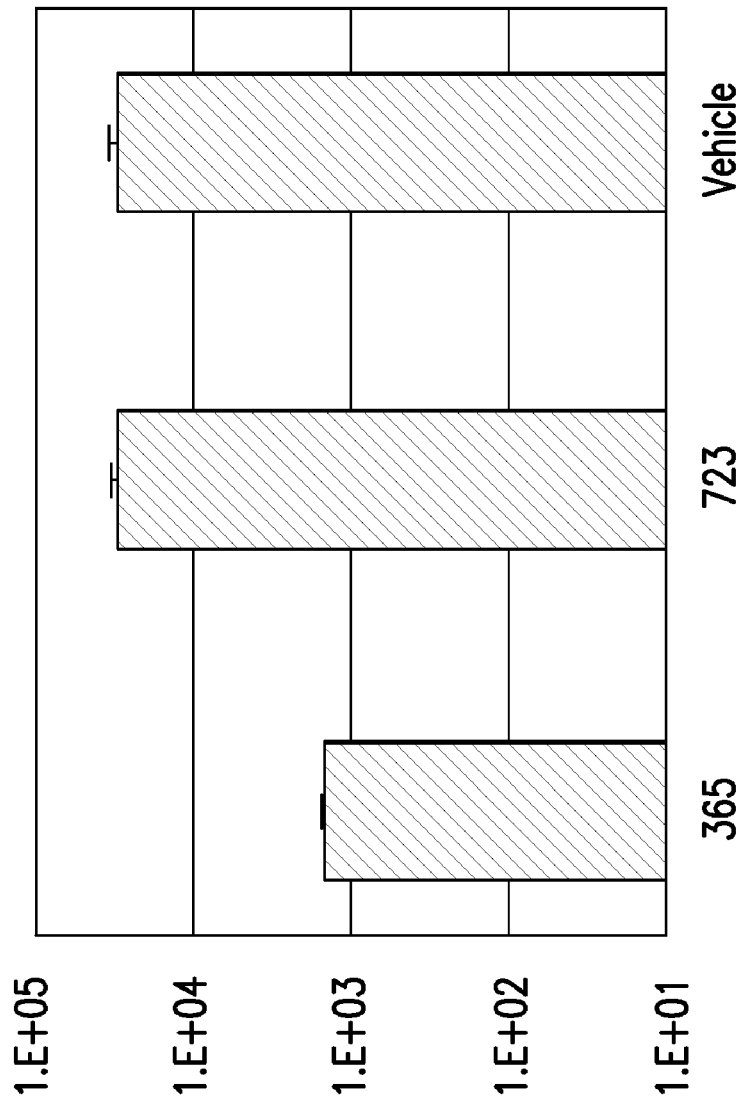
FIG. 11 also shows, graphically, inhibition of influenza virus, contrasting results for both FGI-103 compounds 365 and 723. The delivery vehicle is shown as a negative control.
Figure 12:
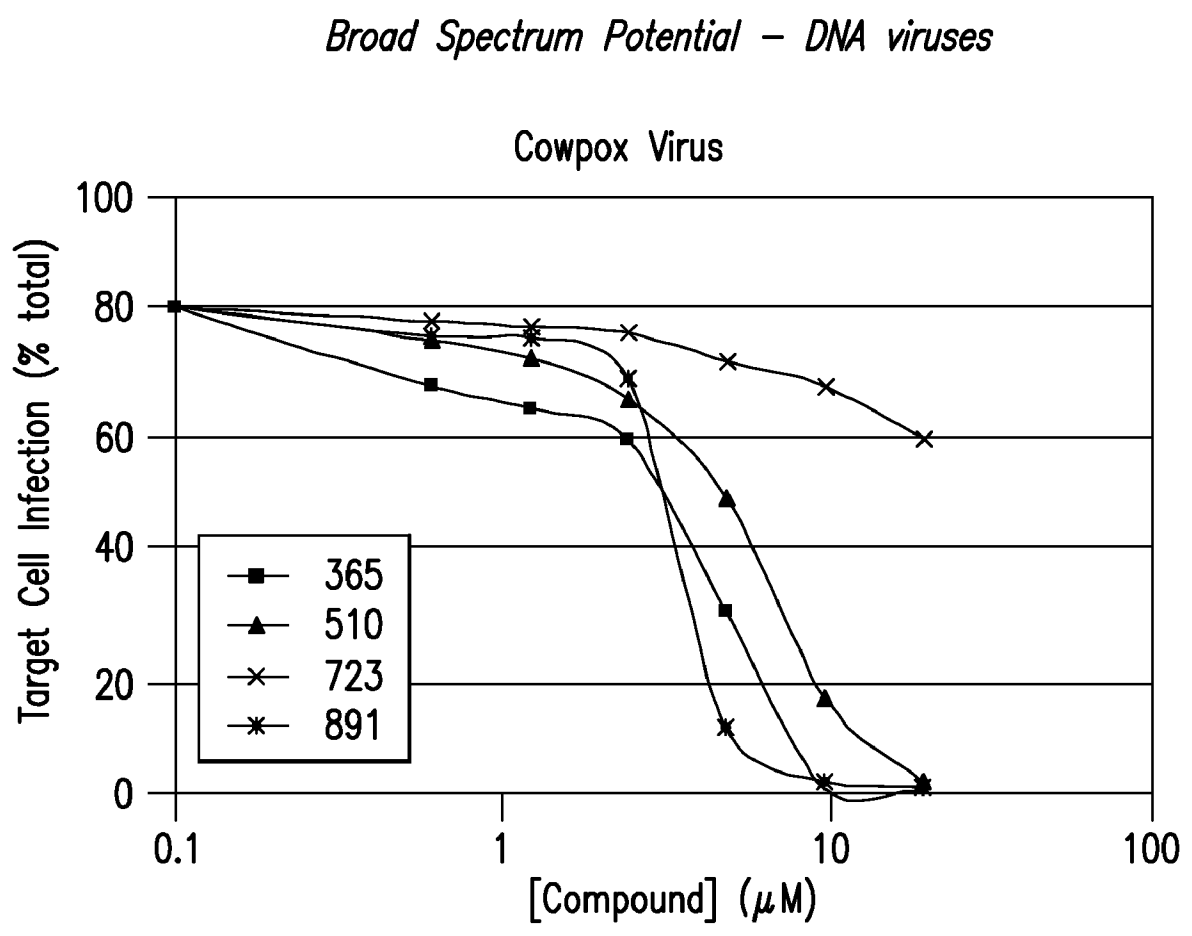
Figure 16:
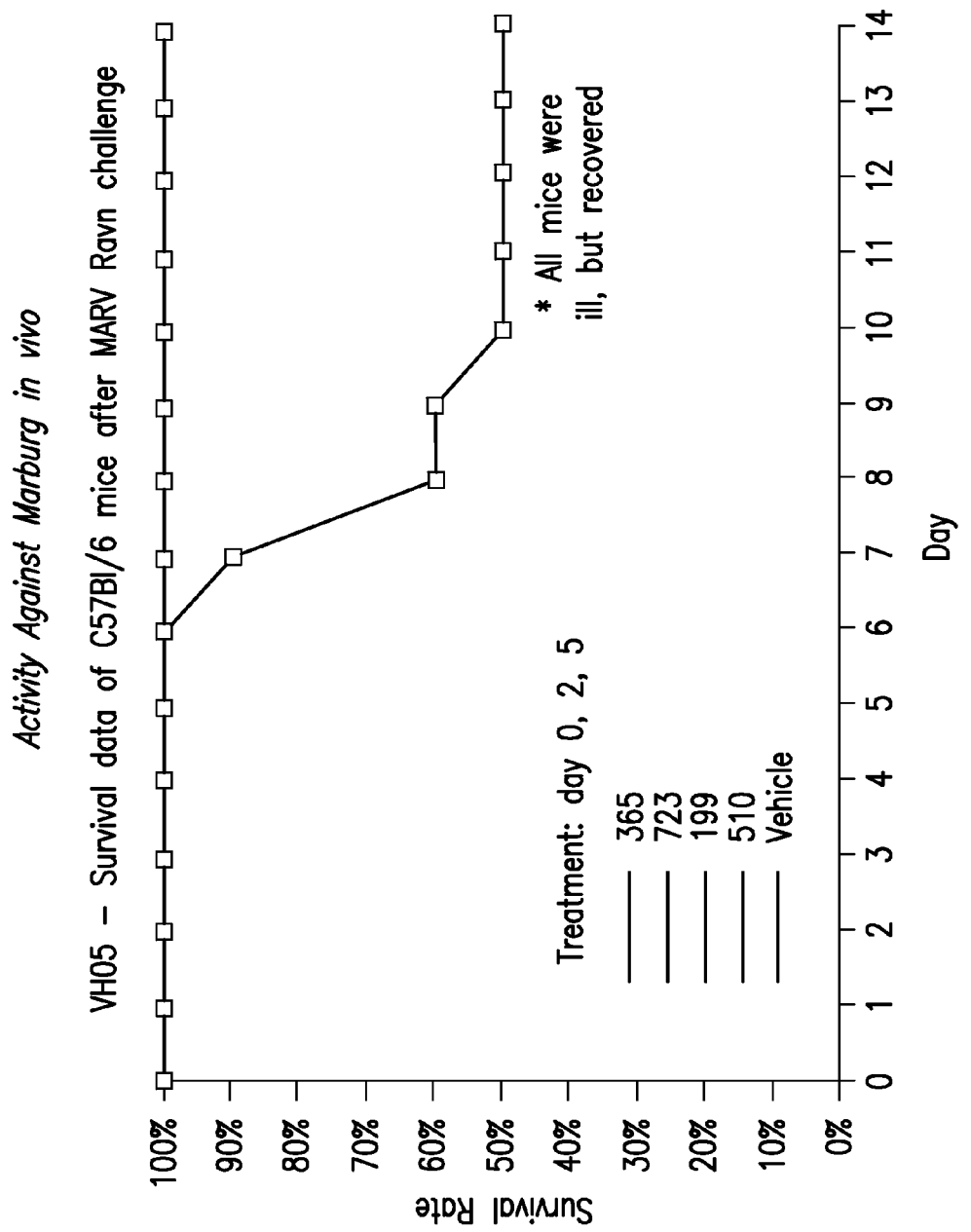
FIG. 16 gives the results, graphically, of in vivo challenge of mice with Marburg virus (MARV) for a different panel of FGI-103 compounds. Again, the structural formulae for all these compounds are provided in FIG. 6A-6C.

FIG. 11 compares 1 uM dosage effectiveness against HIV, perhaps the single virus against which an effective regimen is most actively sought today. Each of four different FGI-103 compounds was shown to inhibit cowpox virus, another DNA virus—three showing complete inhibition at a dosage value of about 10 uM, when treated prophylactically, as shown in FIG. 12. By the same token, both 723 and 365 showed effectiveness, at measured values, in inhibiting PRRS, FIG. 13, and the same two test compounds were shown effective against Bovine Corona virus which is similar to SARS. FIG. 14. 723 together with another FGI 103 compound, 202, was tested against Ebola in vivo, with a 1 hour before challenge dosage, and then two subsequent administrations, at a 10 mg/kg dosage level. 100% of the treated animals survived. Similar performance against another hemorrhagic virus, Marburg, n vivo, has been demonstrated, as reflected in FIG. 16. While many DNA viruses are based on RNA, a different class of viruses employ DNA. The FGI-103 compounds have been shown to be effective against DNA viruses as well, such as cowpox virus. FIG. 17 shows survival data for a variety of FGI-compounds against cowpox.

Another important aspect of the results demonstrated at this early date for the FGI 103 compounds is that they have been shown to be effective not only through in vitro cell based assays, but in vivo as well. It is rare that a class of compounds holds its demonstrated in vitro activity in against a wide variety of viral agents, including RNA virus and DNA viruses, but retain that activity when tested in vivo. Bear in mind that each of the FGI103 compounds structurally presented in FIGS. 6A-6C exhibited in vitro activity against at least one, if not more, viral agents, and that too date, none of the tested agents have failed to retain that activity in vivo and some taste of the scope and importance of the discovery that FGI-103 compounds can be used to inhibit a large variety of viruses is apparent. The variety of viruses treated by the FGI-103 compounds as a class is remarkable. Viruses that are recognized bioterrorism threats, like Ebola, Marburg and Dengue fever are effectively inhibited by FGI-103 compounds. Other treatment resistant viruses, like Rift Valley Fever and Lassa Fever viruses, are effectively treated by the class of compounds designated as FGI-103 compounds, as reflected in the information set forth in FIGS. 10-17. A summary of early testing, which is supplemented by the three "case studies" set forth below, is presented in FIG. 18. It is unusual for a single anti-viral agent to demonstrate invectiveness against so many different viruses, drawn from so many different viral families. It would of course be a life's work to demonstrate safety and efficacy for a large number of FGI-103 compounds against a large number of viruses. Testing of this family of small molecules, which, as discussed below, appear to target a host protein or pathway, rather than the virus, will continue for some time. Nonetheless, the extensive testing conducted to date demonstrates the broad applicability of these agents, and convincingly demonstrates that rather than attacking viruses specifically, it targets some body action, pathway or protein that is implicated in viral infection or replication.

These results clearly suggest that the FGI-103 compounds will have activity against a large number of viruses including Group I viruses (as demonstrated by activity against pox viruses); Group IV viruses (as demonstrated by activity against bovine corona viruses); Group V (represented by Ebola virus) and other families of viruses as represented by the viruses tested as presented in the Figures of this application.

Initial results, together with information on the mode of action of these compounds, clearly indicates that these compounds will have activity against other groups of viruses based on the broad-spectrum activity associated with targeting of the host. These would include viruses in Groups II, III, VI and VII.

Viral Groupings:

Group I: viruses possess double-stranded DNA and include such virus families as Herpesviridae (examples like HSV1 (oral herpes), HSV2 (genital herpes), VZV (chickenpox), EBV (Epstein-Barr virus), CMV (Cytomegalovirus)), Poxyiridae (smallpox) and many tailed bacteriophages. The mimivirus was also placed into this group.

Group II: viruses possess single-stranded DNA and include such virus families as Parvoviridae and the important bacteriophage M13.

| Virus Family | Virus Genus | Virion-naked/enveloped | Capsid Symmetry | Type of nucleic acid |
|---|---|---|---|---|
| 1. Adenoviridae | Adenovirus | Naked | Icosahedral | ds |
| 2. Papovaviridae | Papillomavirus | Naked | Icosahedral | ds circular |
| 3. Parvoviridae | B 19 virus | Naked | Icosahedral | ss |
| 4. Herpesviridae | Herpes Simplex Virus, Varicella zoster virus, Cytomegalovirus, Epstein Barr virus | Enveloped | Icosahedral | ds |
| 5. Poxviridae | Small pox virus, Vaccinia virus | Complex coats | Complex | ds |
| 6. Hepadnaviridae | Hepatitis B virus | Enveloped | Icosahedral | ds circular |
| 7. Polyomaviridae | Polyoma virus (progressive multifocal leucoencephalopathy) | ? | ? | ds |

RNA Viruses

Group III: viruses possess double-stranded RNA genomes, e.g. rotavirus. These genomes are always segmented.

Group IV: viruses possess positive-sense single-stranded RNA genomes. Many well known viruses are found in this group, including the picornaviruses (which is a family of viruses that includes well-known viruses like Hepatitis A virus, enteroviruses, rhinoviruses, poliovirus, and foot-and-mouth virus), SARS virus, hepatitis C virus, yellow fever virus, and rubella virus.

Group V: viruses possess negative-sense single-stranded RNA genomes. The deadly Ebola and Marburg viruses are well known members of this group, along with influenza virus, measles, mumps and rabies.

| Virus Family | Virus Genera | Virion-naked/enveloped | Capsid Symmetry | Type of nucleic acid |
|---|---|---|---|---|
| 1. Reoviridae | Reovirus, Rotavirus | Naked | Icosahedral | ds |
| 2. Picornaviridae | Enterovirus, Rhino virus, Hepatovirus, Cardiovirus, Aphthovirus, Parechovirus, Erbovirus, Kobuvirus, Teschovirus | Naked | Icosahedral | ss |
| 3. Caliciviridae | Norwalk virus, Hepatitis E virus | Naked | Icosahedral | ss |
| 4. Togaviridae | Rubella virus | Enveloped | Icosahedral | ss |
| 5. Arenaviridae | Lymphocytic choriomeningitis virus | Enveloped | Complex | ss |
| 6. Retroviridae | HIV-1, HIV-2, HTLV-I | Enveloped | Complex | ss |

-continued

| Virus Family | Virus Genera | Virion-naked/enveloped | Capsid Symmetry | Type of nucleic acid |
|---|---|---|---|---|
| 7. Flaviviridae | Dengue virus, Hepatitis C virus, Yellow fever virus | Enveloped | Complex | ss |
| 8. Orthomyxoviridae | Influenzavirus A, Influenzavirus B, Influenzavirus C, Isavirus, Thogotovirus | Enveloped | Helical | ss |
| 9. Paramyxoviridae | Measles virus, Mumps virus, Respiratory syncytial virus | Enveloped | Helical | ss |
| 10. Bunyaviridae | California encephalitis virus, Hantavirus | Enveloped | Helical | ss |
| 11. Rhabdoviridae | Rabies virus | Enveloped | Helical | ss |
| 12. Filoviridae | Ebola virus, Marburg virus | Enveloped | Helical | ss |
| 13. Coronaviridae | Corona virus | Enveloped | Complex | ss |
| 14. Astroviridae | Astrovirus | Naked | Icosahedral | ss |
| 15. Bornaviridae | Borna disease virus | Enveloped | Helical | ss |

Reverse Transcribing Viruses

Group VI: viruses possess single-stranded RNA genomes and replicate using reverse transcriptase. The retroviruses are included in this group, of which HIV is a member.

Group VII: viruses possess double-stranded DNA genomes and replicate using reverse transcriptase. The hepatitis B virus can be found in this group.

We have discovered that many of the host mechanisms necessary for viral propagation utilize targets that are highly conserved among mammalian or eukaryotic species. Consequently, these compounds could have application for human or veterinary viral diseases. These viral diseases could include but are not limited to PRRS virus, porcine or bovine circo viruses, porcine or bovine corona viruses, porcine or bovine RSV, porcine, bovine or avian influenza, EIAV, bluetongue, or foot and mouth diseases (FMD) viruses.

Some viruses are causative of more chronic diseases and the morbidity or mortality relates to the presence of virus. These diseases include hepatocellular carcinoma (associated with either HBV or HCV), chronic fatigue syndrome (associated with EBV) and other diseases linked with viral infection. The FIG-103 compounds should be effective in the treatment of these virus-related diseases, as well as the viruses themselves.

The FGI-103 compounds could be used for the treatment or prevention (prophylaxis) of single viral pathogens (e.g., HIV or HBV) or combinations thereof (HIV and HBV). Likewise, these individual or broad-spectrum applications could entail any or all of the virus groups detailed above.

Another method could be the use of the compounds for certain indications associated with one or more viruses in humans and animals. For example, these compounds could be used for the prevention or treatment of respiratory virus infections, which can be caused by one or more of the pathogens from the groups identified above. Likewise, these compounds could have application against one or more blood-borne pathogens (e.g., HIV and/or HBV and HCV).

The compounds could have application for the prevention, treatment or maintenance of acute or chronic viruses in humans. Acute applications include short-term prevention or treatment of viral infection, examples of which include influenza, rotavirus or filovirus infection. Chronic applications could include recurrent outbreaks, such as is observed with genital herpes) or infrequent outbreaks (such as those associated with zoster infection during shingles). Likewise, treatment could be intended over the long term to maintain low levels of viral load for chronic virus infection (e.g., for HIV, HBV or HCV treatment). The assays set forth herein, demonstrating effective protection, prophylactically and/or therapeutically, against a wide number of viruses, both in vitro and in vivo can of course be used to assess the activity of other FGI103-compounds responsive to the chemical structural formula provided.

FGI-103 Compound 723

Figure 19:
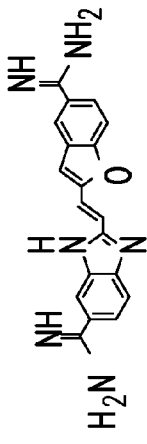

FIG. 19 identifies Compound 723 as 2-[2-(5-carbamimidoyl-benzofuran-2-yl)-vinyl]-3H-benzoimidazole-5-carboxamidine. As reflected in FIG. 19, this compound has been demonstrated to be effective at remarkably low dosages against a variety of viruses selected from different families, in vitro. This same compound has been demonstrated to confer 100% protection in vivo on mammals (mice) against lethal challenge whether administered prophylactically (at or before the time of challenge) or therapeutically (administered only after challenge). It exhibits a $t_{1/2}$ in mammalian models on the order of two-four hours, and has a good Safety Index. Testing on this compound continues. It fits, chemically, into the Y—X—Y$^1$ formula set forth above.

Figure 21:
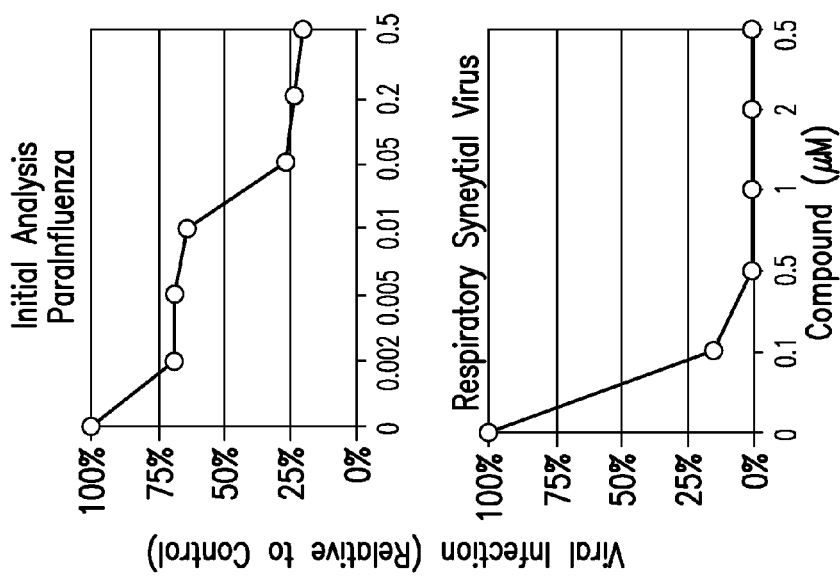

The various diseases against which this compound has been tested in some format are set forth in FIG. 20. While not all tests for all viruses have been completed, this compound, 723, exhibits broad based activity against a spectrum of viruses, drawn from a variety of families. As one example of the testing conducted, in FIG. 21, assays against a grouping of Paramyxoviruses, including Parainfluenza and RSV, have been completed, in vitro. While the endpoint of this assay is cell death, rather than some finer scale titration, it can be clearly seen that 723 was effective in conferring a great degree of protection against viral challenge—supporting the conclusion that this compound can be used to treat mammalian hosts either infected with the viruses, or threatened with such infection. As with most of the viruses tested, this compound showed similar performance against all serotypes available, an important distinction from prior art efforts which are frequently "tailored" to treat only the dominant serotype.

Figure 22:
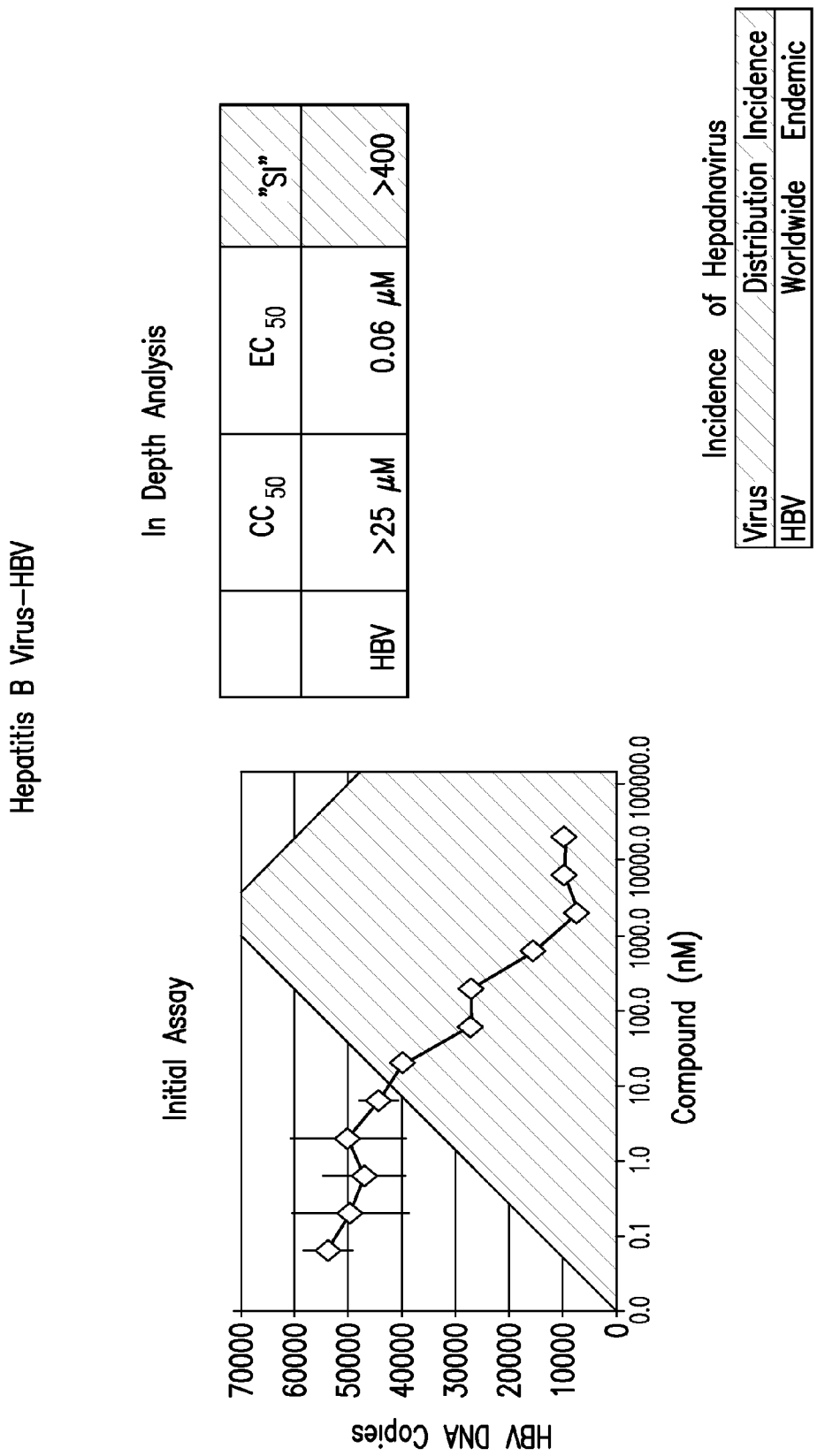

The effectiveness, at nanomolar levels, of 723 in treating Hepatitis B virus (HBV) is set forth in FIG. 22. HBV has infected about one third of the world's population—to date, the only known treatments are supportive steps, the disease is avoided only by vaccination. The graph provides illustration, in dose response fashion, of the reduction in the number of viral copies found, as the cells are treated or protected with 723. HBV is one of the viruses associated with chronic diseases, such as cirrhosis of the liver. Although cirrhosis can be caused by a variety of sources, reducing HBV populations and treating HBV infection should permit more effective intervention and suppression of cirrhosis in HBV sufferers.

Dengue fever, and similar viruses such as Hepatitis C virus and West Nile virus, are also treated by administration of 723. The cells used in the assay reflected in FIG. 23 are DC-Sign cells, and the number of infected cells in the face of challenge, when treated with 723, falls drastically when effective amounts of 723 is administered. Dengue fever is a virus of some significance, as it constitutes both a "bioterrorism" threat, and thus measures available to treat it become an issue of National Security and safety, and a health threat throughout much of Africa and the tropics. Dengue fever is characterized by four major serotypes—in the past, these serotypes have been sufficiently different as to frustrate vaccination—there is no cross-serotype protection, which offers the opportunity for multiple serotype epidemics. As shown in FIG. 23, 723 is effective against all four Dengue serotypes, and can be administered prophylacitaclly or therapeutically, providing a dramatic advance in the treatment of this virus.

Among the most dramatic and feared of viral invaders, and those most widely identified as bioterrorism threats, are Hemorrhagic Fever viruses, like Ebola and Marburg. In vitro tests against these viruses showed 100% infection inhibition at relatively low dosages. The $EC_{50}$ value for this member of the FGI-103 compound family is at or below 0.050 uM, a remarkably low dose.

Many compounds shown to be effective against viral challenges in vitro lose potency, or fail to exhibit similar prophylactic or therapeutic efficacy, in vivo. There are a variety of reasons for this—fundamentally, mammalian systems are complicated—no matter what route of administration is used, there are fundamental obstacles to delivering in vivo the same type of anti-viral effectiveness frequently observed in vitro. As demonstrated in FIG. 25, however, Compound 723 is dramatically effective in vivo. Administered IP to 10 mice, 723 provided complete protection at 10 mg/kg, when administered at the time of challenge (day zero) as well as day 2 and day 5. In contrast, the vehicle minus the active agent 723 experienced near 100% fatalities.

Importantly, as depicted in FIG. 26, a single dose of 10 mg/kg at day one of infection provided 90% protection on challenged mice, demonstrating therapeutic as well as prophylactic utility. Even at half that dosage, 5 mg/kg, survival was at 25% levels, while the vehicle in the absence of 723 gave 100% mortality. FIG. 27 is in some ways even more remarkable, demonstrating the effectiveness of a single dose at the 10 mg/kg level on day 4 of infection—that is, 4 days AFTER challenge (inoculation with mouse adapted EBOV). Clearly, Compound 723 offers important opportunities in terms of treating viral infection, therapeutically as well as prophylactically.

As shown in FIG. 28, the same effectiveness in vivo is demonstrated against Marburg virus, another bioterrorism threat. As with Ebola, treatments at 10 mg/kg at days 0, 2 and 5 gave 100% protection, measured in terms of survival. Clearly, Compound 723, as well as many members of the FGI-103 family of compounds, shows the same kind of activity in vivo as are obtained for it in vitro.

An important parameter in developing a prophylactic or therapeutic agent for administration to mammals, particularly humans, is the time the agent remains in the blood, frequently measured as serum concentration. The time course for serum concentration for 723, for mice, receiving 10 mg/kg of 723 at time 0 and 12 hours, is set forth in FIG. 29. As shown, serum concentration levels drop rapidly, giving a $t_{1/2}$ of 2 hours. By four hours, the serum concentration has fallen below the $EC_{50}$ value for Ebola, and by 8 hours plus, below the $EC_{50}$ value for RSV and PIV. Yet, as shown, this compound provides effective protection against these viruses, at a 10 mg/kg dosing regimen. This may be explained by concentrations of the agent found in specific tissues. Thus in FIG. 30, concentrations in the liver and kidney are high, while concentrations in the spleen and the heart are relatively low. This may suggest that viruses that target hepatic and renal tissues are more effectively protected against by even very low doses of 723.

FIGS. 31 and 32 show the same type of data for the guinea pig model. FIG. 31 gives a $t_{1/2}$ of 4 hours for 723 in the guinea pig, while dosing, either at 0 and 24 hours, or 10 doses, show a similar tissue accumulation pattern. Thus, this agent may have particular effectiveness against viruses that target the lungs, liver and kidneys.

Agents of the type addressed, that have effectiveness in treating infection in a large number of mammalian hosts against a range of viruses are always desirable. The FGI-103 family of compounds presents just this type of opportunity. It is always most desirable, however, to provide an agent that can be taken orally, and provide protection. This permits more widespread distribution, and greater follow-through—patients are more easily dosed with an oral formulation than with those that require inoculation. To demonstrate the suitability of 723 and other 103 compounds for oral administration, compound 723 was "derivatized" to provide a prodrug that would be digested to provide the active agent, by modifying the amide groups with hydroxy moieties, as shown in FIG. 33. Administration of the prodrug in the same 10 mg/kg dosage gave serum levels at or above those achieved by IP administration in the same time frames. This strongly indicates that the FGI-103 compounds can be administered IV, IM, IP and orally, at or about the same effective dosage levels.

Safety is always a paramount consideration when formulating an agent to be administered to mammals, including humans. $CC_{50}$ (a measure of a compound's cytotoxicity) is thus a parameter of fundamental importance. As shown in FIG. 34, based on cell based assays against a wide variety of cells, $CC_{50}$ values for 723 were well above safety thresholds. The safety of the compound, per se, was demonstrated in $LD_{50}$ (lethal dose) studies, in vivo, as reflected in FIG. 35. At or above effective dosage levels, up to 100 mg/kg, the compound is well tolerated. 200 mg/kg administered on day zero constituted a lethal dose. Below that value, Dosing had little or no impact on weight over time, as also shown in FIG. 35.

The compounds of FGI-103 as a group are not all novel compounds, per se. Many have not been prepared in pharmaceutically pure condition, or in formulations suitable for administration (suspensions and solutions in a pharmaceutically acceptable carrier). The use of 723 and other FGI-103 compounds requires a synthesis method that facilitates this kind of pharmaceutical preparation. A suitable synthesis scheme is set forth in FIG. 36, although other routes to the compound may be used. The materials employed, and yields realized, permit the maintenance of good laboratory practices, or GLP, in the synthesis and formulation of pharmaceuticals including 723 as an active agent against viral infection FGI-103 Compound 365

Compound 723 is a four ring compound of the general formula Y—X—$Y^1$ described above, with two fused ring systems. As shown in FIG. 37, Compound 365, Quino[8,7-h]quinoline-1,7-diamine,N,N'-bis[3-(dimethylamino)propyl]-3,9-dimethyl-tetrahydrochloride (as a salt) is another compound satisfying the narrowed formula for the FGI-103 family of compounds, but of structure distinctly different from 723 in that the "X" component is a four fused ring system. As reflected in the data set forth in FIG. 37, however, Compound 365 shows the same kind of prophylactic/therapeutic effectiveness against a wide variety of viruses, safe in a wide variety of cells, and providing 100% protection against dangerous bioterrorism threat viruses in vivo, including Ebola. This agent has been tested and shown efficacy against HIV, HCV, Lassa Fever virus, SARS, Rift Valley virus, PRRS, Dengue, Bovine Corona virus, Ebola and Marburg virus, crossing a wide variety of virus families. Some of this information is summarized in FIG. 38, together with concentration, toxicity and safety information. As shown, in many environments, 365 is even more active than 723.

Hepatitis C virus is a blood born pathogen for which no known vaccine exists. The effectiveness of 365 against HCV is shown in FIG. 39, where, at about 1 uM, 365 gave complete inhibition of the virus (an absence of the luciferase signal indicates an absence of the virus) on Huh 7 Human hepatoma cells. 365 gives a safety index of 13 against HCV, and thus provides a potent agent against this virus which is otherwise addressed by a variety of post-infection support steps, but is also associated with chronic liver disease.

Compound 723 was tested against Dengue Fever. This important virus, and potential terror weapon, is also strongly inhibited by Compound 365, at very low levels, as reflected in FIG. 40. Again, one aspect of Dengue fever that has confounded prior treatment agents, substantial variation among serotypes, is of no consequence for the FGI-103 family compounds. Like 723, and as shown in FIG. 40, 365 is effective against each of the Dengue serotypes with remarkably similar results.

Ebola is of course an important virus to be evaluated. Ebola constitutes a potential bioterrorism threat, and is endemic in parts of the world where humans with no native protection may be dispatched. 365 shows powerful inhibition of Ebola virus. As reflected in FIG. 41, in a Vero cell-based assay, 365 gave 100 percent inhibition at low levels, below 10 uM. Ebola has a similarity to rabies and measles, as well as the Paramyxo and Pneumoviruses, again indicating the broad applicability of 365 as an agent in the treatment of a wide variety of viruses.

As noted with Compound 723, perhaps no virus has received as much attention as HIV in terms of potential treatments and cures. In FIG. 42, data presented by graph and table shows 365 to be a potentially powerful inhibitor of HIV, achieving 100% inhibition at modest concentrations. This value is far below the $CC_{50}$ value of 365, providing a large safety index which is uncommon in potent drugs targeted against HIV.

The development of anti-viral agents against viruses that infect humans is of paramount importance. Of similar importance is effectiveness against PRRS and similar viruses that destroy billions of dollars of livestock every year. FIG. 43 reflects the high degree of effectiveness of 365 in inhibiting this virus. With an $EC_{100}$ of only 3.2, this is a strong potential agent.

Compound 365 shows similar efficacy against Rift Valley Fever Virus, providing 100 percent inhibition (zero viral particle release) at safe values far below the $CC_{50}$ index for this compound. With an $EC_{50}$ of only 0.37 uM, this agent provides a large safety index of 30 for the treatment of RVFV. This data is reflected in FIG. 44, which presents by graph and table the results of Vero cell assays. In similar assays, both Marburg Virus and Lassa Fever Virus were shown to be suppressed by 365 administered to infected vero cells. The results for this testing, demonstrating the suitability of 365 both as a broad-based anti-viral agent for the treatment of human and mammalian diseases, and an anti-bioterrorism agent, is reflected in FIGS. 45 and 46.

SARS is a virus that swept through parts of China and Asia, without prevention or treatment other than supportive treatment. A related virus, Bovine Corona Virus, presents a commercial threat. Both are inhibited by 365, without crossing the "Safety Barrier" by 365. While more potent agents are typically less safe, 365, like the other compounds of the FGI-103 family, presents opportunities to treat viruses in humans and commercially important mammals without sacrificing safety.

Like Compound 723, Compound 365 has also been shown to be effective in vivo as well as in vitro. As noted above, a method of therapeutically treating Ebola at this time is unknown. Most "treatment" consists of supportive measures in hopes the body's natural immune systems can address the virus. As shown in FIG. 48 at a low dosage of 5 mg/kg, 365 was shown to be effective as a therapeutic agent, providing 100% protection when administered one day after challenge of 10 mice with mouse adapted Ebola Virus. Importantly, as shown in FIG. 48, this agent exhibits a typical dose response curve when administered in this way, providing reduced protection at reduced dosages.

Although 365 did not ultimately improve survival outcomes for mice challenged with pox virus (when administered at day 0, 2 and 5) it did uniformly extend survival times. Extending survival time, as noted above, is of importance in treating agents that have no known inhibitors, providing time for the body's natural defenses to work against the invader. The effectiveness of 365 in extending survival times against pox virus is set forth in FIG. 49.

As with 723, 365 is intended for treatment of humans, and commercially or veterinarily important mammals. Accordingly, safety is a paramount concern. As shown in FIG. 50, at amounts well above potential dosage levels, given the activity of 365, on up to 25 mg/kg, all animals (mice) survived, and their weight was not significantly impacted by administration of 365.

Like 723, once administered, 365 leaves the serum relatively rapidly, the time course of serum concentration following a 5 mg/kg dose given to BALB/c mice being reflected in FIG. 51. FIG. 52 also displays cytokine levels over the time course following administration of a 5 uM dose, this time to PBMC. Cytokine level perturbation can be an indication of a potentially dangerous drug. As reflected in FIG. 52, cytokine levels for the major cytokines were not substantially different than that exhibited in response to the agent-free vehicle.

As discussed above, 365 presents strong anti-viral activity as a therapeutic, and prophylactically, against a wide variety of viruses. To provide a source of pharmaceutically pure and acceptable 365, and prepare suitable formulations including pharmaceutically appropriate suspension and solutions, a synthesis scheme must be provided that can be practiced in accordance with GLP. Such a scheme is set forth in FIG. 53. A short 4 step procedure yields 365, a potent inhibitor of a wide range of viruses.

FGI-103 Compound 510

Compound 510, benzenecarboxylmidamide,4,4'-(2,5-thiphenediyl)bis (dihydrochloride as a salt) has a performance so similar to 723 that it is sometimes referred to as FGI's "backup" 103 compound. And yet, as reflected in FIG. 54, it is very different in structure from both 723 and 365. Instead of four rings, it employs a three ring non-fused structure wherein S is a hetero ring atom. IT conforms to the Y—X—$Y^1$ formulation described above, however, and like so many members of this class, exhibits potent activities as an anti-viral agent. It is effective, as reflected in in vitro testing against a wide variety of viruses including Ebola Virus, Lassa Fever Virus, Cowpox, West Nile Virus, RSV and PIV, and has been shown to be safe when used in a wide variety of cells. Spectacularly, like the other FGI-103 compounds discussed above, it confers 100% protection against lethal challenge with Ebola Virus, used prophylactically or therapeutically. It also provides protection against Marburg Virus. Other than the FGI-103 compounds, no other agent has been demonstrated to be so effective against potent viral agents. This data is summarized in the table of FIG. 55, showing again both efficacy and safety for use of this agent against a wide variety of viruses drawn from many virus families.

As has been previously discussed, Hemorrhagic Fever Viruses like Ebola and Marburg Virus present dangerous opportunities as terror weapons. The provision of an inhibitory agent that is safely tolerated by humans is therefore an important goal. 510, like its sister compounds, provides 100% inhibition of these viruses, as measured in terms of cell survival, reflected in FIG. 56. These cell based assays are conducted on Vero cells. This performance strongly suggests 510 should be effective against the same virus families the other FGI-103 compounds have measured or suggested activity against, including measles, rabies, RSV, PIV and HMPV. (human metapneumovirus, and RNA virus).

Figure 57:
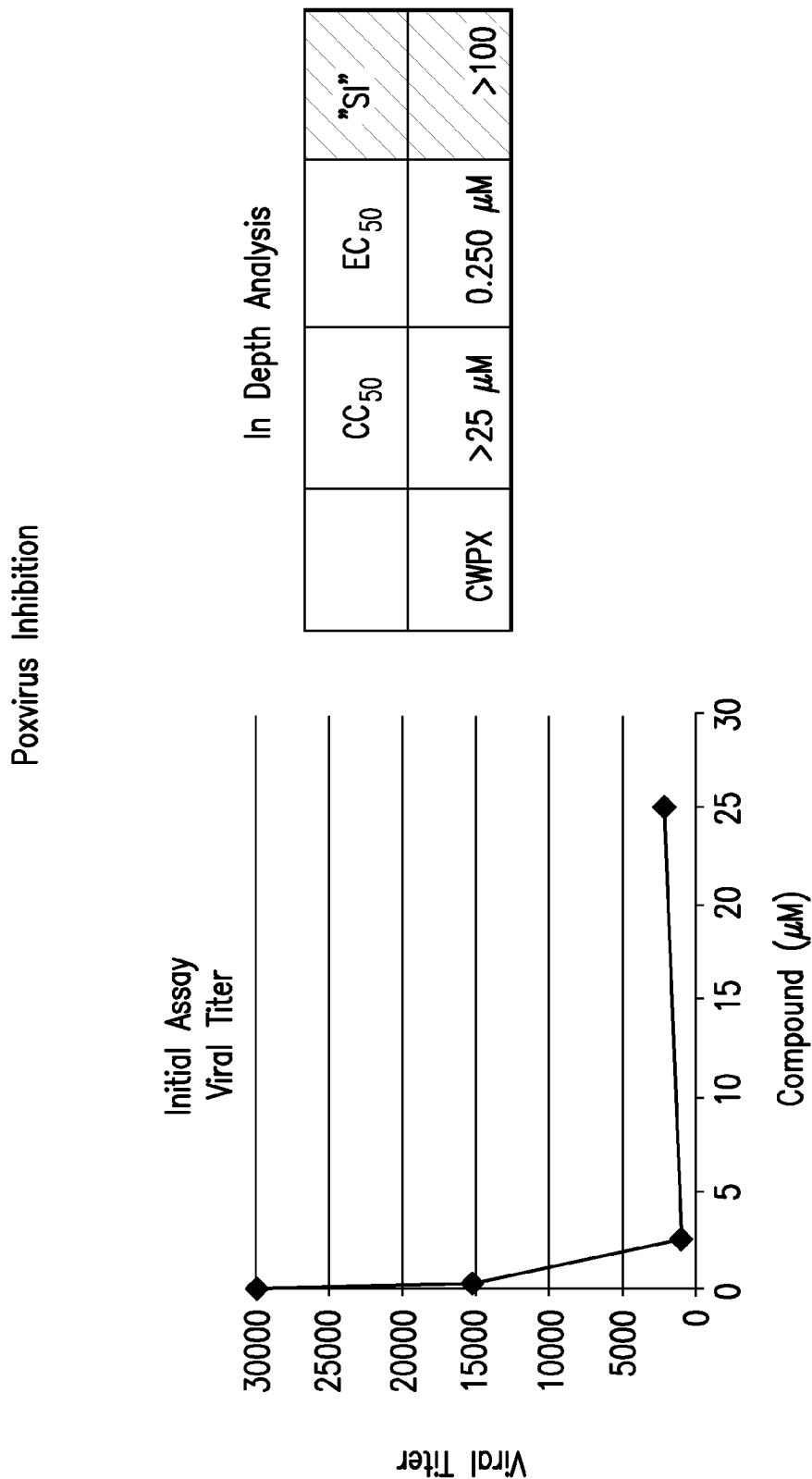
Figure 58:
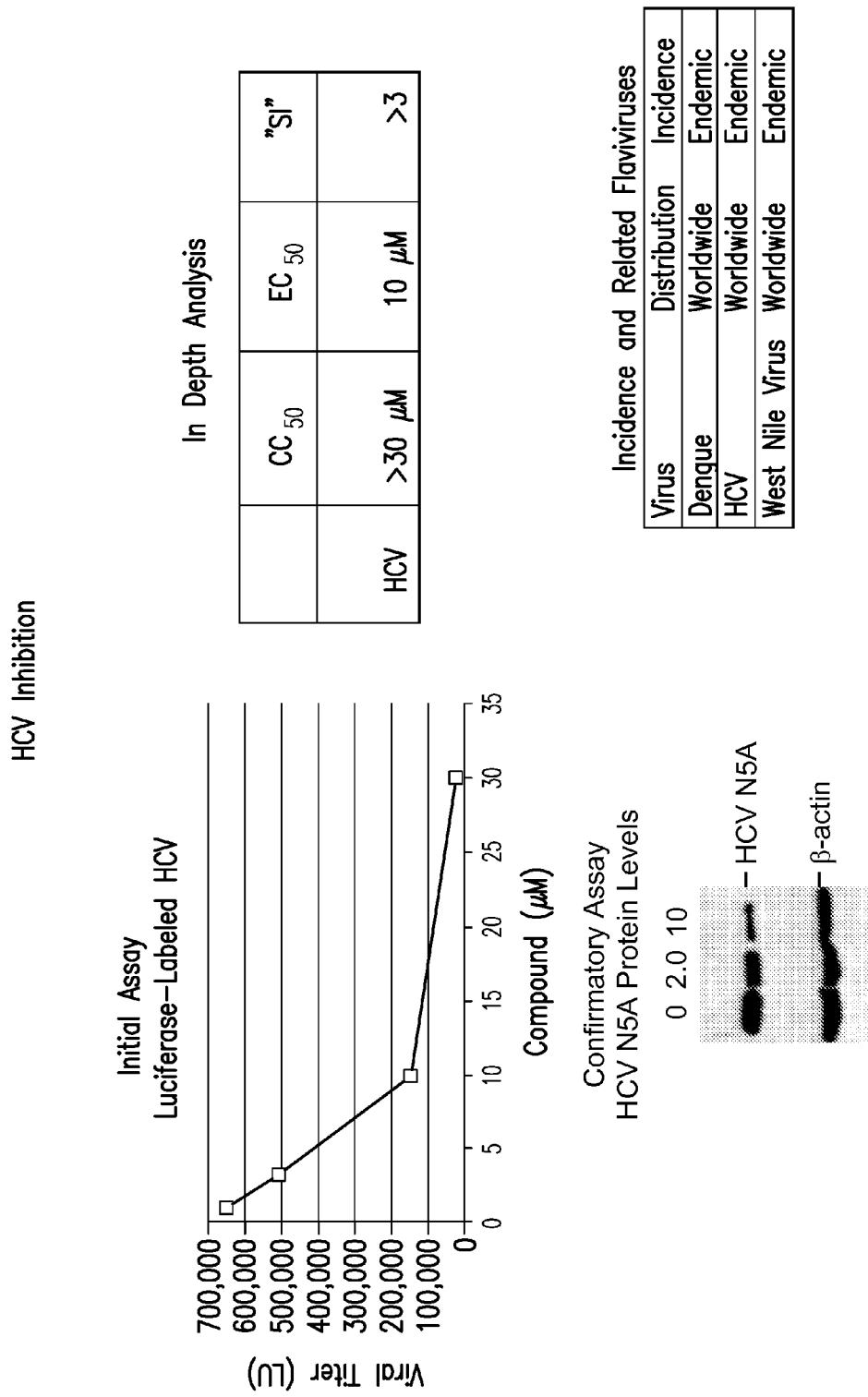

As shown in testing for 723 and 365, inhibition of pox virus is an important and ordinarily difficult goal. 510 provides strong inhibition of pox virus, with low viral titers on Vero cells at modes dosages. The testing, reflected in FIG. 57, gives a low $EC_{50}$ value of about 0.250 uM, and a large safety index. Similar inhibition of HCV is shown in FIG. 28, with viral titers going to zero at about 30 uM over a 72 hour time course. TO confirm the absence of viral activity, blotting demonstrating the reduced product of HCV n5A proteins was conducted, and is reflected in FIG. 58. Like HCV, related viruses like Dengue and West Nile Virus should be subject to treatment with 510 on much the same conditions. Effectiveness against West Nile Virus is reflected in the data set forth in FIG. 59, showing 100 percent inhibition. Like its sister compounds, 510 is also shown effective against Lassa Fever Virus and Paramyxoviruses—the cell based assay data being shown in FIGS. 60 and 61, respectively.

Like 723 and 365, demonstration of in vivo activity paralleling that predicted by in vitro testing is of importance if 510 is going to be an effective anti-viral agent. 510 does indeed give the same sort of in vivo protection against the same virus targets, conferring 100% protection when administered at 10 mg/kg at the time of, and days 2 and 5 following, Marburg Virus challenge. This data, set forth in FIG. 62, clearly demonstrates the effectiveness of 510 as an antiviral agent. Used therapeutically, administered 2 days post infection, 510 provided protection against Ebola virus in a dose response fashion, as shown in FIG. 63.

Like the other members of FGI-103 compounds, 510 is susceptible of simple synthesis from commonly available starting materials that will make it practicable to provide pharmaceutically pure compound, and pharmaceutically acceptable preparations including solutions and suspensions in a pharmaceutically acceptable carrier. A simple synthesis scheme of this compound is set forth in FIG. 64.

FGI-103 Compounds

A Potential Method of Action—Caspase Inhibition

It is rare that an initial compound identified by testing and structure, as is the case for the FGI-103 compounds, is the best possible compound of that type. It is frequently the case that derivatization of the starting compound, to embrace small substituent and substitution additions and subtractions, may give improved efficacy in the treatment of one or more viruses in one or more mammalian hosts. Actual examples of derivatization follow. Knowledge of a possible method of action, however, may guide the person skilled in the art in the proper course for derivatization. While the inventors are not bound by this theory, there is increasing evidence that the FGI-103 compounds act by selectively inhibiting certain Caspase enzymes (proteases) that are vital to virus particle assembly—that is, in the conventional life cycle of the virus, intervening late in that cycle, blocking some proteolytic action necessary for the virus to mature or be brought to the cell surface. It is not unreasonable to conclude that a critical digestion step where the virus "hijacks" a protease on the way to the surface is somehow inhibited by the FGI-103 compounds.

Caspases have traditionally been studied in connection with their role as effectors of apoptosis and inflammation. However, recent evidence has also pointed to additional roles for caspases in other cellular processes, such as cellular proliferation and cell-cycle progression. See, e.g., Los M., et al., Caspases: more than just killers? *Trends Immunol.* 22(1): 31-4 (2001); Algeciras-Schimnich A, et al., Apoptosis-independent functions of killer caspases. *Curr Opin Cell Biol.* 14(6): 721-6 (2002); Launay S., et al., Vital functions for lethal caspases. Oncogene 24(33): 5137-48 (2005. Current research at FGI, described herein as a basis in part for the present invention, suggests yet another role for caspases, wherein the protease activity of caspases is utilized by viruses during their infection cycle. Indeed, caspase activity appears to be critical or essential for viral infection by a variety of virus types in light of evidence, described herein, showing that FGI-103 caspase inhibitors interfere with and/or block the ability of viruses to successfully infect host cells. Therefore, it is generally advanced herein that various compositions and methods for inhibiting caspases may be effective in preventing, treating, and/or managing viral infection and disease.

Figure 1:
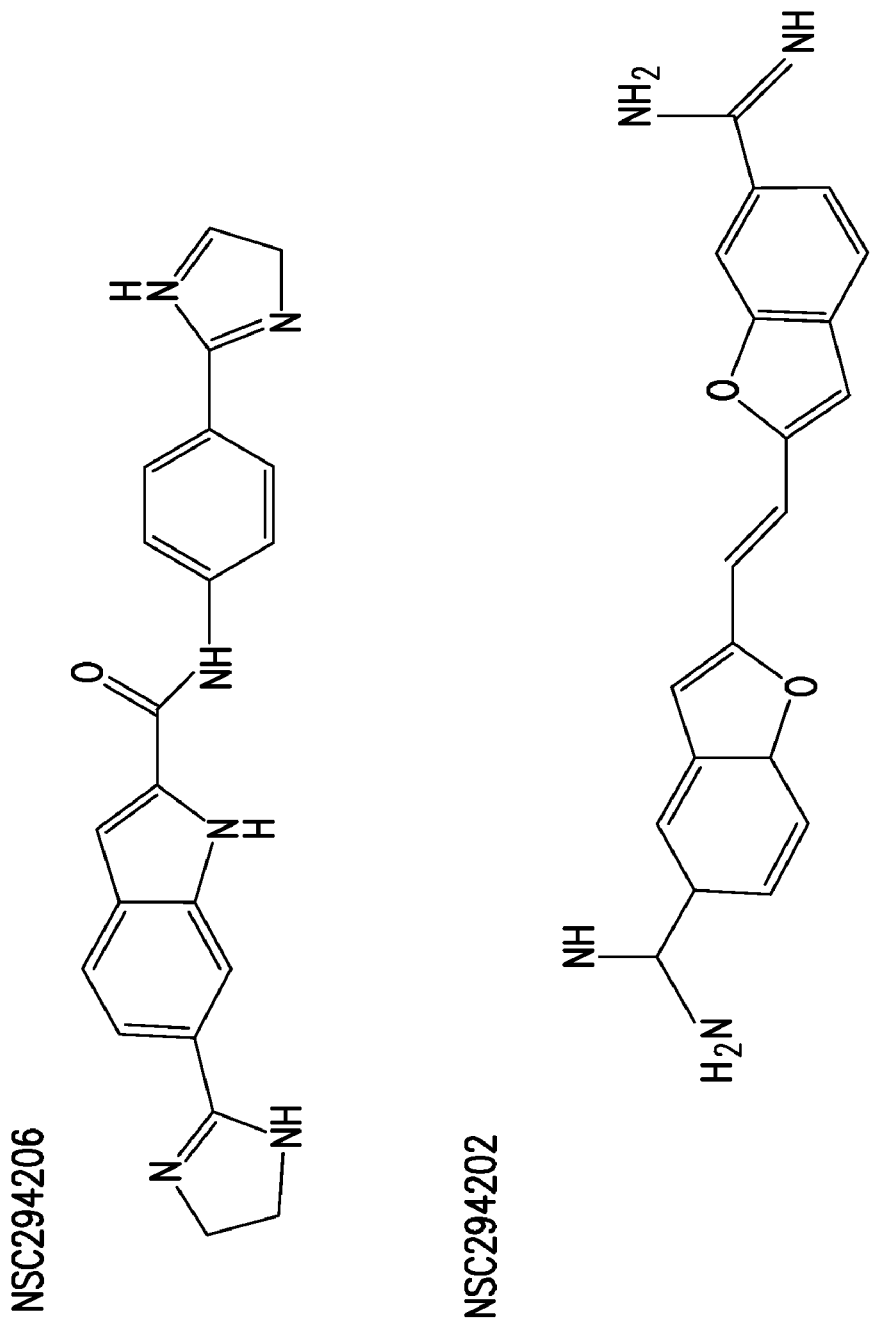
FIGS. 1-4 provide structural formulae of active compounds of this invention.
Figure 2:
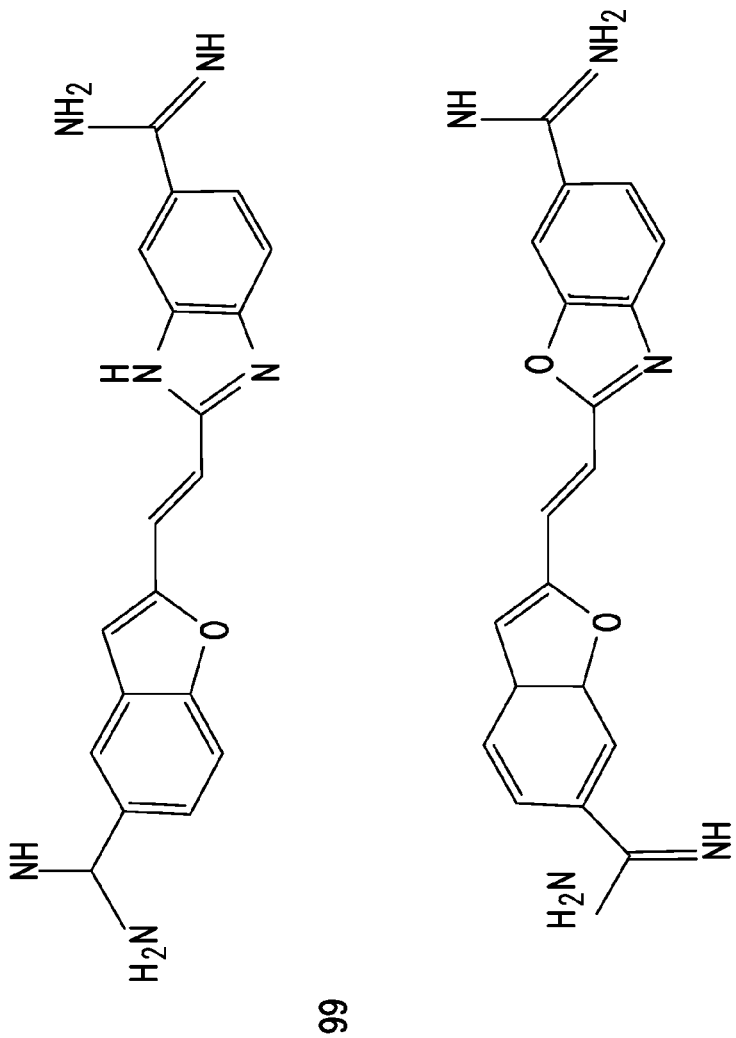
Figure 3:
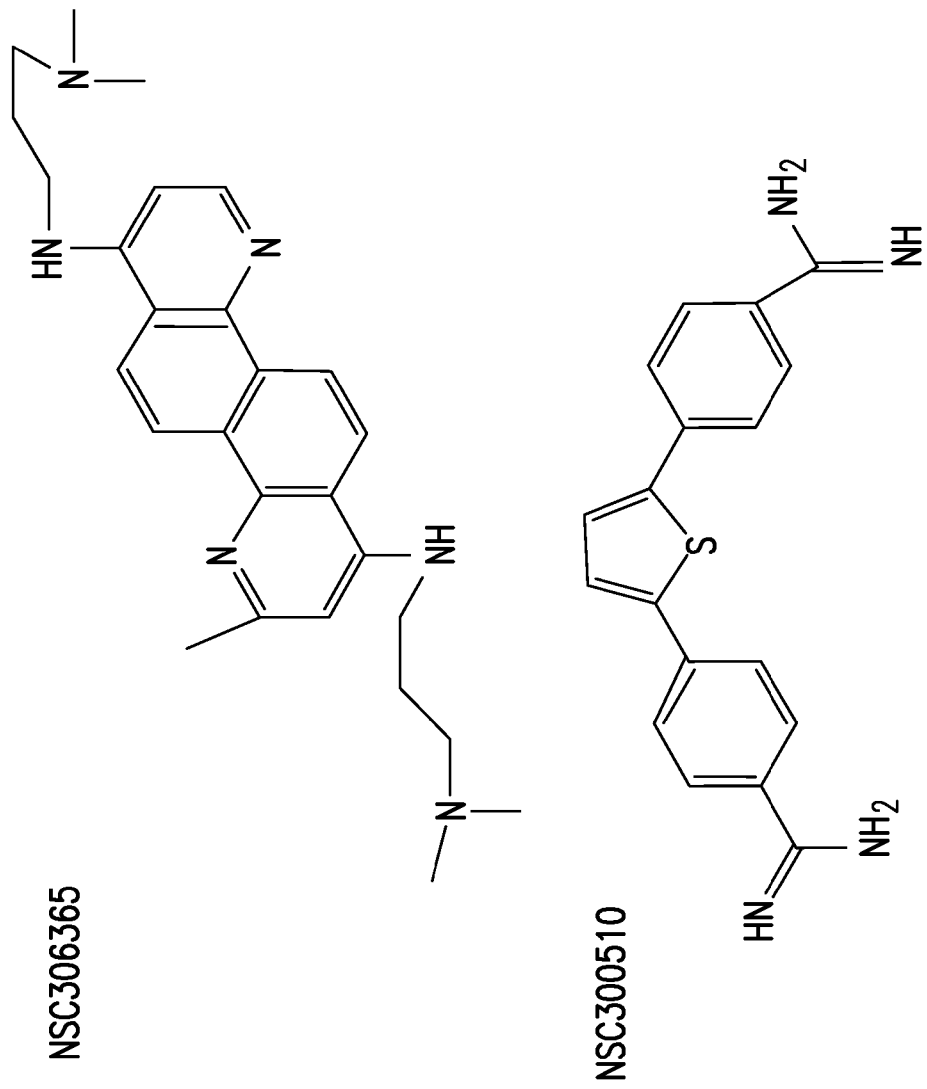
Figure 4:
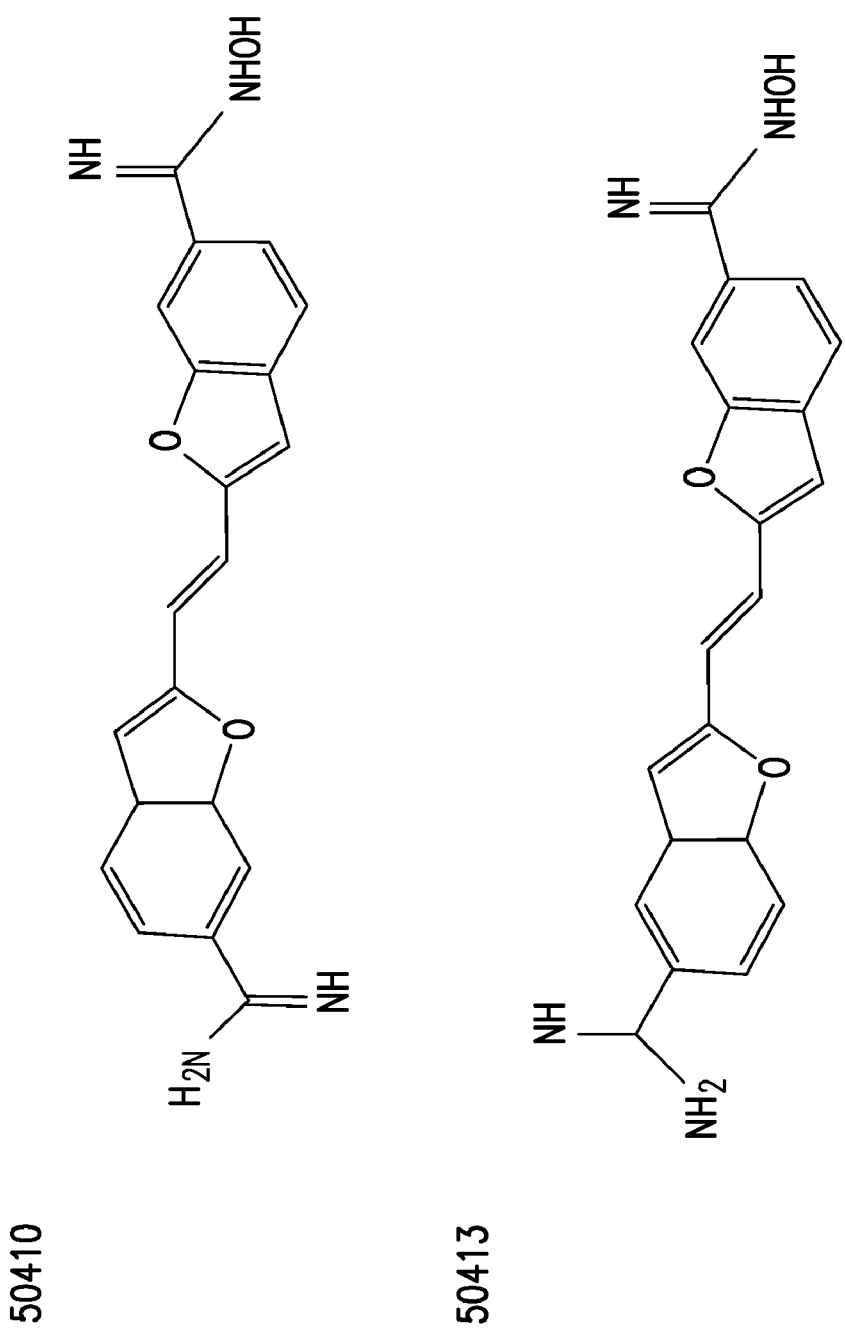
Figure 5:
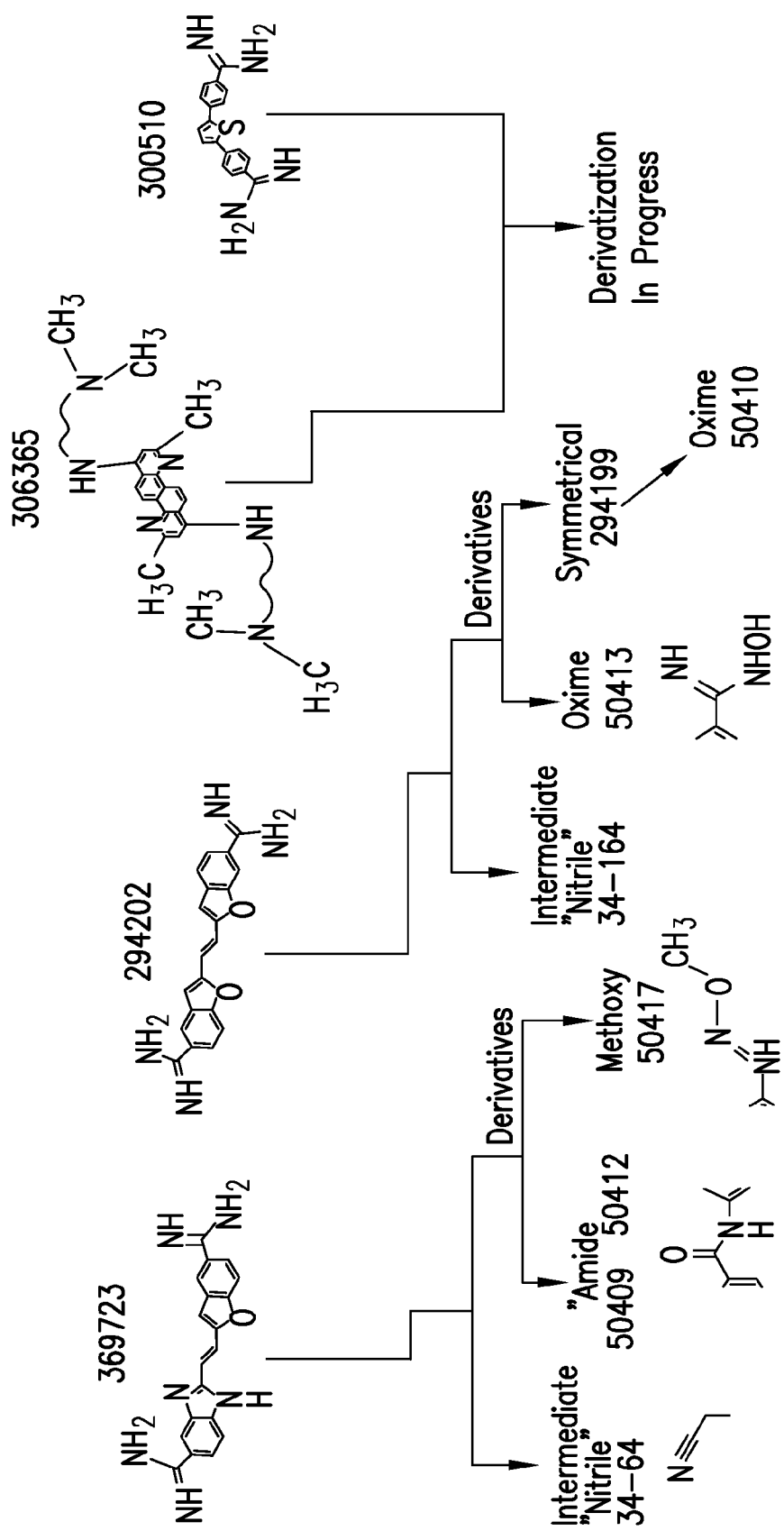
FIG. 5 provides certain common chemical structure units of the compounds of this invention.
Figure 8:
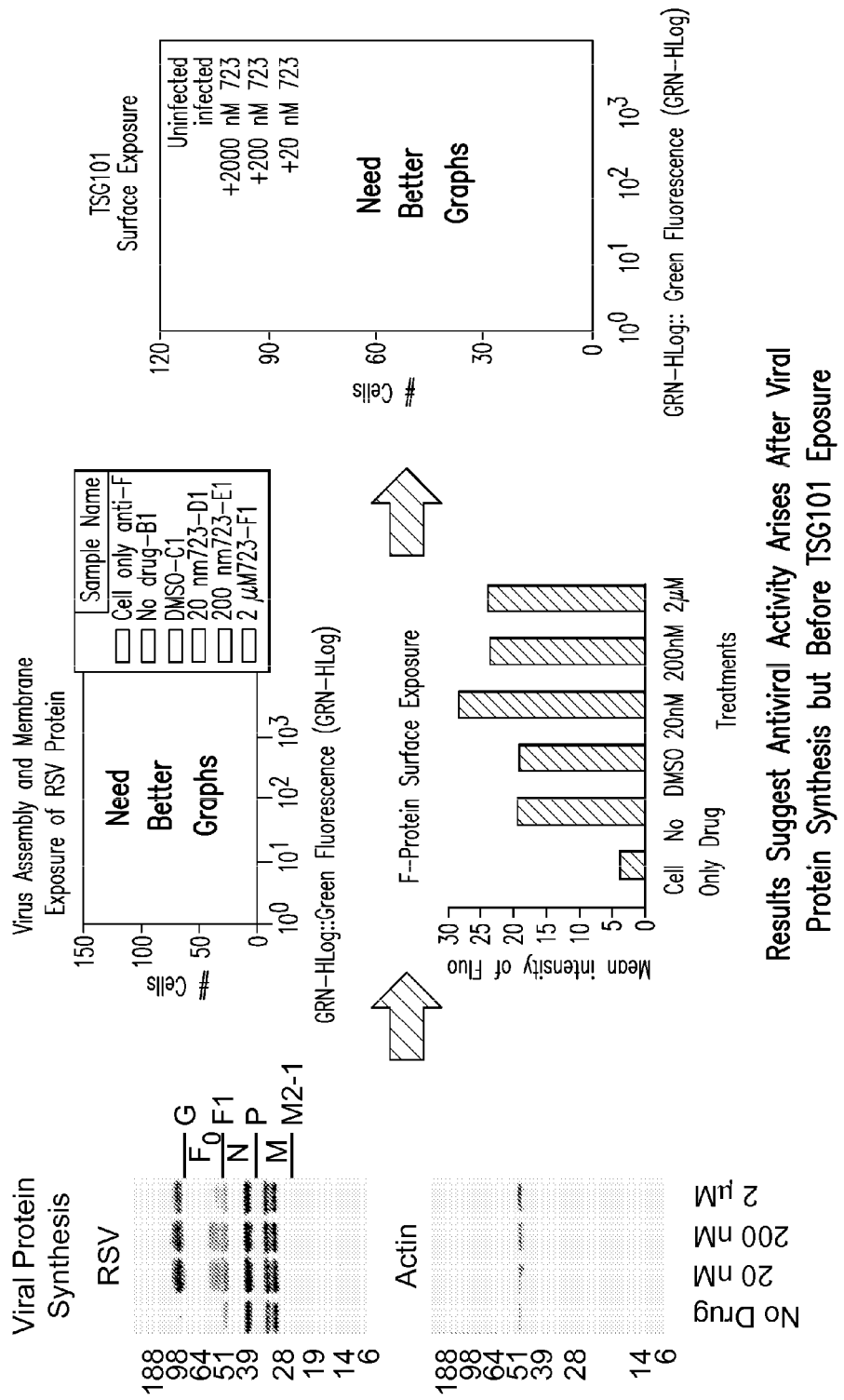
FIG. 8 provides a collective summary, graphically, of data obtained using in vitro testing of FGI-103 compound 723 in particular that suggests the small molecule active agents of this invention are effective in inhibiting a pathway after viral protein synthesis is complete.
Figure 9:
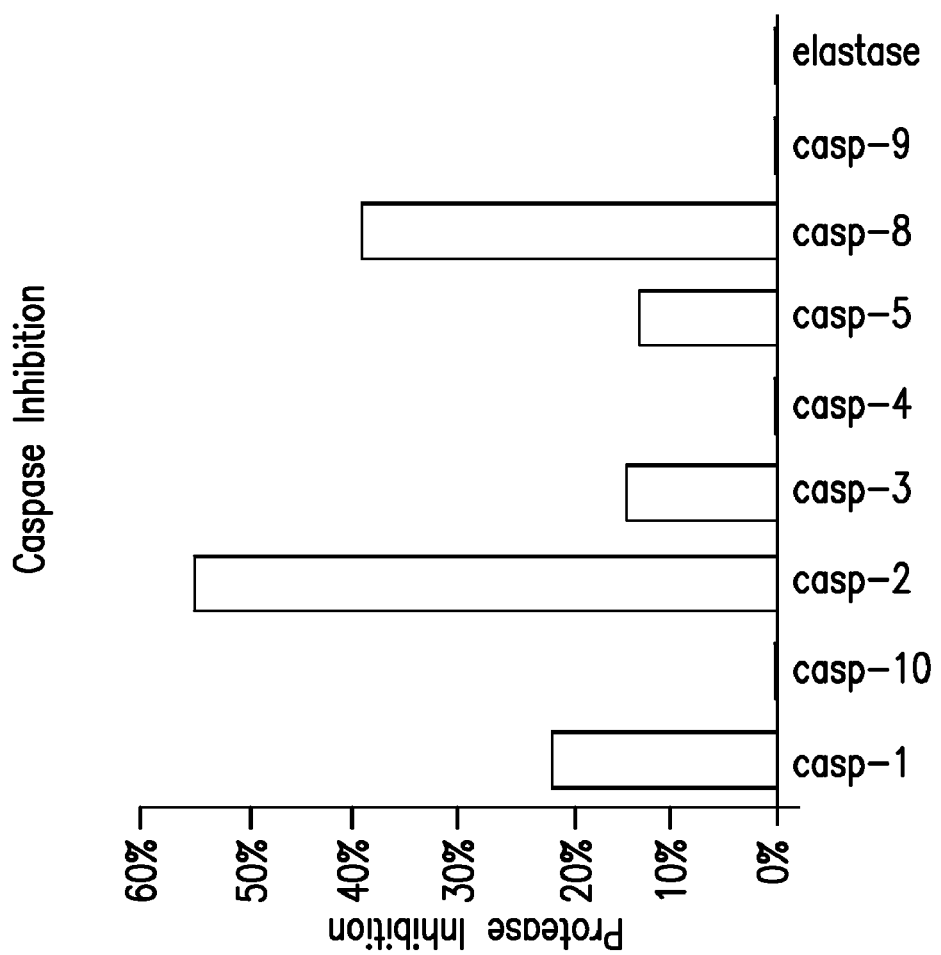
FIG. 9 is also based on testing, in vitro, of the small molecules of this invention, demonstrating that the FGI-103 molecules selectively inhibit the activity of certain sapace enzymes, enzymes that are protease.

Many of the FGI-103 compounds tested selectively inhibit caspases 2, 3 and 8, and to a lesser degree, Caspase 1. Collective values for this inhibition as a family are set forth in the graph of FIG. 9. This, taken together with the data obtained and presented in FIG. 8 strongly indicates that the antiviral action of the FGI-103 compounds intervenes in the virus life cycle after viral protein synthesis is complete, or at least all major viral protein synthesis, but before presentation on the surface of the cell by binding to TSG 101. As explained in the literature, TSG 101 is a member of the family of ESCRT proteins that are used by viruses to escape the cell. Inhibition of TSG101-virus interaction is effective in inhibiting viral budding. This inhibition phenomenon, through the use of TSG101-directed antibodies, is disclosed and claimed in U.S. patent application Ser. No. 10/675,979 (allowed). While the nature of the anti-viral agent in that application, an antibody, is drastically different from the small molecule agent of the FGI-103 compounds of this invention, the allowed application does provide a description of the interaction between the virus and TSG 101, allowing the inventors to point to antiviral activity that occurs prior to complexation by the virus with TSG101.

The profile for Caspase inhibition by FGI 510 is specifically given in FIG. 65, again showing selective inhibition of Caspase 2, 3 and 8, as well as Caspase 1 to some degree. This selective inhibition is given in table form in FIG. 66. Note the difference in $IC_{50}$ values for the Caspase targets inhibited, as compared, e.g., with Caspase 9. This can be combined with knowledge of Caspase crystal structure, to hypothesize a possible "fit" for Compound 510 and the FGI-103 compound family as shown in FIG. 67 which would help to explain the selective inhibition of Caspase 8 and Caspase 3 over other Caspases. This "fit" matches, depending on derivatization, the compounds of the FGI-103 family as expressed in terms of the Y—X—$Y^1$ structure. A similar modeling exercise is reflected in FIG. 71, this time using Compound 723 as the anti-viral agent. Like the fit for 510, this suggests that 723 may block the site necessary for virus/Caspase interaction, inhibiting virus particle maturation.

Figure 7:
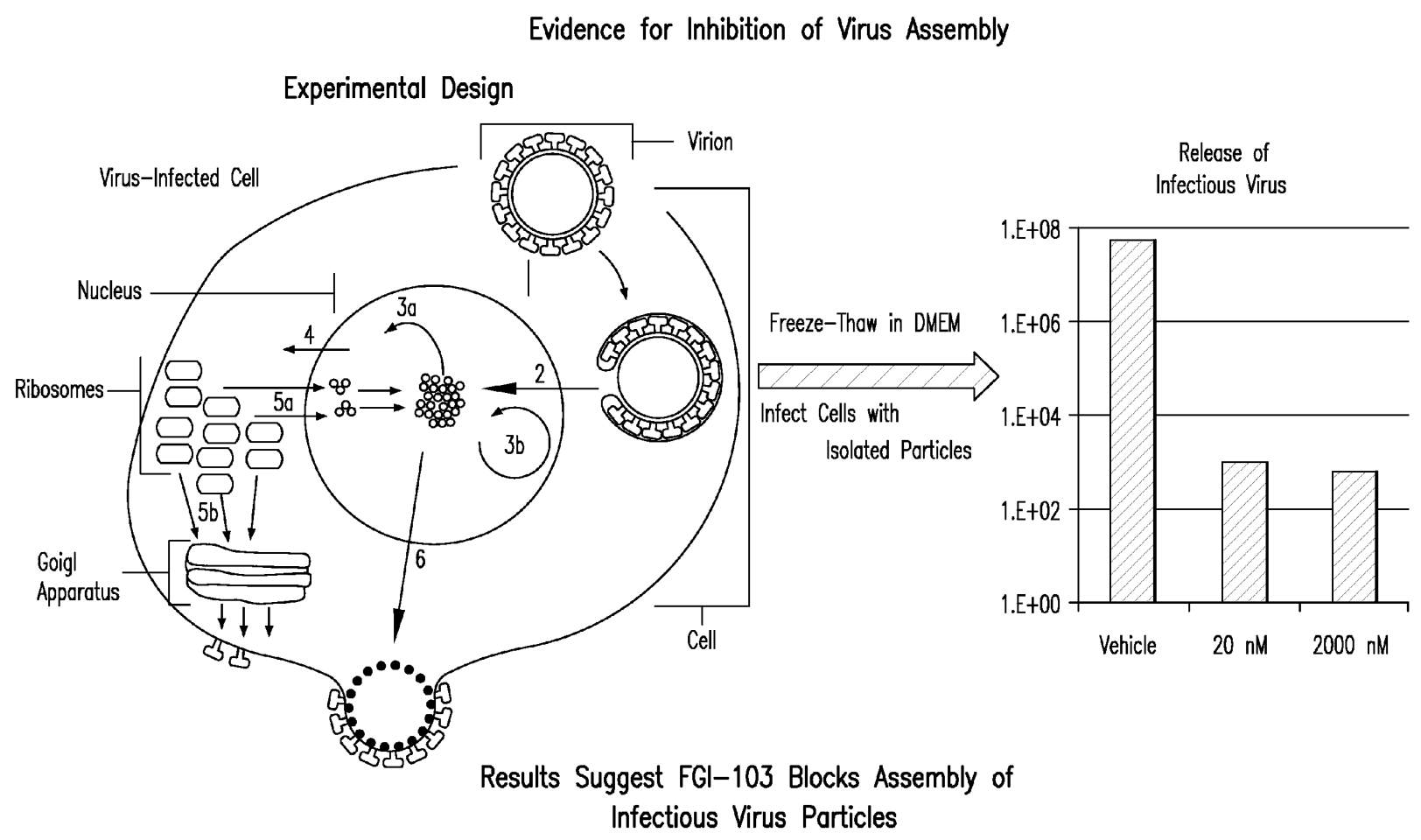

FIG. 7 gives data on viral particle propagation generically for these compounds, and FIG. 68 specifically for Compound 510, demonstrating that when cells are infected with isolated particles, the vehicle, in the absence of the FGI-103 compounds, does not block viral propagation, but the FGI-103 compounds, and 510 in particular, do in fact inhibit the formation of infectious viral particles. Again, this strongly suggests that the FGI-103 compounds intervene in the life cycle of the viruses after viral protein synthesis but before being carried to the surface, perhaps blocking a critical enzymatic digestion step required before the inhibited viruses can escape the infected cell.

The timing of intervention by FGI-103 compounds is reinforced by the data obtained from the MDCK cell assay that is reflected in the data set forth in FIG. 69, prepared using 510. The infection pathway and timing of RSV is well known, and is set forth in the lower right corner. As can be seen, at any time during the viral assembly, administration of the FGI-103 compound inhibits viral particle formation, until such time (after the $18^{th}$ hour or so) when the virus is carried to the surface and buds. This idea is reinforced by the data set forth in FIG. 70, reflecting inhibition of induced apoptosis in the presence of 723. Accordingly, a method of inhibiting or treating viral infection lies in administering an agent that selectively inhibits Caspases used by the virus for maturation, particularly Caspase 8, 3 and 2, but not other endogenous Caspase activity (which would be inimical to the cell).

Derivatization—FGI 103 Compound 365 as an Example

As noted above, given the identification of a particular method of action, and desired intervention (selective Caspase inhibition to prophylacitcally and/or therapeutically treat virus infections in mammals) it maybe become desirable to derivatize one or more core molecules of the FGI-103 Compound family, in order to improve efficacy, improve safety or tolerability, to tailor a compound to specific situations, modes of administration or viruses, etc. Derivatization, per se, is a well established methodology known to those of skill in the art. To further demonstrate how an FGI-103 compound may be derivatized however, Compound 365 was subjected to a series of derivatizations, as described below. These are offered not to identify compounds of improved or selective activity, but rather to demonstrate the susceptibility of the FGI-103 compounds to derivatization.

Synthetic Routes for 306365 (BG9), and its Derivatives (BG11, BG15, BG16, BG17, BG20)

Instrumentation

IR: Thermo-Scientific Nicolet 6700 FT-IR Diamond Crystal.

NMR: $^1H$ and $^{13}C$ NMR spectra were recorded on a

Varian Gemini-200 spectrometer (at 200 and 50 MHz, respectively), and

Bruker Ultrashield Advance III spectrometer (at 500 and 125 MHz, respectively), in the indicated solvent using TMS or TMS-Na salt as internal standard.

Chemical shifts are expressed in ppm (ä) values and coupling constants (J) in Hz.

ESI MS spectra of the synthesized compounds were recorded on an Agilent Technologies 6210 Time-of-Flight LC/MS instrument in the positive ion mode using $CH_3CN/H_2O=1/1$ with 0.2% HCOOH as the carrying solvent solution. The samples were dissolved in pure acetonitrile (HPLC grade). The selected values were as follows: capillary voltage 4 kV; gas temperature 350° C.; drying gas 12 l min-1; nebuliser pressure 45 psig; fragmentator voltage 70 V.

General Methods

All steps were performed at least in duplicate. The target compounds were characterized by IR, $^1H$ and $^{13}C$ NMR, HPLC-ESIMS spectra (bases and salts). Melting points of the salts were =>280° C. All salts were water soluble.

Synthesis of BG9

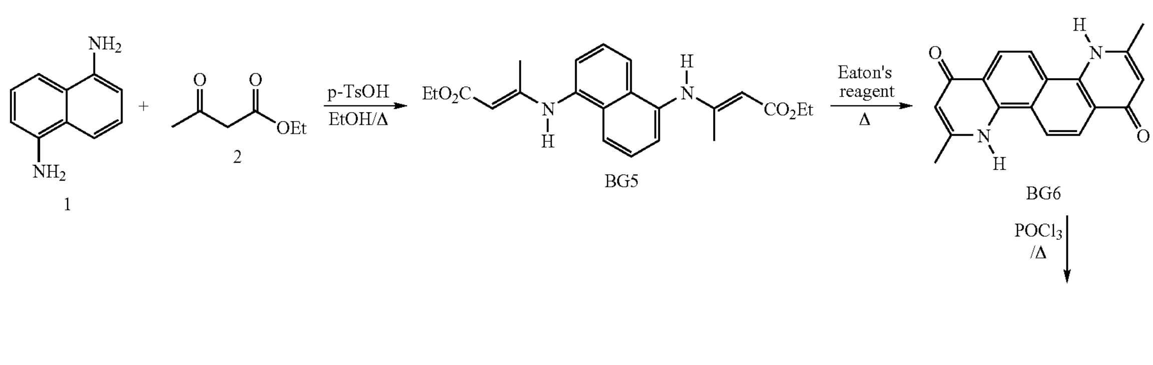

1 2 BG5 BG6

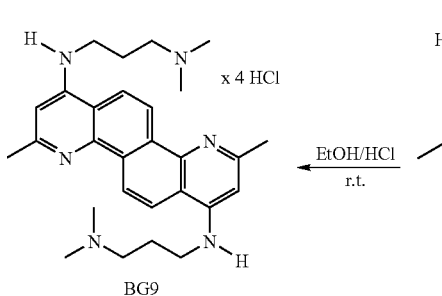
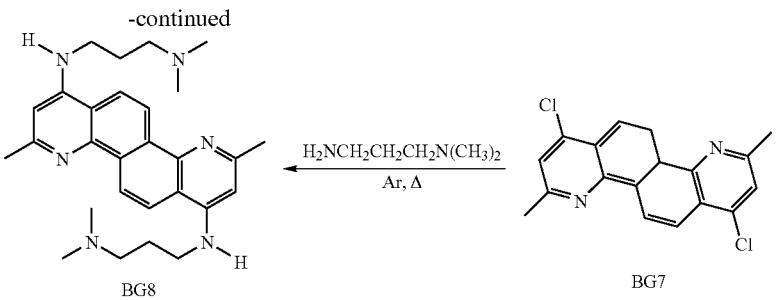

A suspension of 1,5-diaminonaphthalene 1 (5.0 g, 31.6 mmol), ethyl acetoacetate 2 (40 mL, 313.5 mmol) and p-TsOH (2.38 mg) in 250 mL of anhydrous ethanol was heated to reflux in a two-neck round bottom flask equipped with Dean-Stark trap filled molecular sieves (4 Å). After heating for 4 hours in an oil bath at a temperature of 120° C. with stirring, the mixture was cooled to room temperature and evaporated to dryness (upon cooling precipitation occurs). The crude product was triturated with ethanol, and precipitate was collected on Büchner funnel and dried under reduced pressure to give BG5 (2-butenoic acid, 3-[[5-[[(E or Z)-3-ethoxy-1-methyl-3-oxo-1-propenyl]amino]-1-naphthalenyl]amino]-, ethyl ester, (E or Z)-) as the product with a yield of 11.39 g (94%). IR of BG5 (ATR): 3442, 3253, 2977, 2923, 1652, 1606, 1506, 1440, 1267, 1158, 787 cm$^{-1}$. A mixture of BG5 (2.00 g, 5.23 mmol) and Eaton's reagent (5.5 mL, 29.1 mmol, commercial, Aldrich) was stirred at 90° C. for 5 hours. The reaction mixture was cooled to 5° C. in an ice bath and carefully poured onto saturated ice-cold Na$_2$CO$_3$ solution (31 g Na$_2$CO$_3$/100 mL H$_2$O). The solid was filtered, filtrate was washed with water (3×50 mL), EtOH (10 mL) and dried under reduced pressure at 50° C. to give BG6 (quino[8,7-h]quinoline-1,7-dione, 4,10-dihydro-3,9-dimethyl-) as a product with a yield of 1.4276 g (94%). IR of BG6 (ATR): 3227, 3169, 3059, 2978, 1630, 1601, 1546, 1520, 1492, 1434, 1354, 1211, 1153, 1029, 843 cm$^{-1}$. $^1$H NMR of BG6 (200 MHz, TFA$_d$): 9.15 (d, J=9.6 Hz, 2H), 8.87 (d, J=9.6 Hz, 2H), 7.58 (s, 2H), 3.15 (s, 6H) ppm. $^{13}$C NMR of BG6 (50 MHz, TFA$_d$): 172.18, 139.66, 130.28, 127.79, 125.15, 123.15, 121.93, 111.70, 22.27 ppm. A suspension of BG6 (1.37 mg, 4.73 mmol) in POCl$_3$ (28.38 mL, 309.10 mmol) was heated at 90° C. for 6 hours, and continued at 120° C. for 14 hours. Upon cooling to room temperature, the mixture was slowly poured onto ice/water mixture and concentrated aqueous NH$_3$ was added until pH 9. Formed precipitate was filtered and washed well with H$_2$O and EtOH. The product BG7 (quino[8,7-h]quinoline, 1,7-dichloro-3,9-dimethyl-) was dried under reduced pressure at 60° C. with give a yield of 1.4442 g (93%). IR of BG7 (ATR): 2922, 1582, 1481, 1432, 1359, 1083, 1027, 877, 849, 829, 749 cm$^{-1}$. $^1$H NMR of BG7 (200 MHz, TFA$_d$): 9.30 (d, J=9.6 Hz, 2H), 8.78 (d, J=9.6 Hz, 2H), 8.18 (s, 2H), 3.10 (s, 6H) ppm. $^{13}$C NMR of BG7 (50 MHz, TFA$_d$): 162.18, 158.98, 138.44, 129.65, 129.52, 128.30, 127.52, 126.19, 22.45 ppm. A suspension of BG7 (160 mg, 0.49 mmol) in 6 mL of Me$_2$N(CH$_2$)$_3$NH$_2$ was stirred at reflux under Ar for 48 h. Then the mixture was poured onto 40 mL of ice-cold water. The obtained solid was filtered, and the cake was washed with MeOH (5 mL) and dried at 45° C. under reduced pressure to give BG8 (quino[8,7-h]quinoline-1,7-diamine, N$^1$,N$^7$-bis[3-(dimethylamino)propyl]-3,9-dimethyl-) with a yield of 579.4 mg (86%). M.p.=257-260° C.; IR of BG8 (ATR): 3334, 2950, 2860, 2824, 2772, 1586, 1535, 1353, 1175, 1100, 1022, 840, 815, 760 cm$^{-1}$. $^1$H NMR of BG8 (500 MHz, TFA$_d$): 9.00 (d, J=9.5 Hz, 2H), 8.57 (d, J=9.5 Hz, 2H), 7.07 (s, 2H), 3.99-3.97 (m, 4H), 3.67-3.64 (m, 4H), 3.22 (s, 12H), 3.06 (s, 6H), 2.62-2.57 (m, 4H) ppm. $^{13}$C NMR of BG8 (125 MHz, TFA$_d$): 158.13, 157.80, 137.58, 127.06, 122.40, 121.99, 103.02, 58.21, 45.36, 42.43, 25.41, 21.57 ppm. ESI-HRMS (m/z) of BG8: [M+2H]$^{2+}$ 230.16557 (error 1.72 ppm), [M+H]$^+$ 459.32310 (error 0.07 ppm). BG8 (300 mg, 0.65 mmol) was suspended in 10 mL of MeOH and the reaction mixture was vigorously stirred. 15 mL of 8.6 M EtOH/HCl solution was added and stirring was continued for 48 hours at room temperature. The solvent was removed under reduced pressure, and obtained solid was suspended in 21 mL of 96% EtOH, filtered, and the cake was washed with 9 mL of 96% EtOH. Upon drying at 45° C. under reduced pressure BG9 (quino[8,7-h]quinoline-1,7-diamine, N$^1$,N$^7$-bis[3-(dimethylamino)propyl]-3,9-dimethyl-, tetrachloride) was obtained (342.6 mg; 87%). BG9: Mp=>280° C.; IR (ATR): 3354, 3210, 2964, 2681, 2477, 1633, 1608, 1565, 1469, 1439, 1356, 1041, 830, 745 cm$^{-1}$; $^1$H NMR (500 MHz, CD$_3$OD): 8.99 (d, J=9.5 Hz, 2H), 8.66 (d, J=9.6 Hz, 2H), 7.16 (s, 2H), 3.83-3.79 (m, 4H), 3.44-3.40 (m, 4H), 2.98 (s, 12H), 2.94 (s, 6H) ppm; $^{13}$C NMR (125 MHz, CD$_3$OD): 157.03, 156.76, 137.09, 126.26, 122.57, 121.64, 116.73, 103.00, 56.57, 43.77, 42.02, 24.75, 21.12 ppm.

Synthesis of BG11

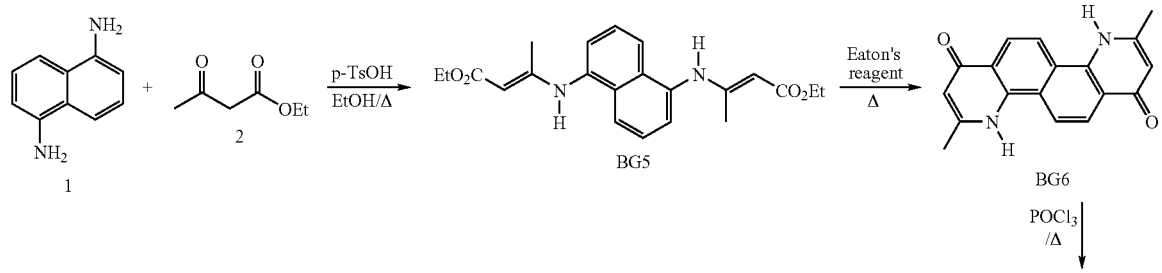

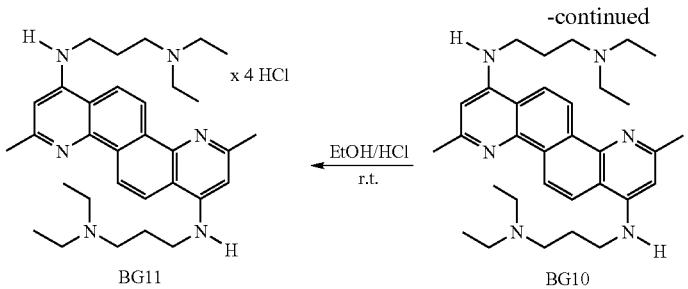
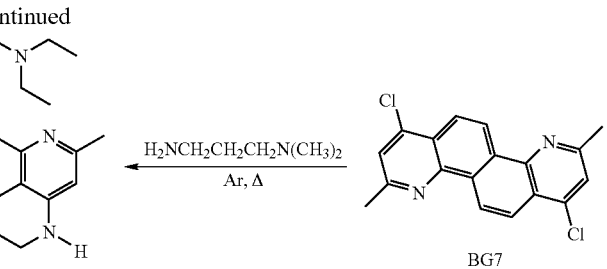

A suspension of 1,5-diaminonaphthalene 1 (5.0 g, 31.6 mmol), ethyl acetoacetate 2 (40 mL, 313.5 mmol) and p-TsOH (2.38 mg) in 250 mL of anhydrous ethanol was heated to reflux in a two-neck round bottom flask equipped with Dean-Stark trap filled molecular sieves (4 Å). After heating for 4 hours in an oil bath at a temperature of 120° C. with stirring, the mixture was cooled to room temperature and evaporated to dryness (upon cooling precipitation occurs). The crude product was triturated with ethanol, and precipitate was collected on Büchner funnel and dried under reduced pressure to give BG5 (2-butenoic acid, 3-[[5-[[(E or Z)-3-ethoxy-1-methyl-3-oxo-1-propenyl]amino]-1-naphthalenyl]amino]-, ethyl ester, (E or Z)-) as the product with a yield of 11.39 g (94%). IR of BG5 (ATR): 3442, 3253, 2977, 2923, 1652, 1606, 1506, 1440, 1267, 1158, 787 cm$^{-1}$. A mixture of BG5 (2.00 g, 5.23 mmol) and Eaton's reagent (5.5 mL, 29.1 mmol, commercial, Aldrich) was stirred at 90° C. for 5 hours. The reaction mixture was cooled to 5° C. in an ice bath and carefully poured onto saturated ice-cold Na$_2$CO$_3$ solution (31 g Na$_2$CO$_3$/100 mL H$_2$O). The solid was filtered, filtrate was washed with water (3×50 mL), EtOH (10 mL) and dried under reduced pressure at 50° C. to give BG6 (quino[8,7-h]quinoline-1,7-dione, 4,10-dihydro-3,9-dimethyl-) as a product with a yield of 1.4276 g (94%). IR of BG6 (ATR): 3227, 3169, 3059, 2978, 1630, 1601, 1546, 1520, 1492, 1434, 1354, 1211, 1153, 1029, 843 cm$^{-1}$. $^1$H NMR of BG6 (200 MHz, TFA$_d$): 9.15 (d, J=9.6 Hz, 2H), 8.87 (d, J=9.6 Hz, 2H), 7.58 (s, 2H), 3.15 (s, 6H) ppm. $^{13}$C NMR of BG6 (50 MHz, TFA$_d$): 172.18, 139.66, 130.28, 127.79, 125.15, 123.15, 121.93, 111.70, 22.27 ppm. A suspension of BG6 (1.37 mg, 4.73 mmol) in POCl$_3$ (28.38 mL, 309.10 mmol) was heated at 90° C. for 6 hours, and continued at 120° C. for 14 hours. Upon cooling to room temperature, the mixture was slowly poured onto ice/water mixture and concentrated aqueous NH$_3$ was added until pH 9. Formed precipitate was filtered and washed well with H$_2$O and EtOH. The product BG7 (quino[8,7-h]quinoline, 1,7-dichloro-3,9-dimethyl-) was dried under reduced pressure at 60° C. with give a yield of 1.4442 g (93%). IR of BG7 (ATR): 2922, 1582, 1481, 1432, 1359, 1083, 1027, 877, 849, 829, 749 cm$^{-1}$. $^1$H NMR of BG7 (200 MHz, TFA$_d$): 9.30 (d, J=9.6 Hz, 2H), 8.78 (d, J=9.6 Hz, 2H), 8.18 (s, 2H), 3.10 (s, 6H) ppm. $^{13}$C NMR of BG7 (50 MHz, TFA$_d$): 162.18, 158.98, 138.44, 129.65, 129.52, 128.30, 127.52, 126.19, 22.45 ppm. A suspension of BG7 (160 mg, 0.49 mmol) in 6 mL of Et$_2$N(CH$_2$)$_3$NH$_2$ was stirred at 150° C. under argon gas for 56 hours. Then the mixture was poured onto 40 mL of ice-cold water. The obtained solid was filtered, the cake was washed with MeOH (5 mL) and dried at 45° C. under reduced pressure to give BG10 (quino[8,7-h]quinoline-1,7-diamine, N$^1$,N$^7$-bis[3-(diethylamino)propyl]-3,9-dimethyl-) with a yield of 208.4 mg (83%). Mp.=192-195° C.

IR of BG10 (ATR): 3232, 2966, 2929, 2818, 1594, 1530, 1353, 1064, 1025, 831, 750 cm$^{-1}$. $^1$H NMR of BG10 (200 MHz, CD$_3$CO$_2$D): 9.05 (d, J=9.4 Hz, 2H), 8.59 (d, J=9.4 Hz, 2H), 7.01 (s, 2H), 3.91-3.84 (m, 4H), 3.51-3.18 (m, 8H), 2.90 (s, 6H), 2.45-2.27 (m, 4H), 1.32 (t, J=7.1 Hz, 12H) ppm. $^{13}$C NMR of BG10 (50 MHz, CD$_3$CO$_2$D): 156.64, 156.12, 136.57, 125.95, 122.08, 121.53, 116.36, 102.33, 50.46, 47.64, 41.81, 23.60, 8.62 ppm. ESI-HRMS (m/z) of BG10: [M+2H]$^{2+}$ 258.19756 (error 2.08 ppm), [M+H]$^+$ 515.38770 (error 0.36 ppm). BG10 (300 mg, 0.58 mmol) was suspended in 10 mL of MeOH and the reaction mixture was vigorously stirred. 15 mL of 8.6 M EtOH/HCl solution was added and stirring was continued for 48 hours at room temperature. The solvent was removed under reduced pressure, and obtained solid was suspended in 21 mL of 96% EtOH, filtered, and the cake was washed with 9 mL of 96% EtOH. Upon drying at 45° C. under reduced pressure BG11 (quino[8,7-h]quinoline-1,7-diamine, N$^1$,N$^7$-bis[3-(diethylamino)propyl]-3,9-dimethyl-, tetrahydrochloride) was obtained (303.5 mg; 79%). BG11: Mp=>280° C.; IR (ATR): 3164, 2949, 2575, 2478, 1632, 1610, 1560, 1468, 1439, 1347, 1030, 821, 750 cm$^{-1}$; $^1$H NMR (500 MHz, CD$_3$OD): 9.07 (d, J=9.5 Hz, 2H), 8.74 (d, J=9.5 Hz, 2H), 7.20 (s, 2H), 3.83-3.80 (m, 4H), 3.40-3.38 (m, 4H), 2.96 (s, 12H), 2.35-2.29 (m, 4H), 1.38 (t, J=7.2 Hz, 12H) ppm; $^{13}$C NMR (125 MHz, CD$_3$OD): 157.20, 156.75, 137.19, 126.41, 122.66, 121.72, 116.87, 103.02, 50.98, 48.71, 24.24, 21.03, 9.36 ppm.

Synthesis of BG15

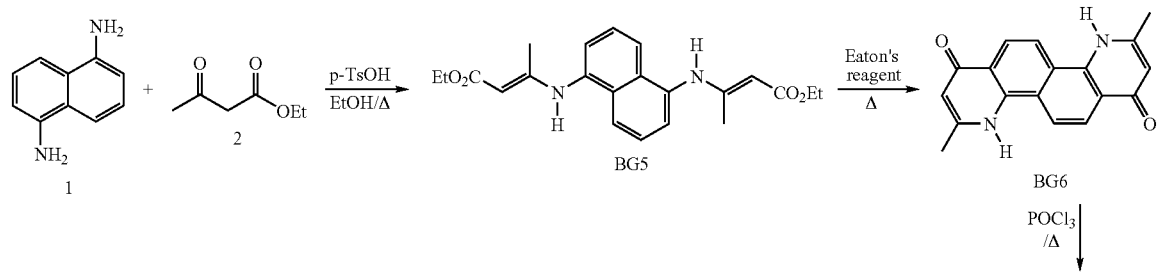

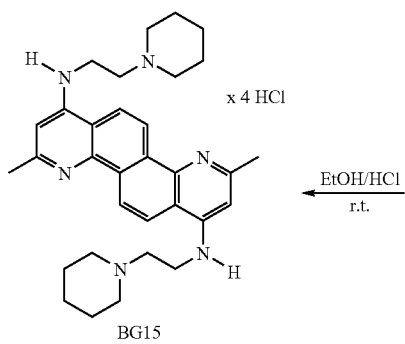
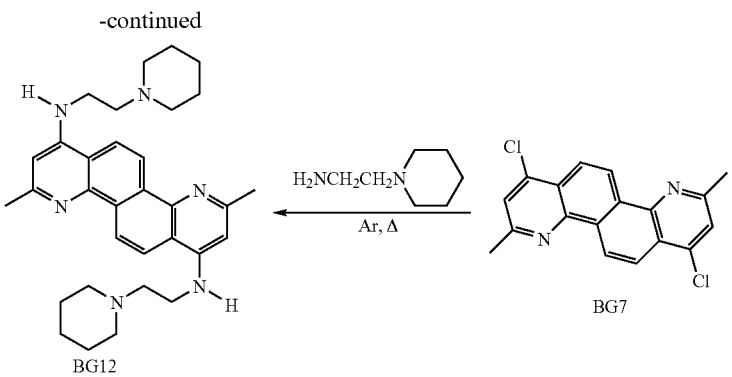

A suspension of 1,5-diaminonaphthalene 1 (5.0 g, 31.6 mmol), ethyl acetoacetate 2 (40 mL, 313.5 mmol) and p-TsOH (2.38 mg) in 250 mL of anhydrous ethanol was heated to reflux in a two-neck round bottom flask equipped with Dean-Stark trap filled molecular sieves (4 Å). After heating for 4 hours in an oil bath at a temperature of 120° C. with stirring, the mixture was cooled to room temperature and evaporated to dryness (upon cooling precipitation occurs). The crude product was triturated with ethanol, and precipitate was collected on Büchner funnel and dried under reduced pressure to give BG5 (2-butenoic acid, 3-[[5-[[(E or Z)-3-ethoxy-1-methyl-3-oxo-1-propenyl]amino]-1-naphthalenyl]amino]-, ethyl ester, (E or Z)-) as the product with a yield of 11.39 g (94%). IR of BG5 (ATR): 3442, 3253, 2977, 2923, 1652, 1606, 1506, 1440, 1267, 1158, 787 cm$^{-1}$. A mixture of BG5 (2.00 g, 5.23 mmol) and Eaton's reagent (5.5 mL, 29.1 mmol, commercial, Aldrich) was stirred at 90° C. for 5 hours. The reaction mixture was cooled to 5° C. in an ice bath and carefully poured onto saturated ice-cold Na$_2$CO$_3$ solution (31 g Na$_2$CO$_3$/100 mL H$_2$O). The solid was filtered, filtrate was washed with water (3×50 mL), EtOH (10 mL) and dried under reduced pressure at 50° C. to give BG6 (quino[8,7-h]quinoline-1,7-dione, 4,10-dihydro-3,9-dimethyl as a product with a yield of 1.4276 g (94%). IR of BG6 (ATR): 3227, 3169, 3059, 2978, 1630, 1601, 1546, 1520, 1492, 1434, 1354, 1211, 1153, 1029, 843 cm$^{-1}$. $^1$H NMR of BG6 (200 MHz, TFA$_d$): 9.15 (d, J=9.6 Hz, 2H), 8.87 (d, J=9.6 Hz, 2H), 7.58 (s, 2H), 3.15 (s, 6H) ppm. $^{13}$C NMR of BG6 (50 MHz, TFA$_d$): 172.18, 139.66, 130.28, 127.79, 125.15, 123.15, 121.93, 111.70, 22.27 ppm. A suspension of BG6 (1.37 mg, 4.73 mmol) in POCl$_3$ (28.38 mL, 309.10 mmol) was heated at 90° C. for 6 hours, and continued at 120° C. for 14 hours. Upon cooling to room temperature, the mixture was slowly poured onto ice/water mixture and concentrated aqueous NH$_3$ was added until pH 9. Formed precipitate was filtered and washed well with H$_2$O and EtOH. The product BG7 (quino[8,7-h]quinoline, 1,7-dichloro-3,9-dimethyl-) was dried under reduced pressure at 60° C. with give a yield of 1.4442 g (93%). IR of BG7 (ATR): 2922, 1582, 1481, 1432, 1359, 1083, 1027, 877, 849, 829, 749 cm$^{-1}$. $^1$H NMR of BG7 (200 MHz, TFA$_d$): 9.30 (d, J=9.6 Hz, 2H), 8.78 (d, J=9.6 Hz, 2H), 8.18 (s, 2H), 3.10 (s, 6H) ppm. $^{13}$C NMR of BG7 (50 MHz, TFA$_d$): 162.18, 158.98, 138.44, 129.65, 129.52, 128.30, 127.52, 126.19, 22.45 ppm. A suspension of BG7 (200 mg, 0.61 mmol) in 3 mL of 2-piperidin-1-yl-ethylamine was stirred at 170-180° C. under argon gas for 10 hours. Then the mixture was poured onto 40 mL of ice-cold water. The obtained solid was filtered, the cake was washed with 5 mL of MeOH and dried at 45° C. under reduced pressure to give BG12 in a yield of 255 mg (82%). Mp=306-310° C.; IR of BG12 (ATR): 3376, 2925, 2841, 2767, 1594, 1580, 1465, 1123, 1038, 750 cm$^{-1}$. ESI-HRMS (m/z) of BG12: [M+2H]$^{2+}$ 256.18169 (error 3.38 ppm), [M+H]$^+$ 511.35584 (error 2.87 ppm). BG12 (390 mg, 0.76 mmol) was suspended in 10 mL of MeOH and the reaction mixture was vigorously stirred. 15 mL of 8.6 M EtOH/HCl solution was added and stirring was continued for 48 hours at room temperature. The solvent was removed under reduced pressure, and obtained solid was suspended in 21 mL of 96% EtOH, filtered, and the cake was washed with 9 mL of 96% EtOH. Upon drying at 45° C. under reduced pressure BG15 (quino[8,7-h]quinoline-1,7-diamine, 3,9-dimethyl-N$^1$,N$^7$-bis[2-(1-piperidinyl)ethyl]-, tetrahydrochloride) was obtained (341.6 mg; 68%). BG15: Mp=>280° C.; IR (ATR): 3345, 3224, 2943, 2644, 1634, 1608, 1564, 1438, 1360, 831, 744 cm$^{-1}$; $^1$H NMR (500 MHz, D$_2$O): 8.86 (d, J=9.5 Hz, 2H), 8.48 (d, J=9.5 Hz, 2H), 7.19 (s, 2H), 4.29-4.24 (m, 4H), 3.83 (bd, J=12 Hz, 4H), 3.74-3.70 (m, 4H), 3.27-3.21 (m, 4H), 3.02 (s, 6H), 2.15-2.10 (m, 4H), 2.01-1.92 (m, 6H), 1.59-1.52 (m, 2H) ppm; $^{13}$C NMR (125 MHz, D$_2$O): 158.28, 158.21, 138.14, 127.37, 123.45, 122.95, 118.13, 104.39, 56.63, 40.54, 25.57, 23.81, 23.03 ppm.

Synthesis of BG16

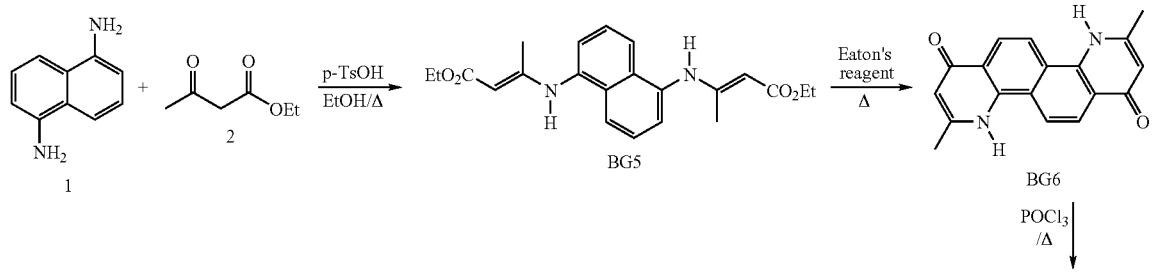

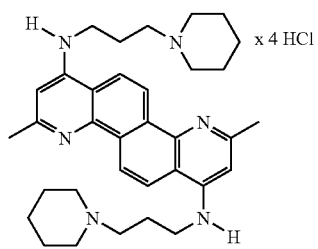

A suspension of 1,5-diaminonaphthalene 1 (5.0 g, 31.6 mmol), ethyl acetoacetate 2 (40 mL, 313.5 mmol) and p-TsOH (2.38 mg) in 250 mL of anhydrous ethanol was heated to reflux in a two-neck round bottom flask equipped with Dean-Stark trap filled molecular sieves (4 Å). After heating for 4 hours in an oil bath at a temperature of 120° C. with stirring, the mixture was cooled to room temperature and evaporated to dryness (upon cooling precipitation occurs). The crude product was triturated with ethanol, and precipitate was collected on Büchner funnel and dried under reduced pressure to give BG5 (2-butenoic acid, 3-[[5-[[(E or Z)-3-ethoxy-1-methyl-3-oxo-1-propenyl]amino]-1-naphthalenyl]amino]-, ethyl ester, (E or Z)-) as the product with a yield of 11.39 g (94%). IR of BG5 (ATR): 3442, 3253, 2977, 2923, 1652, 1606, 1506, 1440, 1267, 1158, 787 cm⁻¹. A mixture of BG5 (2.00 g, 5.23 mmol) and Eaton's reagent (5.5 mL, 29.1 mmol, commercial, Aldrich) was stirred at 90° C. for 5 hours. The reaction mixture was cooled to 5° C. in an ice bath and carefully poured onto saturated ice-cold $Na_2CO_3$ solution (31 g $Na_2CO_3$/100 mL $H_2O$). The solid was filtered, filtrate was washed with water (3×50 mL), EtOH (10 mL) and dried under reduced pressure at 50° C. to give BG6 (quino[8,7-h]quinoline-1,7-dione, 4,10-dihydro-3,9-dimethyl-) as a product with a yield of 1.4276 g (94%). IR of BG6 (ATR): 3227, 3169, 3059, 2978, 1630, 1601, 1546, 1520, 1492, 1434, 1354, 1211, 1153, 1029, 843 cm⁻¹. ¹H NMR of BG6 (200 MHz, $TFA_d$): 9.15 (d, J=9.6 Hz, 2H), 8.87 (d, J=9.6 Hz, 2H), 7.58 (s, 2H), 3.15 (s, 6H) ppm. ¹³C NMR of BG6 (50 MHz, $TFA_d$): 172.18, 139.66, 130.28, 127.79, 125.15, 123.15, 121.93, 111.70, 22.27 ppm. A suspension of BG6 (1.37 mg, 4.73 mmol) in $POCl_3$ (28.38 mL, 309.10 mmol) was heated at 90° C. for 6 hours, and continued at 120° C. for 14 hours. Upon cooling to room temperature, the mixture was slowly poured onto ice/water mixture and concentrated aqueous $NH_3$ was added until pH 9. Formed precipitate was filtered and washed well with $H_2O$ and EtOH. The product BG7 (quino[8,7-h]quinoline, 1,7-dichloro-3,9-dimethyl-) was dried under reduced pressure at 60° C. with give a yield of 1.4442 g (93%). IR of BG7 (ATR): 2922, 1582, 1481, 1432, 1359, 1083, 1027, 877, 849, 829, 749 cm⁻¹. ¹H NMR of BG7 (200 MHz, $TFA_d$): 9.30 (d, J=9.6 Hz, 2H), 8.78 (d, J=9.6 Hz, 2H), 8.18 (s, 2H), 3.10 (s, 6H) ppm. ¹³C NMR of BG7 (50 MHz, $TFA_d$): 162.18, 158.98, 138.44, 129.65, 129.52, 128.30, 127.52, 126.19, 22.45 ppm. A suspension of BG7 (200 mg, 0.61 mmol) in 2-piperidin-1-yl-propylamine was stirred at 170-180° C. under argon gas for 10 hours. Then the mixture was poured onto 40 mL of ice-cold water. The obtained solid was filtered, the cake was washed with 5 mL of MeOH and dried at 45° C. under reduced pressure to give BG13 (quino[8,7-h]quinoline-1,7-diamine, 3,9-dimethyl-$N^1$,$N^7$-bis[3-(1-piperidinyl)propyl]-) with a yield 293 mg (89%). Mp.=304-307° C.

IR (ATR): 3263, 2920, 2850, 2804, 1581, 1526, 1468, 1435, 1116, 1027, 751 cm¹

ESI-HRMS (m/z): $[M+2H]^{2+}$ 270.19601 (error 1.73 ppm), $[M+H]^+$ 539.38481 (error 1.61 ppm). BG13 (450 mg, 0.83 mmol) was suspended in MeOH (10 mL) and the reaction mixture was vigorously stirred. EtOH/HCl solution (8.6M) was added and stirring was continued for 48 hours at room temperature. The solvent was removed under reduced pressure, and obtained solid was suspended in 96% EtOH (21 mL), filtered, and the cake was washed with 96% EtOH (9 mL). Upon drying at 45° C. under reduced pressure BG16 (quino[8,7-h]quinoline-1,7-diamine, 3,9-dimethyl-$N^1$,$N^7$-bis[3-(1-piperidinyl)propyl]-, tetrahydrochloride) was obtained (509.1 mg; 89%). BG16: Mp=>280° C.; IR (ATR): 3361, 3182, 2944, 2536, 1636, 1606, 1562, 1438, 1354, 835, 745 cm⁻¹; ¹H NMR (500 MHz, $CD_3OD$): 9.11 (d, J=8.5 Hz, 2H), 8.77 (d, J=8.5 Hz, 2H), 7.18 (s, 2H), 3.83-3.79 (m, 4H), 3.62 (bd, J=12 Hz, 4H), 3.37-3.30 (m, 4H), 3.07-2.95 (m, 4H), 2.95 (s, 6H), 2.39-2.32 (m, 4H), 2.00-1.84 (m, 10H), 1.59-1.51 (m, 2H) ppm; ¹³C NMR (125 MHz, $CD_3OD$): 157.29, 156.73, 137.27, 126.55, 122.71, 121.69, 116.96, 55.75, 54.64, 42.12, 24.43, 24.12, 22.86, 20.97 ppm.

Synthesis of BG17

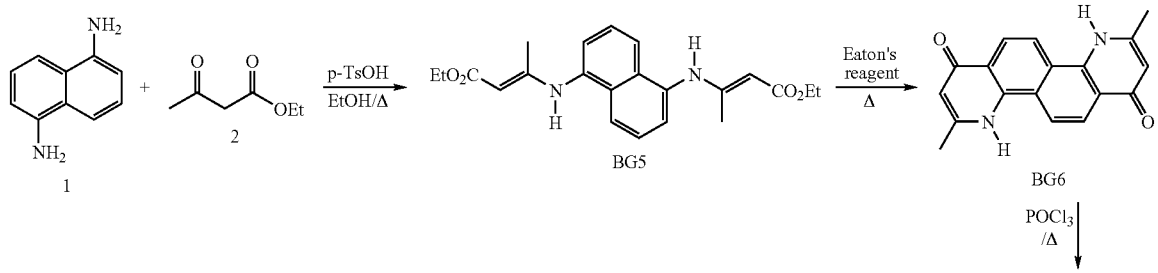

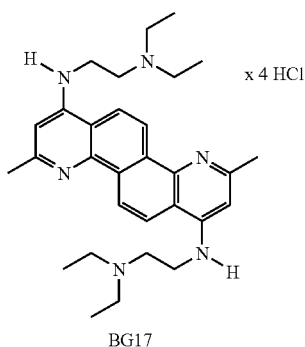
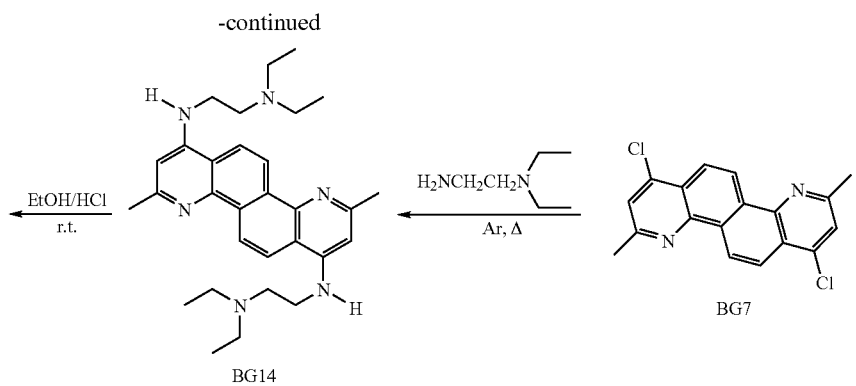

A suspension of 1,5-diaminonaphthalene 1 (5.0 g, 31.6 mmol), ethyl acetoacetate 2 (40 mL, 313.5 mmol) and p-TsOH (2.38 mg) in 250 mL of anhydrous ethanol was heated to reflux in a two-neck round bottom flask equipped with Dean-Stark trap filled molecular sieves (4 Å). After heating for 4 hours in an oil bath at a temperature of 120° C. with stirring, the mixture was cooled to room temperature and evaporated to dryness (upon cooling precipitation occurs). The crude product was triturated with ethanol, and precipitate was collected on Büchner funnel and dried under reduced pressure to give BG5 (2-butenoic acid, 3-[[5-[[(E or Z)-3-ethoxy-1-methyl-3-oxo-1-propenyl]amino]-1-naphthalenyl] amino]-, ethyl ester, (E or Z)-) as the product with a yield of 11.39 g (94%). IR of BG5 (ATR): 3442, 3253, 2977, 2923, 1652, 1606, 1506, 1440, 1267, 1158, 787 cm$^{-1}$. A mixture of BG5 (2.00 g, 5.23 mmol) and Eaton's reagent (5.5 mL, 29.1 mmol, commercial, Aldrich) was stirred at 90° C. for 5 hours. The reaction mixture was cooled to 5° C. in an ice bath and carefully poured onto saturated ice-cold Na$_2$CO$_3$ solution (31 g Na$_2$CO$_3$/100 mL H$_2$O). The solid was filtered, filtrate was washed with water (3×50 mL), EtOH (10 mL) and dried under reduced pressure at 50° C. to give BG6 (quino[8,7-h]quinoline-1,7-dione, 4,10-dihydro-3,9-dimethyl-) as a product with a yield of 1.4276 g (94%). IR of BG6 (ATR): 3227, 3169, 3059, 2978, 1630, 1601, 1546, 1520, 1492, 1434, 1354, 1211, 1153, 1029, 843 cm$^{-1}$. $^1$H NMR of BG6 (200 MHz, TFA$_d$): 9.15 (d, J=9.6 Hz, 2H), 8.87 (d, J=9.6 Hz, 2H), 7.58 (s, 2H), 3.15 (s, 6H) ppm. $^{13}$C NMR of BG6 (50 MHz, TFA$_d$): 172.18, 139.66, 130.28, 127.79, 125.15, 123.15, 121.93, 111.70, 22.27 ppm. A suspension of BG6 (1.37 mg, 4.73 mmol) in POCl$_3$ (28.38 mL, 309.10 mmol) was heated at 90° C. for 6 hours, and continued at 120° C. for 14 hours. Upon cooling to room temperature, the mixture was slowly poured onto ice/water mixture and concentrated aqueous NH$_3$ was added until pH 9. Formed precipitate was filtered and washed well with H$_2$O and EtOH. The product BG7 (quino[8,7-h]quinoline, 1,7-dichloro-3,9-dimethyl-) was dried under reduced pressure at 60° C. with give a yield of 1.4442 g (93%). IR of BG7 (ATR): 2922, 1582, 1481, 1432, 1359, 1083, 1027, 877, 849, 829, 749 cm$^{-1}$. $^1$H NMR of BG7 (200 MHz, TFA$_d$): 9.30 (d, J=9.6 Hz, 2H), 8.78 (d, J=9.6 Hz, 2H), 8.18 (s, 2H), 3.10 (s, 6H) ppm. $^{13}$C NMR of BG7 (50 MHz, TFA$_d$): 162.18, 158.98, 138.44, 129.65, 129.52, 128.30, 127.52, 126.19, 22.45 ppm. A suspension of BG7 (300 mg, 0.92 mmol) in 11 mL of Et$_2$N(CH$_2$)$_2$NH$_2$ was stirred at reflux under argon gas for 45 hours. Then the mixture was poured onto ice-cold water (40 mL). The obtained solid was filtered, the cake was washed with MeOH (5 mL) and dried at 45° C. under reduced pressure to give BG14 (quino[8,7-h]quinoline-1,7-diamine, $N^1,N^7$-bis[2-(diethylamino)ethyl]-3,9-dimethyl-) with a yield of 268 mg (90%). Mp.=242-246° C.; IR of BG14 (ATR): 3376, 2973, 2842, 1594, 1578, 1518, 1360, 1334, 1024, 828, 751 cm$^{-1}$. $^1$H NMR of BG14 (200 MHz, TFA$_d$): 8.73 (d, J=8.8 Hz, 2H), 8.24 (d, J=8.8 Hz, 2H), 6.81 (s, 2H), 4.05 (bs, 4H), 3.52 (bs, 4H), 3.24 (bs, 8H), 2.73 (s, 6H), 1.32 (bs, 12H) ppm. $^{13}$C NMR of BG14 (50 MHz, TFA$_d$): 159.19, 158.70, 138.18, 127.68, 123.06, 118.40, 104.01, 53.14, 50.76, 40.95, 22.21, 9.54 ppm. ESI-HRMS (m/z) of BG14: [M+2H]$^{2+}$ 244.18208 (error 5.13 ppm), [M+H]$^+$ 487.35548 (error 2.28 ppm). BG14 (223 mg, 0.46 mmol) was suspended in MeOH (10 mL) and the reaction mixture was vigorously stirred. EtOH/HCl solution (8.6M) was added and stirring was continued for 48 hours at room temperature. The solvent was removed under reduced pressure, and obtained solid was suspended in 96% EtOH (21 mL), filtered, and the cake was washed with 96% EtOH (9 mL). Upon drying at 45° C. under reduced pressure BG17 (quino[8,7-h]quinoline-1,7-diamine, $N^1,N^7$-bis[2-(diethylamino)ethyl]-3,9-dimethyl-, tetrahydrochloride) was obtained (176 mg; 61%). BG17: Mp=>280° C.; IR (ATR): 3384, 3188, 3066, 2663, 1635, 1610, 1556, 1441, 1348, 1071, 830, 744 cm$^{-1}$; $^1$H NMR (500 MHz, CD$_3$OD): 9.14 (d, J=9.0 Hz, 2H), 8.85 (d, J=9.0 Hz, 2H), 7.30 (s, 2H), 4.18-4.14 (m, 4H), 3.68-3.63 (m, 4H), 3.46-3.38 (m, 8H), 2.97 (s, 6H), 1.44-1.40 (m, 12H) ppm; $^{13}$C NMR (125 MHz, CD$_3$OD): 157.37, 157.22, 137.49, 126.68, 123.01, 121.88, 117.29, 103.41, 51.11, 39.68, 21.05, 9.16 ppm.

Synthesis of BG20

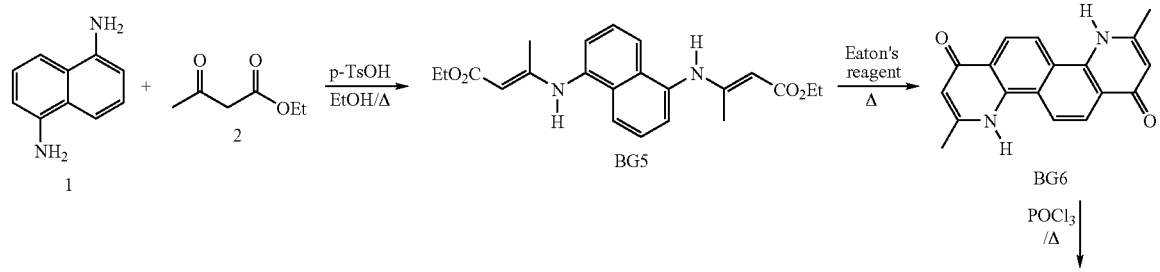

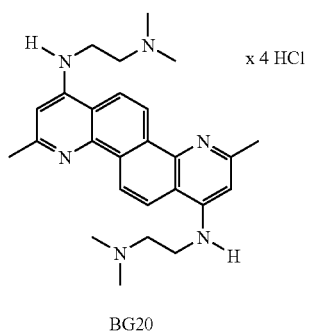 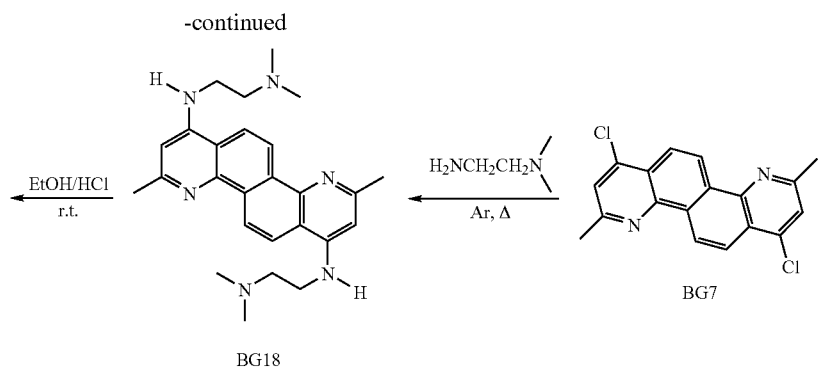

A suspension of 1,5-diaminonaphthalene 1 (5.0 g, 31.6 mmol), ethyl acetoacetate 2 (40 mL, 313.5 mmol) and p-TsOH (2.38 mg) in 250 mL of anhydrous ethanol was heated to reflux in a two-neck round bottom flask equipped with Dean-Stark trap filled molecular sieves (4 Å). After heating for 4 hours in an oil bath at a temperature of 120° C. with stirring, the mixture was cooled to room temperature and evaporated to dryness (upon cooling precipitation occurs). The crude product was triturated with ethanol, and precipitate was collected on Büchner funnel and dried under reduced pressure to give BG5 (2-butenoic acid, 3-[[5-[[(E or Z)-3-ethoxy-1-methyl-3-oxo-1-propenyl]amino]-1-naphthalenyl]amino]-, ethyl ester, (E or Z)-) as the product with a yield of 11.39 g (94%). IR of BG5 (ATR): 3442, 3253, 2977, 2923, 1652, 1606, 1506, 1440, 1267, 1158, 787 cm$^{-1}$. A mixture of BG5 (2.00 g, 5.23 mmol) and Eaton's reagent (5.5 mL, 29.1 mmol, commercial, Aldrich) was stirred at 90° C. for 5 hours. The reaction mixture was cooled to 5° C. in an ice bath and carefully poured onto saturated ice-cold $Na_2CO_3$ solution (31 g $Na_2CO_3$/100 mL $H_2O$). The solid was filtered, filtrate was washed with water (3×50 mL), EtOH (10 mL) and dried under reduced pressure at 50° C. to give BG6 (quino[8,7-h]quinoline-1,7-dione, 4,10-dihydro-3,9-dimethyl-) as a product with a yield of 1.4276 g (94%). IR of BG6 (ATR): 3227, 3169, 3059, 2978, 1630, 1601, 1546, 1520, 1492, 1434, 1354, 1211, 1153, 1029, 843 cm$^{-1}$. $^1$H NMR of BG6 (200 MHz, TFA$_d$): 9.15 (d, J=9.6 Hz, 2H), 8.87 (d, J=9.6 Hz, 2H), 7.58 (s, 2H), 3.15 (s, 6H) ppm. $^{13}$C NMR of BG6 (50 MHz, TFA$_d$): 172.18, 139.66, 130.28, 127.79, 125.15, 123.15, 121.93, 111.70, 22.27 ppm. A suspension of BG6 (1.37 mg, 4.73 mmol) in $POCl_3$ (28.38 mL, 309.10 mmol) was heated at 90° C. for 6 hours, and continued at 120° C. for 14 hours. Upon cooling to room temperature, the mixture was slowly poured onto ice/water mixture and concentrated aqueous $NH_3$ was added until pH 9. Formed precipitate was filtered and washed well with $H_2O$ and EtOH. The product BG7 (quino[8,7-h]quinoline, 1,7-dichloro-3,9-dimethyl-) was dried under reduced pressure at 60° C. with give a yield of 1.4442 g (93%). IR of BG7 (ATR): 2922, 1582, 1481, 1432, 1359, 1083, 1027, 877, 849, 829, 749 cm$^{-1}$. $^1$H NMR of BG7 (200 MHz, TFA$_d$): 9.30 (d, J=9.6 Hz, 2H), 8.78 (d, J=9.6 Hz, 2H), 8.18 (s, 2H), 3.10 (s, 6H) ppm. $^{13}$C NMR of BG7 (50 MHz, TFA$_d$): 162.18, 158.98, 138.44, 129.65, 129.52, 128.30, 127.52, 126.19, 22.45 ppm. A suspension of BG7 (300 mg, 0.92 mmol) in $Me_2N(CH_2)_2$ $NH_2$ was stirred at reflux under argon gas for 7 days. Then the mixture was poured onto ice-cold water (40 mL). The obtained solid was filtered, the cake was washed with MeOH (5 mL), and dried at 45° C. under reduced pressure to give BG18 (quino[8,7-h]quinoline-1,7-diamine, $N^1,N^7$-bis[2-(dimethylamino)ethyl]-3,9-dimethyl-) with a yield of 534 mg (81%). Mp.=317-318° C.

IR of BG18 (ATR): 3401, 2944, 2816, 2763, 1598, 1578, 1524, 1458, 1102, 1042, 1023, 812, 787, 747 cm$^{-1}$. $^1$H NMR of BG18 (200 MHz, $CD_3CO_2D$): 9.10 (d, J=9.6 Hz, 2H), 8.49 (d, J=9.6 Hz, 2H), 7.11 (s, 2H), 4.20 (bs, 4H), 3.71 (bs, 4H), 3.04 (s, 12H), 2.91 (s, 6H) ppm. $^{13}$C NMR of BG18 (50 MHz, $CD_3CO_2D$): 156.64, 156.60, 136.57, 125.92, 121.97, 116.60, 102.79, 55.85, 43.76, 39.43, 20.81 ppm. ESI-HRMS (m/z): [M+2H]$^{2+}$ 216.14969 (error 0.78 ppm), [M+H]$^+$ 431.29161 (error 0.37 ppm). BG18 (338 mg, 0.78 mmol) was suspended in MeOH (10 mL) and the reaction mixture was vigorously stirred. EtOH/HCl solution (8.6M) was added and stirring was continued for 48 hours at room temperature. The solvent was removed under reduced pressure, and obtained solid was suspended in 96% EtOH (21 mL), filtered, and the cake was washed with 96% EtOH (9 mL). Upon drying at 45° C. under reduced pressure BG20 (quino[8,7-h]quinoline-1,7-diamine, $N^1,N^7$-bis[2-(dimethylamino)ethyl]-3,9-dimethyl-, tetrahydrochloride) was obtained (382.9 mg; 85%). BG20: Mp=>280° C.; IR (ATR): 3430, 3361, 3180, 3068, 3029, 2974, 2699, 1634, 1609, 1554, 1445, 1344, 988, 828, 746 cm$^{-1}$; $^1$H NMR (200 MHz, $D_2O$): 8.69 (d, J=9.6 Hz, 2H), 8.39 (d, J=9.6 Hz, 2H), 7.24 (s, 2H), 4.34-4.20 (m, 4H), 3.89-3.78 (m, 4H), 3.22 (s, 12H), 3.02 (s, 6H) ppm; $^{13}$C NMR (50 MHz, $D_2O$): 158.40, 138.50, 127.77, 123.58, 123.22, 118.57, 104.57, 57.56, 57.14, 46.01, 41.02, 23.00, 21.85, 17.74 ppm.

Compositions of the present invention may further comprise a pharmaceutical composition comprising a therapeutically effective amount of any of the small molecules (or combinations of small molecules) described above together with other materials, such as a suitable carrier, excipient, etc., for administration to a human or animal experiencing a viral infection or at risk of a viral infection. Such pharmaceutical compositions may be either in solid, gel or liquid form and may be administered as appropriate to an individual IV, IM, IP or parenterally, topically, orally, or through mucosal surfaces and routes (including, for example, rectal and vaginal suppositories). The exact dosage corresponding to a therapeutically effective amount will vary from mammal to mammal and virus to virus. The dosage ranges set forth above in specific examples for each of the FGI-103 compounds tested are representative, and provide sufficient information to those of skill in the art, following the assay procedures set forth herein and known to those of skill in the art, to arrive at suitable dosage values for any given virus and mammalian host. Those of skill in the art are well equipped by conventional protocols, given the identification of targets and compounds herein, to identify specific dosages for specific mammals, specific viruses, and specific modes of administration. See, e.g., "Remington: The Science and Practice of Pharmacy," University of the Sciences in Philadelphia, 21st ed., Mack Publishing Co., (2005), the disclosure of which is hereby incorporated by reference in its entirety.

A "therapeutically effective" amount of the inventive compositions can be determined by prevention or amelioration of viral infection of host cells or viral disease in a patient or animal. It will be understood that, when administered to a human patient, the total daily usage of the agents or composition of the present invention will be decided by the attending physician within the scope of sound medical judgment. The specific therapeutically effective dose level for any particular patient will depend upon a variety of factors: the type and degree of the cellular or physiological response to be achieved; activity of the specific composition employed; the specific agents or composition employed; the age, body weight, general health, sex and diet of the patient; the time of administration, route of administration, and rate of excretion of the composition; the duration of the treatment; drugs used in combination or coincidental with the composition; and like factors well known in the medical and veterinary arts. For example, it is well within the skill of the art to start doses of the agents at levels lower than those required to achieve the desired therapeutic effect and to gradually increase the dosages until the desired effect is achieved.

While the present invention has been disclosed with reference to certain embodiments and examples, numerous modification, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of inhibiting viral infection in a mammal in need of same, comprising administering an effective amount of 2-[2-(5-carbamimidoyl-benzofuran-2-yl)-vinyl]-H-benzoimidazole-5-carboxamidineto said mammal wherein said viral infection is caused by a virus selected from the group consisting of respiratory syncytialvirus, influenza virus, parainfluenza virus, porcine reproductive and respiratory virus, human metapneumovirus, a coronavirus and severe acute respiratory syndrome virus.

2. The method of claim 1, wherein said virus is influenza, porcine reproductive and respiratory syndrome virus, or parainfluenza.

3. The method of claim 1 wherein said administration is parenteral, or applied to mucosal surfaces, through inhalation.

4. The method of claim 3, wherein said parenteral administration is IP, IVm subcutaneous or cutaneous.

5. The method of claim 1, wherein said 2-[2-(5-carbamimidoyl-benzofuran-2-yl)-vinyl]-H-benzoimidazole-5-carboxamidine is administered as a pharmaceutically acceptable solution or suspension.

6. The method of claim 1, wherein said 2-[2-(5-carbamimidoyl-benzofuran-2-yl)-vinyl]-H-benzoimidazole 5 carboxamidine is administered in a range of 1 ng-200 mg/kg of body weight.

7. The method of claim 6, wherein said 2-[2-(5-carbamimidoyl-benzofuran-2-yl)-vinyl]-H-benzoimidazole-5-carboxamidine is administered in a range of 1 ng-1 mg/kg of body weight.

8. The method of claim 1, wherein said 2-[2-(5 carbamimidoyl-benzofuran-2-yl)-vinyl]-H-benzoimidazole-5-carboxamidine is administered therapeutically to said host, subsequent to initial infection by said virus.

9. The method of claim 1, wherein said virus is respiratory syncytial virus.

* * * * *